US011235115B2

(12) United States Patent
Crumblin et al.

(10) Patent No.: US 11,235,115 B2
(45) Date of Patent: Feb. 1, 2022

(54) BREATHABLE GAS APPARATUS WITH HUMIDIFIER

(71) Applicant: ResMed Pty Ltd, Bella Vista (AU)

(72) Inventors: Geoffrey Crumblin, Sydney (AU); Michael Thomas Janiak, Sydney (AU); Dan Kao, Sydney (AU); Barton John Kenyon, Sydney (AU); Perry David Lithgow, Sydney (AU); Rohan Neil Primrose, Sydney (AU); Jim Saada, Sydney (AU); John Michael Snow, Sydney (AU); Duncan Lovel Trevor-Wilson, Sydney (AU); Alexander Virr, Gosford (AU); Arthur Kin-Wai Yee, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

(21) Appl. No.: 17/318,393

(22) Filed: May 12, 2021

(65) Prior Publication Data

US 2021/0260316 A1    Aug. 26, 2021

Related U.S. Application Data

(63) Continuation of application No. 17/102,756, filed on Nov. 24, 2020, now abandoned, which is a
(Continued)

(30) Foreign Application Priority Data

| Jun. 20, 2003 | (AU) | 2003903139 |
| Sep. 22, 2003 | (AU) | 2003905136 |
| Feb. 27, 2004 | (AU) | 2004901008 |

(51) Int. Cl.
*A61M 16/00* (2006.01)
*A61M 16/10* (2006.01)
(Continued)

(52) U.S. Cl.
CPC ........ *A61M 16/0066* (2013.01); *A61M 16/00* (2013.01); *A61M 16/0003* (2014.02);
(Continued)

(58) Field of Classification Search
CPC .............. A61M 16/00; A61M 16/0051; A61M 16/0057; A61M 16/006; A61M 16/0063;
(Continued)

(56) References Cited

U.S. PATENT DOCUMENTS

| 1,974,843 A | 9/1934 | Blashfield |
| RE19,826 E | 1/1936 | Aisenstein |

(Continued)

FOREIGN PATENT DOCUMENTS

| CN | 2086150 | 10/1991 |
| CN | 2239819 | 11/1996 |

(Continued)

OTHER PUBLICATIONS

Jan. 23, 2019 Letter from Baldwins Intellectual Property Reporting Opposition Filed in New Zealand Patent Application No. 728764.
(Continued)

*Primary Examiner* — Rachel T Sippel
(74) *Attorney, Agent, or Firm* — Nixon & Vanderhye P.C.

(57) ABSTRACT

A humidifier assembly is configured to humidify a pressurized flow of breathable gas from a flow generator of a CPAP unit and includes a base configured to be attached to the flow generator, the base including a recess portion. A water receptacle is configured to be received within the recess portion of the base and includes a floor and a flange around an opening at the top of the water receptacle. A lid is hingedly attached to the base and is configured to pivot between an open position and a closed position. This lid includes a top wall, an outer depending wall, an inner depending wall in the form of a double wall, and an outlet
(Continued)

pipe. A lid seal is attached to an underside of the top wall of the lid by way of a tongue and groove structure. A catch is located on the base and configured to lock the lid in the closed position.

23 Claims, 50 Drawing Sheets

Related U.S. Application Data continuation of application No. 15/364,874, filed on Nov. 30, 2016, now Pat. No. 10,881,820, which is a continuation of application No. 14/987,275, filed on Jan. 4, 2016, now Pat. No. 9,539,409, which is a continuation of application No. 14/445,190, filed on Jul. 29, 2014, now Pat. No. 9,227,035, which is a continuation of application No. 12/659,963, filed on Mar. 26, 2010, now Pat. No. 10,293,125, which is a continuation of application No. 10/533,940, filed as application No. PCT/AU2004/000810 on Jun. 21, 2004, now Pat. No. 8,006,691.

(51) Int. Cl.

| | |
|---|---|
| *A61M 16/16* | (2006.01) |
| *B01F 3/04* | (2006.01) |
| *A61M 16/08* | (2006.01) |
| *A62B 9/00* | (2006.01) |
| *F04D 17/16* | (2006.01) |
| *F04D 25/06* | (2006.01) |
| *F04D 29/42* | (2006.01) |
| *F04D 29/66* | (2006.01) |
| *B29L 31/00* | (2006.01) |

(52) U.S. Cl.
CPC .... *A61M 16/0051* (2013.01); *A61M 16/0057* (2013.01); *A61M 16/024* (2017.08); *A61M 16/0816* (2013.01); *A61M 16/0875* (2013.01); *A61M 16/105* (2013.01); *A61M 16/109* (2014.02); *A61M 16/16* (2013.01); *A61M 16/162* (2013.01); *B01F 3/0446* (2013.01); *F04D 17/16* (2013.01); *F04D 25/0693* (2013.01); *F04D 29/4206* (2013.01); *F04D 29/664* (2013.01); *A61M 16/107* (2014.02); *A61M 2205/0216* (2013.01); *A61M 2205/123* (2013.01); *A61M 2205/14* (2013.01); *A61M 2205/3303* (2013.01); *A61M 2205/3306* (2013.01); *A61M 2205/3368* (2013.01); *A61M 2205/36* (2013.01); *A61M 2205/42* (2013.01); *A61M 2205/50* (2013.01); *A61M 2205/502* (2013.01); *A61M 2205/52* (2013.01); *A61M 2205/6063* (2013.01); *A61M 2206/16* (2013.01); *A61M 2230/005* (2013.01); *A61M 2230/46* (2013.01); *A62B 9/003* (2013.01); *B01F 2003/04872* (2013.01); *B01F 2215/0091* (2013.01); *B29L 2031/753* (2013.01)

(58) Field of Classification Search
CPC .......... A61M 16/0066; A61M 16/0069; A61M 16/10; A61M 16/1045; A61M 16/1075; A61M 16/109; A61M 16/1095; A61M 16/12; A61M 16/14; A61M 16/16; A61M 16/161; A61M 16/162; A61M 16/164
See application file for complete search history.

(56) References Cited

U.S. PATENT DOCUMENTS

| | | | |
|---|---|---|---|
| 2,220,669 | A | 11/1940 | Allen |
| 2,598,978 | A | 6/1952 | De Martin |
| 2,945,619 | A | 7/1960 | Ballard |
| 3,171,353 | A | 3/1965 | McMahan |
| 3,316,910 | A | 5/1967 | Davis |
| 3,584,401 | A | 6/1971 | Cryer et al. |
| 3,612,710 | A | 10/1971 | Mount |
| 3,620,638 | A | 11/1971 | Kaye et al. |
| 3,690,317 | A | 9/1972 | Millman |
| 3,806,102 | A | 4/1974 | Valenta et al. |
| 3,864,440 | A | 2/1975 | Giocoechea |
| 3,954,920 | A | 5/1976 | Heath |
| 4,037,994 | A | 7/1977 | Bird |
| 4,051,205 | A | 9/1977 | Grant |
| 4,060,576 | A | 11/1977 | Grant |
| 4,098,853 | A | 7/1978 | Brown et al. |
| 4,105,372 | A | 8/1978 | Mishina et al. |
| 4,171,190 | A | 10/1979 | Hudson |
| 4,222,971 | A | 9/1980 | Eilert |
| 4,229,142 | A | 10/1980 | Le Dall et al. |
| 4,237,080 | A | 12/1980 | Elliott |
| 4,243,396 | A | 1/1981 | Cronenberg |
| 4,336,798 | A | 6/1982 | Beran |
| 4,351,327 | A | 9/1982 | Rinne |
| 4,523,896 | A | 6/1985 | Lhenry et al. |
| 4,532,088 | A | 7/1985 | Miller |
| 4,576,616 | A | 3/1986 | Mottram et al. |
| 4,621,632 | A | 11/1986 | Bartels et al. |
| 4,629,590 | A | 12/1986 | Bagwell |
| 4,644,790 | A | 2/1987 | Mizoguchi |
| 4,676,237 | A | 6/1987 | Wood et al. |
| 4,753,758 | A | 6/1988 | Miller |
| 4,767,576 | A | 8/1988 | Bagwell |
| 4,789,388 | A | 12/1988 | Nishibata |
| 4,799,287 | A | 1/1989 | Belanger |
| 4,802,819 | A | 2/1989 | Bevington |
| 4,807,616 | A | 2/1989 | Adahan |
| 4,823,787 | A | 4/1989 | Adahan |
| 4,838,258 | A | 6/1989 | Dryden et al. |
| 4,921,642 | A | 5/1990 | La Torraca |
| 4,926,856 | A | 5/1990 | Cambio et al. |
| 4,941,469 | A | 7/1990 | Adahan |
| 4,943,704 | A | 7/1990 | Rabenau |
| 4,946,348 | A | 8/1990 | Yapp |
| 4,953,546 | A | 9/1990 | Blackmer et al. |
| 4,973,234 | A | 11/1990 | Swenson |
| 5,014,338 | A | 5/1991 | Glucksman |
| 5,061,405 | A | 10/1991 | Stanek et al. |
| 5,080,093 | A | 1/1992 | Raabe |
| 5,086,766 | A | 2/1992 | Beacham |
| 5,097,424 | A | 3/1992 | Ginevri et al. |
| 5,127,800 | A | 7/1992 | Hyll et al. |
| 5,237,987 | A | 8/1993 | Anderson et al. |
| 5,271,391 | A | 12/1993 | Graves |
| 5,329,939 | A | 7/1994 | Howe |
| 5,339,825 | A | 8/1994 | McNaughton et al. |
| 5,391,063 | A | 2/1995 | Hantle et al. |
| 5,443,061 | A | 8/1995 | Champain et al. |
| 5,483,616 | A | 1/1996 | Chiu et al. |
| 5,551,419 | A | 9/1996 | Froehlich et al. |
| 5,558,084 | A | 9/1996 | Daniell et al. |
| 5,564,415 | A | 10/1996 | Dobson et al. |
| 5,573,713 | A | 11/1996 | Tomasiak |
| 5,577,496 | A | 11/1996 | Blackwood et al. |
| 5,598,837 | A | 2/1997 | Sirianne et al. |
| 5,651,775 | A | 7/1997 | Walker et al. |
| 5,637,687 | A | 10/1997 | Dobson et al. |
| 5,673,687 | A | 10/1997 | Dobson et al. |
| 5,682,289 | A | 10/1997 | Schwegler et al. |
| 5,794,219 | A | 8/1998 | Brown |
| 5,822,715 | A | 10/1998 | Worthington et al. |
| 5,828,943 | A | 10/1998 | Brown |
| 5,832,448 | A | 11/1998 | Brown |
| 5,844,862 | A | 12/1998 | Cocatre-Zilgien |
| 5,848,592 | A | 12/1998 | Sibley |

(56) References Cited

U.S. PATENT DOCUMENTS

| | | |
|---|---|---|
| 5,865,171 A | 2/1999 | Cinquin |
| 5,879,163 A | 3/1999 | Brown et al. |
| 5,887,133 A | 3/1999 | Brown et al. |
| 5,888,053 A | 3/1999 | Kobayashi et al. |
| 5,895,595 A | 4/1999 | Haden |
| 5,897,493 A | 4/1999 | Brown |
| 5,899,855 A | 5/1999 | Brown |
| 5,913,310 A | 6/1999 | Brown |
| 5,916,493 A | 6/1999 | Miller et al. |
| 5,918,603 A | 7/1999 | Brown |
| 5,928,177 A | 7/1999 | Brugger et al. |
| 5,933,136 A | 8/1999 | Brown |
| 5,940,801 A | 8/1999 | Brown |
| 5,943,473 A | 8/1999 | Levine |
| 5,951,300 A | 9/1999 | Brown |
| 5,956,501 A | 9/1999 | Brown |
| 6,052,511 A | 4/2000 | Birdsell |
| 6,109,865 A | 8/2000 | Ishikawa |
| 6,129,524 A | 10/2000 | Wollenweber et al. |
| 6,131,571 A | 10/2000 | Lampotang et al. |
| 6,135,432 A | 10/2000 | Hebblewhite et al. |
| 6,158,978 A | 12/2000 | Norbury, Jr. |
| 6,186,140 B1 | 2/2001 | Hoague |
| 6,210,116 B1 | 4/2001 | Kuczaj et al. |
| 6,213,119 B1 | 4/2001 | Brydon et al. |
| 6,216,691 B1 | 4/2001 | Kenyon et al. |
| 6,257,171 B1 | 7/2001 | Rivard |
| 6,275,652 B1 | 8/2001 | Chauviaux |
| 6,314,237 B1 | 11/2001 | Glucksman |
| 6,332,462 B1 | 12/2001 | Krohn |
| 6,349,724 B1 | 2/2002 | Burton et al. |
| D454,393 S | 3/2002 | Lynch et al. |
| 6,397,841 B1 | 6/2002 | Kenyon et al. |
| 6,435,180 B1 | 8/2002 | Hewson et al. |
| 6,471,493 B2 | 10/2002 | Choi et al. |
| D467,335 S | 12/2002 | Lithgow et al. |
| D468,011 S | 12/2002 | Lynch et al. |
| D468,017 S | 12/2002 | McCombs |
| 6,514,053 B2 | 2/2003 | Takura et al. |
| 6,543,449 B1 | 4/2003 | Woodring et al. |
| 6,546,930 B1 | 4/2003 | Emerson et al. |
| 6,554,260 B1 | 4/2003 | Lipscombe et al. |
| 6,604,390 B1 | 8/2003 | Nooner |
| 6,615,444 B2 | 9/2003 | McGill et al. |
| 6,622,724 B1 | 9/2003 | Truitt et al. |
| 6,669,630 B1 | 12/2003 | Joliat et al. |
| 6,672,300 B1 | 1/2004 | Grant |
| 6,678,215 B1 | 1/2004 | Treyz et al. |
| D487,311 S | 3/2004 | Lithgow et al. |
| 6,718,974 B1 | 4/2004 | Moberg |
| D493,520 S | 7/2004 | Bertinetti et al. |
| D493,884 S | 8/2004 | Virr et al. |
| 6,772,999 B2 | 8/2004 | Lipscombe et al. |
| 6,775,882 B2 | 8/2004 | Murphy et al. |
| D498,527 S | 11/2004 | Virr et al. |
| 6,827,340 B2 | 12/2004 | Austin et al. |
| 6,837,260 B1 | 1/2005 | Kuehn |
| 6,874,771 B2 | 4/2005 | Birdsell et al. |
| 6,896,478 B2 | 5/2005 | Botros et al. |
| 6,910,483 B2 | 6/2005 | Daly et al. |
| 6,918,389 B2 | 7/2005 | Seakins et al. |
| 6,935,337 B2 | 8/2005 | Virr et al. |
| 7,056,289 B2 | 6/2006 | Kasper et al. |
| 7,089,930 B2 | 8/2006 | Adams et al. |
| 7,096,864 B1 | 8/2006 | Mayer et al. |
| 7,128,729 B2 | 10/2006 | Duchon et al. |
| 7,137,388 B2 | 11/2006 | Virr et al. |
| 7,614,398 B2 | 11/2009 | Virr et al. |
| 8,006,691 B2 | 8/2011 | Trevor-Wilson |
| 8,020,551 B2 | 9/2011 | Virr |
| 8,028,693 B2 | 10/2011 | Trevor-Wilson |
| 9,038,632 B2 | 5/2015 | Crumblin |
| 9,227,035 B2 | 1/2016 | Crumblin et al. |
| 9,539,409 B2 | 1/2017 | Crumblin et al. |
| RE46,543 E | 9/2017 | Trevor-Wilson |
| 10,201,676 B2 | 2/2019 | Lithgow |
| 10,293,125 B2 | 5/2019 | Crumblin et al. |
| 2001/0050080 A1 | 12/2001 | Seakins et al. |
| 2002/0020930 A1 | 2/2002 | Austin et al. |
| 2002/0022973 A1 | 2/2002 | Sun et al. |
| 2002/0056453 A1 | 5/2002 | Klopp |
| 2002/0159897 A1 | 10/2002 | Kegg et al. |
| 2003/0062045 A1 | 4/2003 | Woodring et al. |
| 2003/0065308 A1 | 4/2003 | Lebel et al. |
| 2003/0066526 A1 | 4/2003 | Thudor et al. |
| 2003/0076745 A1 | 4/2003 | Chapman |
| 2003/0084900 A1 | 5/2003 | LeClerc et al. |
| 2003/0115085 A1 | 6/2003 | Satoh |
| 2003/0187525 A1 | 10/2003 | Mann et al. |
| 2003/0236450 A1 | 12/2003 | Kocinski |
| 2004/0035422 A1 | 2/2004 | Truitt et al. |
| 2005/0005937 A1 | 1/2005 | Farrugia et al. |
| 2005/0103339 A1 | 5/2005 | Daly et al. |
| 2005/0217673 A1 | 10/2005 | Daly et al. |
| 2006/0191531 A1 | 8/2006 | Mayer |
| 2006/0237005 A1 | 10/2006 | Virr et al. |
| 2007/0036662 A1 | 2/2007 | Pensola et al. |
| 2007/0134085 A1 | 6/2007 | Daly et al. |
| 2008/0072900 A1 | 3/2008 | Kenyon et al. |
| 2010/0192094 A1 | 7/2010 | Jeha |
| 2016/0114122 A1 | 4/2016 | Crumblin et al. |
| 2017/0087327 A1 | 3/2017 | Crumblin et al. |

FOREIGN PATENT DOCUMENTS

| | | |
|---|---|---|
| CN | 1210020 | 3/1999 |
| CN | 1314192 | 9/2001 |
| DE | 275612 | 1/1913 |
| DE | 275612 | 6/1914 |
| DE | 30 05 094 | 8/1981 |
| DE | 3623162 A1 | 7/1986 |
| DE | 3642637 | 6/1988 |
| DE | 9014848.7 | 3/1991 |
| DE | 4138098 C2 | 11/1991 |
| DE | 4244493 A1 | 7/1993 |
| DE | 93 17 450 | 6/1994 |
| DE | 3789221 | 8/1994 |
| DE | 94 09 231 U1 | 12/1994 |
| DE | 9409231.1 | 12/1994 |
| DE | 19515739 C2 | 5/1995 |
| DE | 19630466 | 2/1998 |
| DE | 29817685 | 10/1998 |
| DE | 69409024 T2 | 11/1998 |
| DE | 19752672 | 3/1999 |
| DE | 29817685 U1 | 6/1999 |
| DE | 299 09 611 U1 | 10/1999 |
| DE | 29909611 | 10/1999 |
| DE | 29909611 U1 | 10/1999 |
| DE | 200 13 392 U1 | 10/2000 |
| DE | 100 21 782 | 11/2000 |
| DE | 10016005 | 12/2001 |
| DE | 20213232 | 4/2003 |
| DE | 102005007773 A1 | 9/2005 |
| EP | 0201985 | 11/1986 |
| EP | 0274996 A2 | 7/1988 |
| EP | 0274996 B1 | 7/1988 |
| EP | 3823242 A1 | 2/1990 |
| EP | 0589 429 | 3/1994 |
| EP | 0 760 247 | 3/1997 |
| EP | 0845277 A2 | 6/1998 |
| EP | 0 893 750 | 1/1999 |
| EP | 0903160 A1 | 3/1999 |
| EP | 1 002 552 A2 | 5/2000 |
| EP | 1023912 A2 | 8/2000 |
| EP | 1 055 431 | 11/2000 |
| EP | 1318307 | 6/2003 |
| EP | 1 374 938 | 1/2004 |
| FR | 2 714 985 | 7/1995 |
| GB | 2069607 A | 8/1981 |
| GB | 2177006 A | 1/1987 |
| GB | 2192136 A | 1/1988 |
| GB | 2293325 | 3/1996 |
| GB | 2353904 A | 3/2001 |
| JP | 58-036560 | 3/1983 |

(56) References Cited

FOREIGN PATENT DOCUMENTS

| | | |
|---|---|---|
| JP | 61-179161 | 8/1986 |
| JP | 64-500088 | 1/1989 |
| JP | 2-19168 | 1/1990 |
| JP | 4-69434 | 3/1992 |
| JP | 05-104681 | 4/1993 |
| JP | 5-285220 | 11/1993 |
| JP | 6-26894 | 4/1994 |
| JP | 06-190928 | 7/1994 |
| JP | 7-145795 A | 6/1995 |
| JP | 07-03195 | 7/1995 |
| JP | 08-178781 | 7/1996 |
| JP | 09-103490 | 4/1997 |
| JP | 10-122611 A | 5/1998 |
| JP | 11-398 A | 1/1999 |
| JP | 2000-237316 | 9/2000 |
| JP | 2001-61814 | 3/2001 |
| JP | 2001-160102 | 6/2001 |
| JP | 2001-516277 | 9/2001 |
| JP | 2002-206498 A | 7/2002 |
| JP | 2002-248167 | 9/2002 |
| JP | 2002-253672 | 9/2002 |
| JP | 2002-306601 | 10/2002 |
| JP | 2003-506161 | 2/2003 |
| JP | 2003-527160 | 9/2003 |
| JP | 2004-532666 | 10/2004 |
| WO | 88/00068 | 1/1988 |
| WO | WO 93/05451 | 3/1993 |
| WO | WO 95/15778 | 6/1995 |
| WO | WO 97/32619 | 9/1997 |
| WO | WO 98/31937 | 7/1998 |
| WO | WO 98/41306 | 9/1998 |
| WO | WO 98/57691 | 12/1998 |
| WO | WO 99/13932 | 3/1999 |
| WO | WO 99/22794 | 5/1999 |
| WO | WO 99/64747 | 12/1999 |
| WO | 2000021602 | 4/2000 |
| WO | WO 00/27457 | 5/2000 |
| WO | WO 00/32261 | 6/2000 |
| WO | 2000038771 | 7/2000 |
| WO | WO 00/42324 | 7/2000 |
| WO | WO 01/10489 A2 | 2/2001 |
| WO | WO 01/32069 | 5/2001 |
| WO | WO 01/73653 A1 | 10/2001 |
| WO | WO 02/02169 A1 | 1/2002 |
| WO | 02/20075 | 3/2002 |
| WO | WO 02/053217 | 7/2002 |
| WO | 2002066107 | 8/2002 |
| WO | WO 02/066105 | 8/2002 |
| WO | WO 02/066107 A1 | 8/2002 |
| WO | WO 03/090827 | 11/2003 |
| WO | 2004/112873 | 12/2004 |
| WO | WO 2005/011556 | 2/2005 |
| WO | WO 2007/019628 | 2/2007 |
| WO | WO 2009/059359 | 5/2009 |
| WO | WO 2009/156921 A1 | 12/2009 |
| WO | WO 2010/092496 | 8/2010 |

OTHER PUBLICATIONS

Jan. 23, 2019 Notice of Opposition to Grant of Patent Filed in New Zealand Patent Application No. 728764.
USPTO File Extract for U.S. Pat. No. 7,096,864.
Sullivan Humidaire User Manual, ResMed Ltd., 2001.
HC200 Series CPAP User Manual, Fisher & Paykel Healthcare, Rev C, Jun. 1999.
ResMed S7 Elite AutoSet Spirit, Promotional Document, ResMed Ltd., 2002.
Office Action dated Jun. 8, 2016 issued in European Application No. 14200112.2 (7 pages).
Decision of Rejection dated Apr. 25, 2016 issued in Japanese Application No. 2014-006622 with English translation (5 pages).
Office Action dated May 26, 2016 issued in U.S. Appl. No. 15/054,820 (37 pages).
Office Action dated Jun. 2, 2016 issued in U.S. Appl. No. 13/916,930 (28 pages).
Office Action dated Jun. 7, 2016 issued in U.S. Appl. No. 15/042,474 (32 pages).
Notice of Reasons for Rejection dated Apr. 4, 2016 issued in Japanese Application No. 2015-059122 with English translation (6 pages).
Notification of the First Office Action dated Mar. 25, 2016 issued in Chinese Application No. 201410559916.0 with English translation (17 pages).
Chinese Office Action for co-pending Chinese Application No. 200480017315.1 and English Translation, dated Oct. 9, 2009, 14 pages.
Supplementary European Search Report for Co-pending European Application No. 04737434.3, dated Oct. 15, 2009, 4 pages.
International Search Report of PCT/AU2004/000810 dated Oct. 1, 2004.
Office Action and English Translation from copending JP Appln. No. 2006-515549, dated Jan. 5, 2010, 11 pages.
Office Action and English Translation from copending JP Appln. No. 2006-515549, dated Nov. 2, 2010, 7 pages.
Office Action from corresponding European Appln. No. 04737434.3, dated Apr. 14, 2010, 8 pages.
Office Action from corresponding European Appln. No. 04737434.3, dated Apr. 26, 2010, 8 pages.
Breas Medical AB "iSleep@ 20" Brochure, Dec. 2007, 2 pages.
Fisher & Paykel Healthcare "SleepStyle™ 200 CPAP Series" Specification Sheet, 2005, 4 pages.
Fisher & Paykel Healthcare "SleepStyle™ 600 CPAP Series" Specification Sheet, 2005, 4 pages.
Fisher & Paykel Healthcare Two Easy Steps to Comfort, Humidification and Nasal CPAP Therapy, Aug. 1995, 4 pages.
Hoffrichter GmbH "VECTOR therapy in perfection" Brochure, 2002, 2 pages.
MAP Medizin-Technologie GmbH "minni Max nCPAP®, The respiratory therapy device with-out an integrated humidifier", Dec. 2003, 17 pages.
MAP Medizintechnik fuer Arzt und Patient "max II nCPAP moritz II biLevel—The gentle therapy for sleep-related breathing disorders" Brochure, 2000, 4 pages.
Respironics "System One Heated Humidifier User Manual", May 2009, 20 pages.
ResMed, "The Sullivan® Humid Aire™", 1997, 1 page.
J. H. Emerson Co., Cough Assist, "Non-Invasive Removal of Bronchial Secretions," 2 pages.
Examination Report for copending European Appln No. 04737434.3, dated Apr. 14, 2010, 8 pages.
Examination Report for copending European Appln No. 04737434.3, dated Apr. 26, 2010, 8 pages.
German Patient Manual for Hoffrichter/Sandmann CPAP Respirator—Perfect CPAP Therapy, 30 pages plus Translation Verification Certificate, no date, but admitted as prior art prior to critical date.
Kenyon et al., U.S. Appl. No. 12/900,008, filed Oct. 7, 2010.
Kenyon et al., U.S. Appl. No. 12/900,781, filed Oct. 8, 2010.
MAP Medizintechnik, "minni Max nCPAP@" brochure, 12 pages, Mar. 2005.
Hoffrichter Medizintechnik GmbH, "Sandmann CPAP—Therapie in Perfektion" brochure, 32 pages, Mar. 1998.
Madaus Schwarzer Medizintechnik, "New Approaches in Diagnosis and Therapy—Moritz biLevel User Manual", May 1994, 38 pages.
MAP Medizintechnik, "Moritz II biLEVEL®—The gentle therapy for sleep-related breathing disorders" brochure, 6 pages, Jan. 2001.
Photos of MAP Humidifier and Tub, 2 pages and cover sheet, undated.
Madaus Schwarzer Medizintechnik, "New Approaches in Diagnosis and Therapy—Max nCPAP User Manual", Mar. 1994, 38 pages.
ResMed "Sullivan® HumidAire® User's Instructions", 8 pages, undated.
MAP Medizin-Technologie GmbH, Moritz® S/Moritz® ST—Sailing toward therapeutic success. . . , 4 pages, undated.
Hoffrichter "Vector CPAP—Therapy With Technical Mastery", 4 pages, Oct. 1998.

(56) References Cited

OTHER PUBLICATIONS

Fischer & Paykel, "Two Easy Steps to Comfort", 4 pages, Aug. 1995.
Australian Office Action for corresponding AU Appln. No. 2004248855, dated Nov. 6, 2009, 5 pages.
Australian Office Action for corresponding AU Appln. No. 2010201899, dated Jun. 10, 2010, 5 pages.
Examiner Summary from Meeting corresponding AU Appln. No. 2010201899, dated Aug. 12, 2010, 3 pages.
Japanese Office Action and its English Translation for corresponding Japanese Appln. No. 2010-224861, dated Jan. 18, 2011 (7 pages).
German Patient Manual for Hoffrichter/Sandmann CPAP Respirator—Perfect CPAP Therapy, 30 pages plus Translation Verification Certificate, no date, but admitted as prior to critical date.
Japanese Office Action and its English Translation for Corresponding Japanese Appln. No. 2010-224862, dated Jan. 4, 2011 (9 pages).
Japanese Office Action and its English Translation for Corresponding Japanese Appln. No. 2011-007671, dated Mar. 1, 2011 (6 pages).
Office Action dated Jan. 22, 2013 in corresponding Japanese Application No. 2011-201622.
Office Action dated Mar. 7, 2013 in corresponding New Zealand Application No. 607671.
Office Action dated Mar. 7, 2013 in corresponding New Zealand Application No. 596207.
Australian Office Action for corresponding Australian Appln. No. 2010257238, dated Mar. 10, 2011 (2 pages).
Office Action and English Translation for corresponding Japanese Application No. 2006-515549, dated Mar. 15, 2011, 4 pages.
Proceedings Correspondence dated Mar. 1, 2012 in corresponding New Zealand Patent No. 567371.
Search Report dated Jun. 6, 2013 in corresponding European Application No. 11175449.5.
Japanese Office Action (Decision of Rejection) for Application No. 2011-201622 dated Aug. 13, 2013 w/ English Translation (7 pages).
Office Action dated Aug. 24, 2012 in corresponding Australian Application No. 2010257238.
Office Action dated Aug. 7, 2012 in corresponding Japanese Application No. 2010-153008 (with translation).
Office Action of Parent U.S. Appl. No. 10/533,940, filed Dec. 29, 2006, dated Oct. 12, 2010, 10 pages.
Notice of Reasons for Rejection dated Dec. 22, 2014 issued in Japanese Application No. 2014-0006622 with English translation (6 pages).
Notice of Allowance dated Jan. 7, 2015 issued in U.S. Appl. No. 14/445,143 (32 pages).
Notice of Allowance dated Jan. 13, 2015 issued in U.S. Appl. No. 14/445,152 (35 pages).
Notification of Second Office Action dated Dec. 24, 2014 issued in Chinese Application No. 201210297972.2 with English-language translation (14 pages).
Office Action dated Feb. 25, 2015 issued in U.S. Appl. No. 12/659,963 citing U.S. Pat. No. 6,000,396 and U.S. Pat. No. 5,645,531 (99 pages).
First Examination Report dated Aug. 28, 2015 issued in related New Zealand Application No. 710686 (2 pages).
Fisher & Paykel Healthcare, "HC200 Series Nasal CPAP Blower & Heated Humidifier User's Manual", 1998, 17 pages.
Notification of the Second Office Action dated Mar. 17, 2016 issued in Chinese Application No. 201410017494.4 with English translation (12 pages).

BREATHABLE GAS APPARATUS WITH HUMIDIFIER

CROSS-REFERENCES TO RELATED APPLICATIONS

This application is a continuation of U.S. application Ser. No. 17/102,756, filed Nov. 24, 2020, which is a continuation of U.S. application Ser. No. 15/364,874, filed Nov. 30, 2016, now U.S. Pat. No. 10,881,820, which is a continuation of U.S. application Ser. No. 14/987,275, filed Jan. 4, 2016, now U.S. Pat. No. 9,539,409, which is a continuation of U.S. application Ser. No. 14/445,190, filed Jul. 29, 2014, now U.S. Pat. No. 9,227,035, which is a continuation of U.S. application Ser. No. 12/659,963 filed Mar. 26, 2010, now pending, which is a continuation of U.S. application Ser. No. 10/533,940, filed May 4, 2005, now U.S. Pat. No. 8,006,691, which is a national stage application of PCT/AU04/00810, filed Jun. 21, 2004 in English, which claims the benefit of Australian Application No. 2003903139, filed Jun. 20, 2003, Australian Application No. 2003905136, filed Sep. 22, 2003, and Australian Application No. 2004901008, filed Feb. 27, 2004, each of which is incorporated herein by reference in its entirety.

BACKGROUND OF THE INVENTION

This invention relates to breathable gas supply apparatus, and particularly but not exclusively to such apparatus for use in Continuous Positive Airways Pressure (CPAP) treatment of conditions such as Obstructive Sleep Apnea. It will be described herein in its application to CPAP treatment apparatus, but it is to be understood that the features of the invention will have application to other fields of application, such as mechanical ventilation and assisted respiration.

BRIEF SUMMARY OF THE INVENTION

The advantages of incorporating humidification of the air supply to a patient are known, and CPAP machines are known which incorporate humidifying devices. One of the objects of the invention is to provide a simple and compact breathable gas supply apparatus incorporating a humidifier which is simple and economic in its construction, compact, and easy to use. Other objects and advantages of the invention will be described throughout the specification.

It is to be understood that apparatus described herein contains a number of advances on the prior art, many of which independent inventions, although they contribute together to the realisation of the general object expressed above.

The apparatus described herein incorporates novel aspects of architecture which contribute to a reduction in size compared with known units having similar performance. Techniques for noise reduction and damping are described which enable such a smaller machine to have noise performance which is at least as good as known larger machines.

The apparatus described achieves full integration of the humidifier with the flow generator, in the sense that air flow, electrical and, if required, data connection between the flow generator and the humidifier are provided automatically upon the physical engagement of the two devices, without the need for any other process of interconnection.

In such an integrated device, provisions to guard against flowback of water from the humidifier tank to the flow generator are important, and novel sealing arrangements, and novel arrangements for minimising the occurrence of flowback while at the same time improving the uptake of water vapour in the humidifier are also described. The humidifier is readily detached and replaced on the machine, and has very few parts to be disassembled during cleaning.

Also described herein are improved, modular, devices for enabling data connection with the apparatus, including the connection of data storage devices such as memory cards, smart cards, communication ports and the like to be selectively attached by the user or by medical personnel.

The various aspects of the invention will now be described with reference to the accompanying illustrations, which show a presently proposed embodiment.

DETAILED DESCRIPTION OF THE INVENTION

Figure 1:
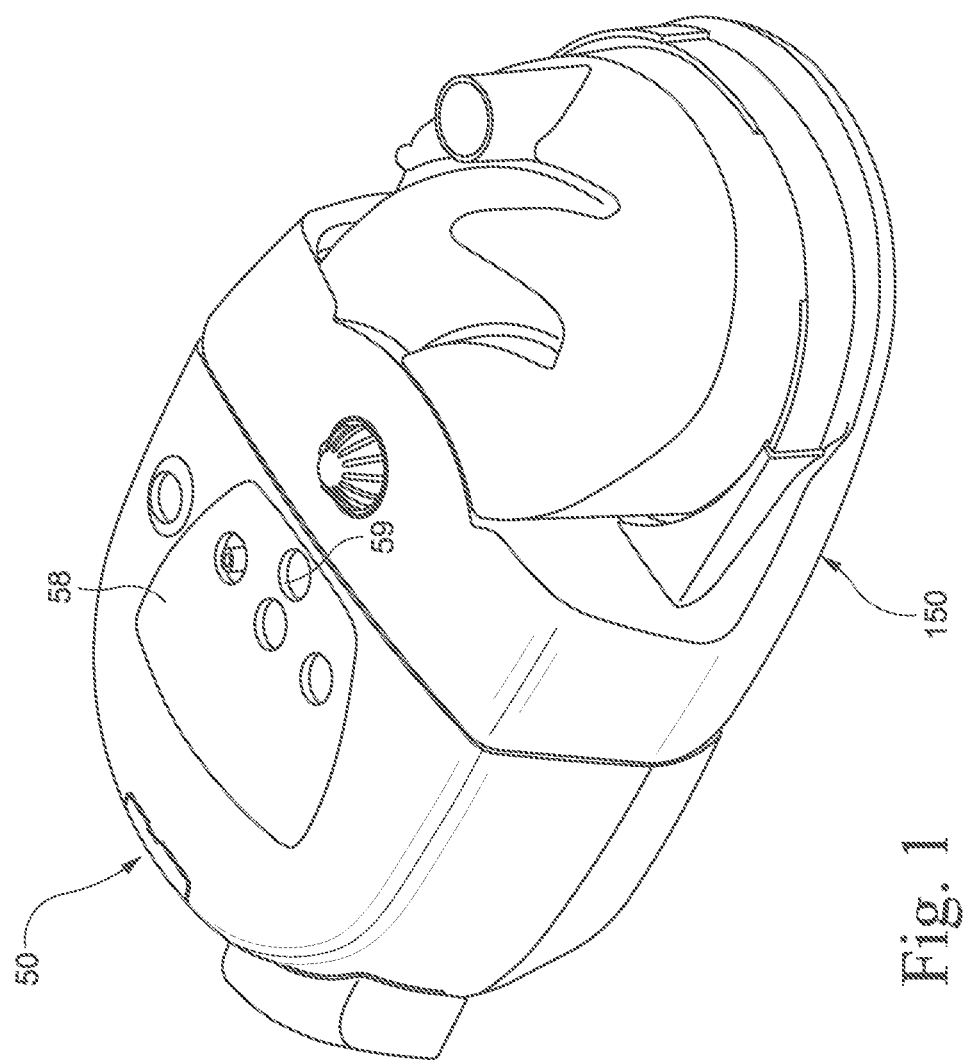
FIG. 1 is a general view of breathable gas apparatus embodying the various features of the invention.
Figure 2:
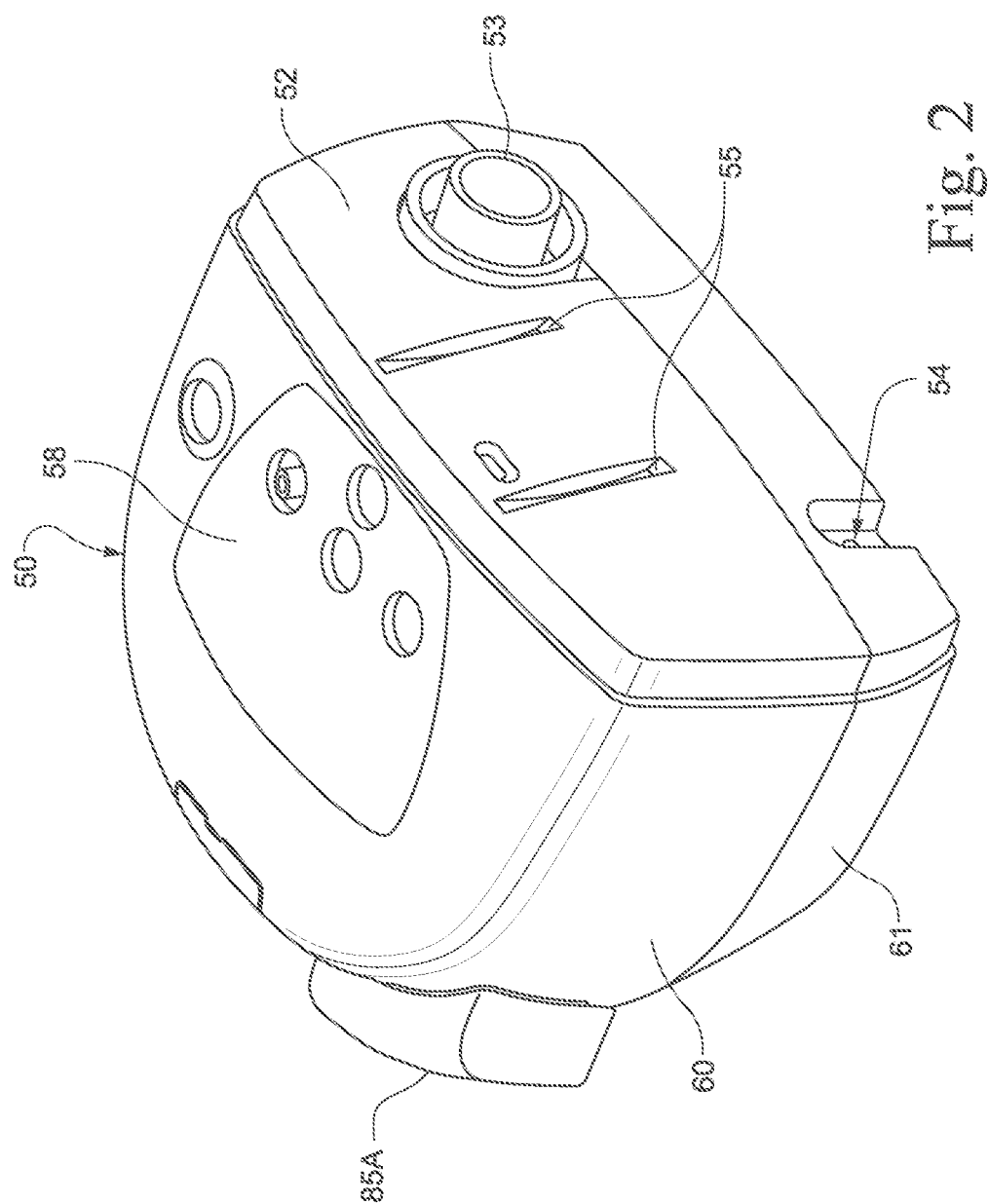
FIG. 2 shows the flow generator of the apparatus.

The illustrated apparatus comprises a flow generator 50 and a humidifier 150, shown in their assembled condition in FIG. 1. As shown in FIG. 2, the flow generator engages with the separable humidifier at an engagement face 52, from which protrudes an air connector 53 for the delivery of air from the fan to the humidifier container, and electrical connectors 54 for the delivery of power to the humidifier heater described below.

Figure 5:
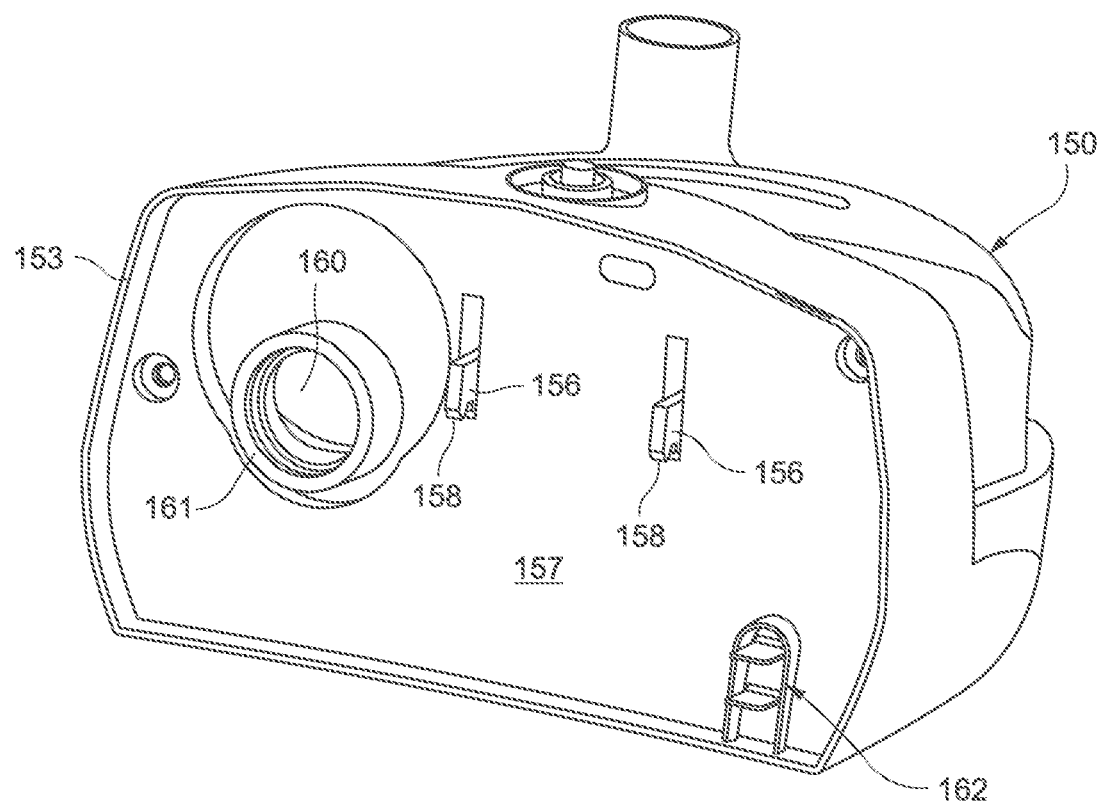
FIG. 5 is a rear view of the humidifier.

The face 52 also carries a pair of slots 55 which are engaged by corresponding tongues 156 provided on the humidifier engagement face 157 (FIG. 5) by which the flow generator 50 and humidifier 150 are connected together, as will be described in more detail below.

Externally, the flow generator 50 is also provided with an LCD screen 58 and associated keys 59 by which the user can set the operating parameters of the unit.

The flow generator 50 has an external case of rigid plastics material moulded in two parts, a top case 60 and a bottom case 61. The lower edge of the top case 60 is stepped and flanged at 62 to mate with the periphery of the bottom case 61. Overmoulded with the rigid plastics body of the bottom case 61 is a rubber sealing flange 63, which locates between and seals against the cases 60 and 61 on the one hand, and the outer surface of a chassis 64 described further below.

Formed in the bottom case 61 by walls which join the outer wall of the case are the lower portions 65 and 67 of, respectively, a power supply cavity and a resonator cavity. The upper portions 66 and 68 of these cavities are formed in the chassis 64, described below.

The chassis 64 is formed with a peripheral wall 69 flanged around its lower edge to engage with the inner periphery of the overmoulded sealing flange 63. The chassis 64 includes a downwardly extending fan cavity 70 in which is mounted the fan 90 described below. This cavity 70 is formed by moulded side walls 71 and base 72, which are formed by moulding thermoplastic around an inserted stainless steel liner 73. The fan cavity 70 opens to the upper surface of the chassis 64 to enable insertion of the fan 90, this opening being closed by a lid 74. Like the cavity 70, the lid 74 has an imbedded stainless steel plate insert moulded within a thermoplastics material, and at its edges the lid is provided with co-molded elastomer sealing edges. The formation of the cavity 70 by insert moulding from differing materials provides very effective acoustic damping, as does the combination by co-moulding of the hard and soft plastics described already and further described below. In this aspect of the present invention, the use of co-moulding or overmoulding in the combination of materials of different, preferably widely different, stiffness and different, preferably widely different, density has been found to be particularly advantageous in providing acoustic damping.

The upper portion 66 of the power supply cavity is formed by a side wall 75 extending downwardly from the roof of the chassis 64, which sealingly engages the opposed wall of the lower portion 65 of this cavity. Preferably, the lower wall is provided for this purpose with a co-moulded or overmoulded rubber sealing flange 63 similar to the flange. The power supply compartment is thus sealed against the ingress of moisture from the interior of the unit in the case of backflow from the humidifier. Similarly, the air path is sealed from the power supply compartment. The interior is at the same time acoustically sealed from the power supply cavity, which may not be completely sealed from the exterior, due to the necessity of providing mains power input and low voltage power output to the humidifier, via connectors 54 mounted in apertures 78 and 80 respectively in the rear and front walls of the cavity, and if necessary the venting of the compartment to outside air for cooling.

Supported on the top of the chassis 64, in the space formed between the chassis and the top of the top case 60 is a printed circuit board 81 carrying the electronic control components of the unit. At the rear of the board 81 an edge connector 82 and a sliding connector are accessible from a connector aperture 83 in the rear of the top case 60, providing for modular connector arrangements to be described in more detail below.

Also provided in the rear wall of the top case is an air inlet 84, and this communicates with an air inlet passage 85 formed in the roof of the upper portion 66 of the power supply cavity, this passage in turn opening through the inner side wall of that cavity at 87 to the air space surrounding the fan cavity 70 in the interior of the unit. Air drawn into the unit by the fan will thus pass over the roof of the power supply and thereby assist in the dissipation of heat generated by the power supply.

Figure 6:
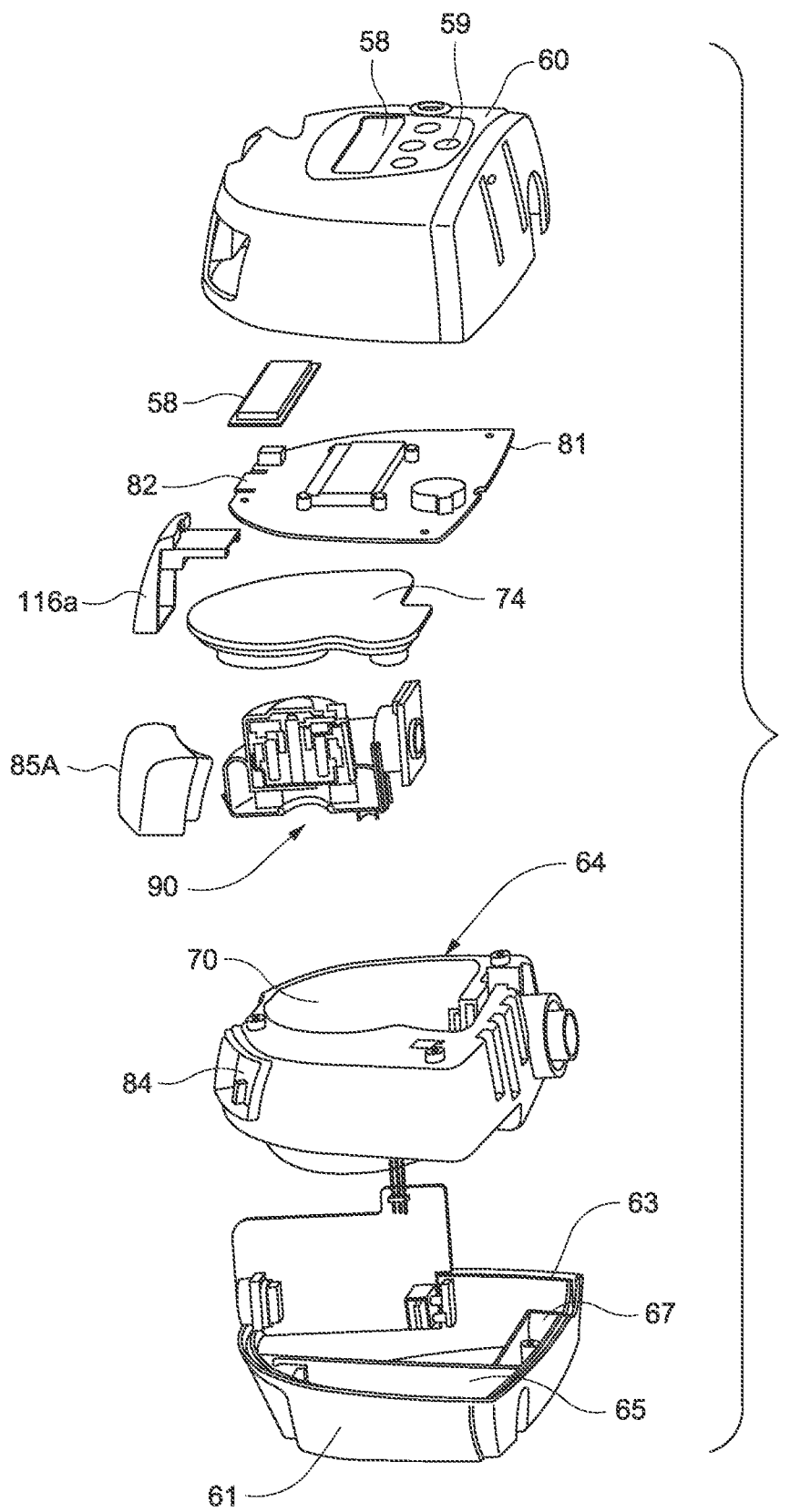
FIG. 6 is an exploded view of components of the flow generator.
Figure 7:
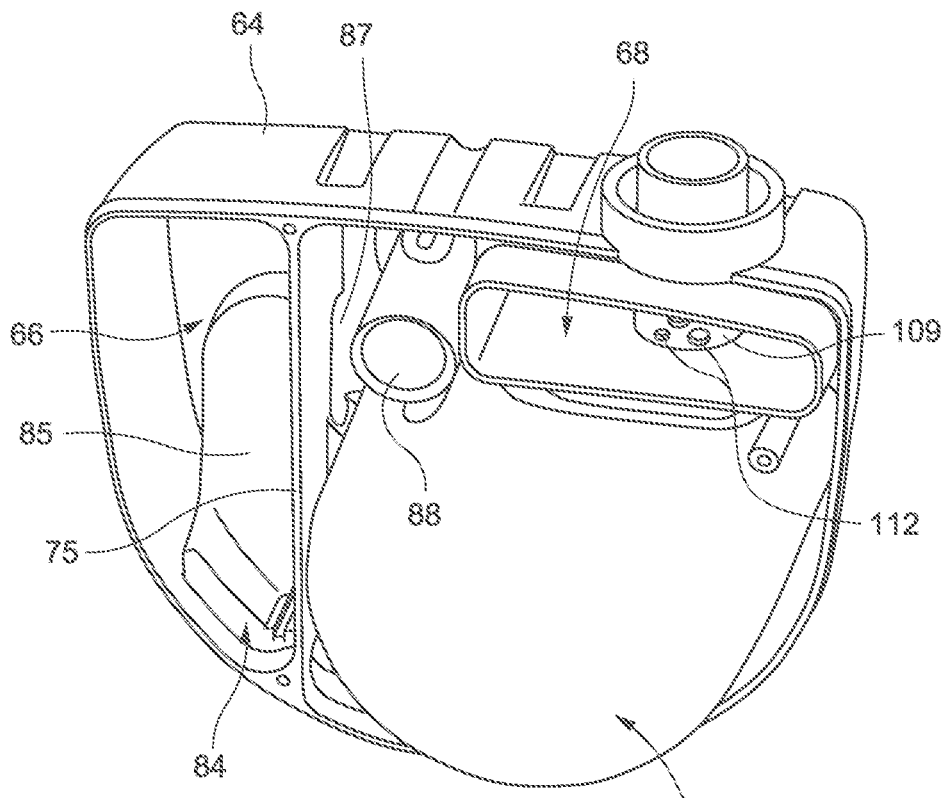
FIG. 7 is an underneath view of a chassis forming part of the flow generator.
Figure 8:
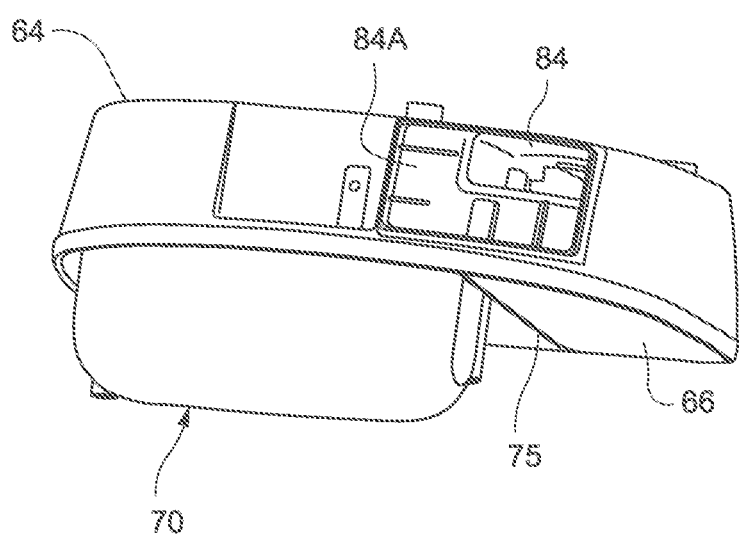
FIG. 8 is a rear view of the chassis.

A removable air filter body 85A containing a replaceable filter element attaches to the inlet 84, as shown in FIGS. 2 and 6.

From the air space surrounding the fan cavity 70, inlet air passes to the fan cavity via an inlet tube 88 depending from a horizontal extension of the side wall 71 of the fan cavity.

The fan cavity and the space surrounding it and enclosed by the upper and lower cases form a pair of serially connected volume mufflers, and the dimensions of the inlet tube 88 and the air inlet passage 85 are chosen to optimise the noise attenuation produced by these mufflers, within the constraint of avoiding unacceptable air flow restriction.

Figure 9:
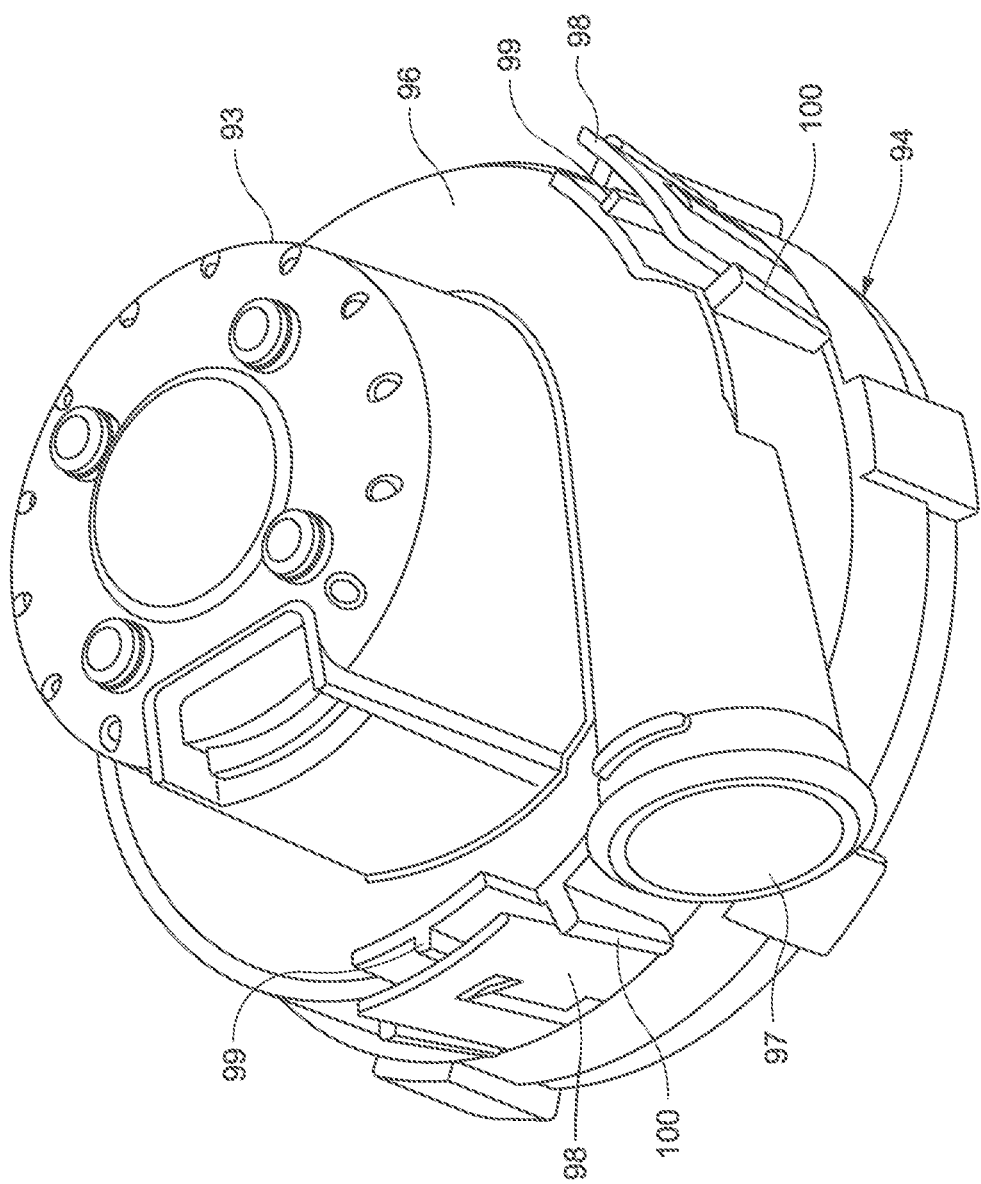
FIG. 9 is a general view of a fan forming part of the flow generator.
Figure 10:
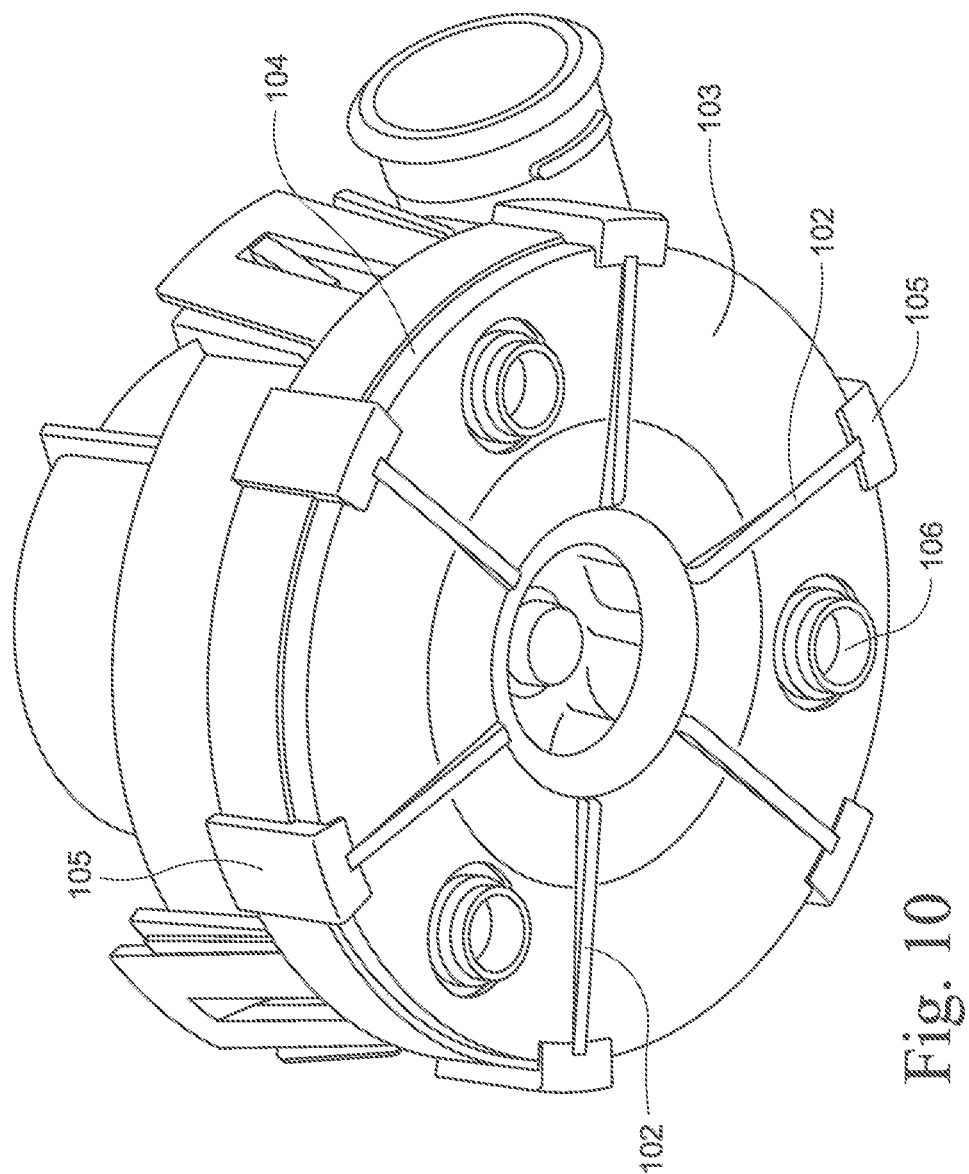
FIG. 10 is an underneath view of the fan.
Figure 11:
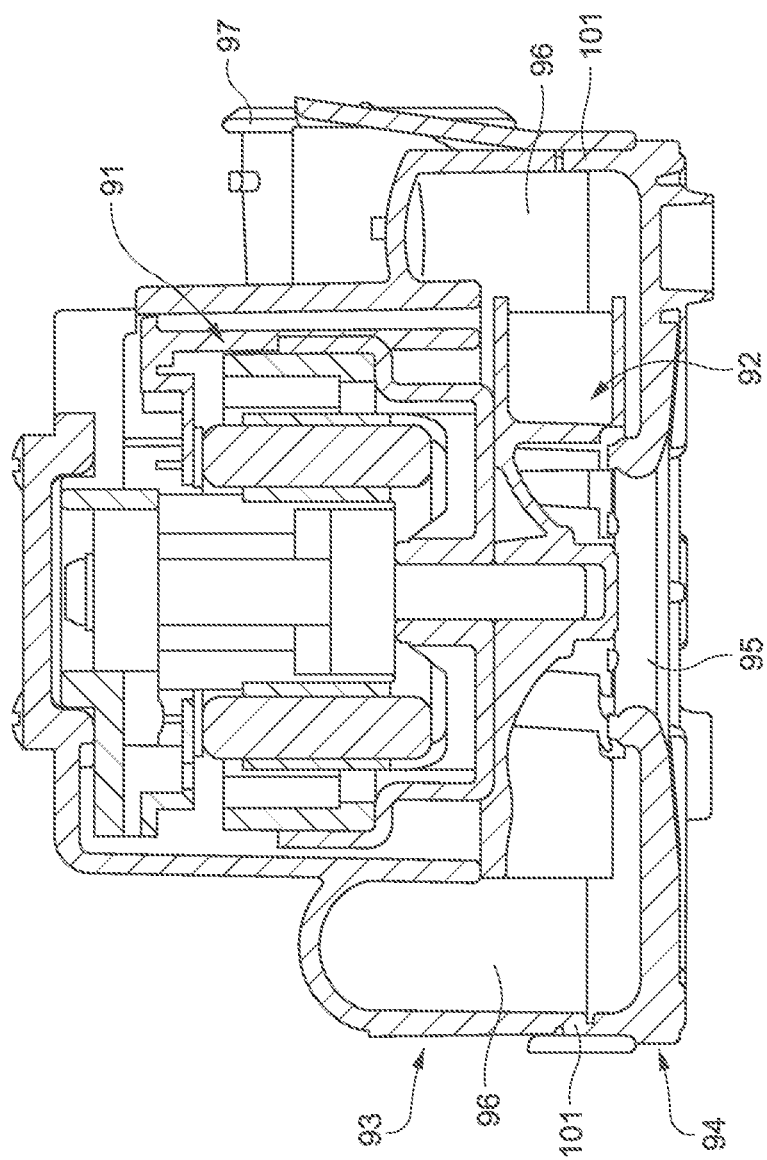
FIG. 11 is a cross-sectional view of the fan.

It will now be convenient to describe the features of the fan, which are shown in FIGS. 9 to 11.

The fan 90 comprises a motor 91, preferably brushless DC motor, provided with a coaxial impeller 92, mounted vertically within a fan housing consisting of a cover 93 and a base 94. An air inlet 95 is provided in the floor of the base 94 on the impeller axis, and cavities in the cover and base form a volute 96 which leads from the impeller to an air outlet 97. The cover and base 93 and 94 are joined by means of slotted tabs 98 which extend upwardly from the base to snap over stepped ribs 99, the tabs 98 being further located by fitting between parallel ribs on the cover 93. The joint between the cover 93 and the base 94 is sealed by an elastomeric sealing ring 101.

The bottom surface of the fan housing base 94 is provided with radial stiffening ribs 102, and overmoulded to the base 94 is an elastomer damping member 103 which covers that bottom surface between the ribs 102, and extends around the edge of the base by a flange portion 104 and peripherally spaced tabs 105. By overmoulding to the rigid plastic base 94 an elastomer of much lower stiffness and much lower density substantial acoustical damping is provided to the fan housing.

Moulded integrally with the rigid plastics portion of the fan housing base are feet 106 which extend through the overmoulded elastomer damping member 103 to receive helical mounting springs (not shown) by which the fan is mounted on the base 72 of the fan cavity.

The degree of size reduction which is an objective of the present invention requires great care to be taken to minimise the transmission of noise and vibration, particularly from the motor and the impeller of the fan 90. The mounting springs are therefore chosen to ensure minimal transmission of the vibration frequencies encountered during operation. This is achieved by choosing the springs with reference to the mass of the fan 90, such that the natural frequency of the system comprising the springs and the fan is at least approximately one tenth of the vibration frequency encountered when the motor is running at its lowest operating speed.

The air outlet 97, upon the introduction of the fan into the fan cavity, is connected by means of a thermoplastic elastomer coupling member with an air outlet passage 109 which extends from the side wall of the fan cavity to a connecting nozzle 110 extending through an aperture 111 provided for this purpose in the front face of the flow generator.

The fan 90 therefore floats within its cavity 70 in the chassis 64 with minimum acoustic coupling to the remainder of the flow generator. The characteristics of the mounting springs and the coupling member are chosen to minimise the transmission of characteristic vibration frequencies of the fan.

The air outlet passage 109 is formed in the roof of the upper portion 68 of the resonator cavity. Holes 112 communicating with the resonator cavity are provided in the floor of the passage 109 where it crosses this cavity, which acts in the manner of a Helmholtz resonator. By adjusting the dimensions and number of the holes 112, the frequency response of the resonator can be adjusted for optimum noise cancellation. If desired, a second Helmholtz resonator cavity can be provided opposite the upper portion 68 of the resonator cavity, if the dimensions of the top case 60 allow this.

The novel use of Helmholtz resonators for noise attenuation contributes to the success in achieving significant size reduction in the flow generator of the present invention.

Figure 12:
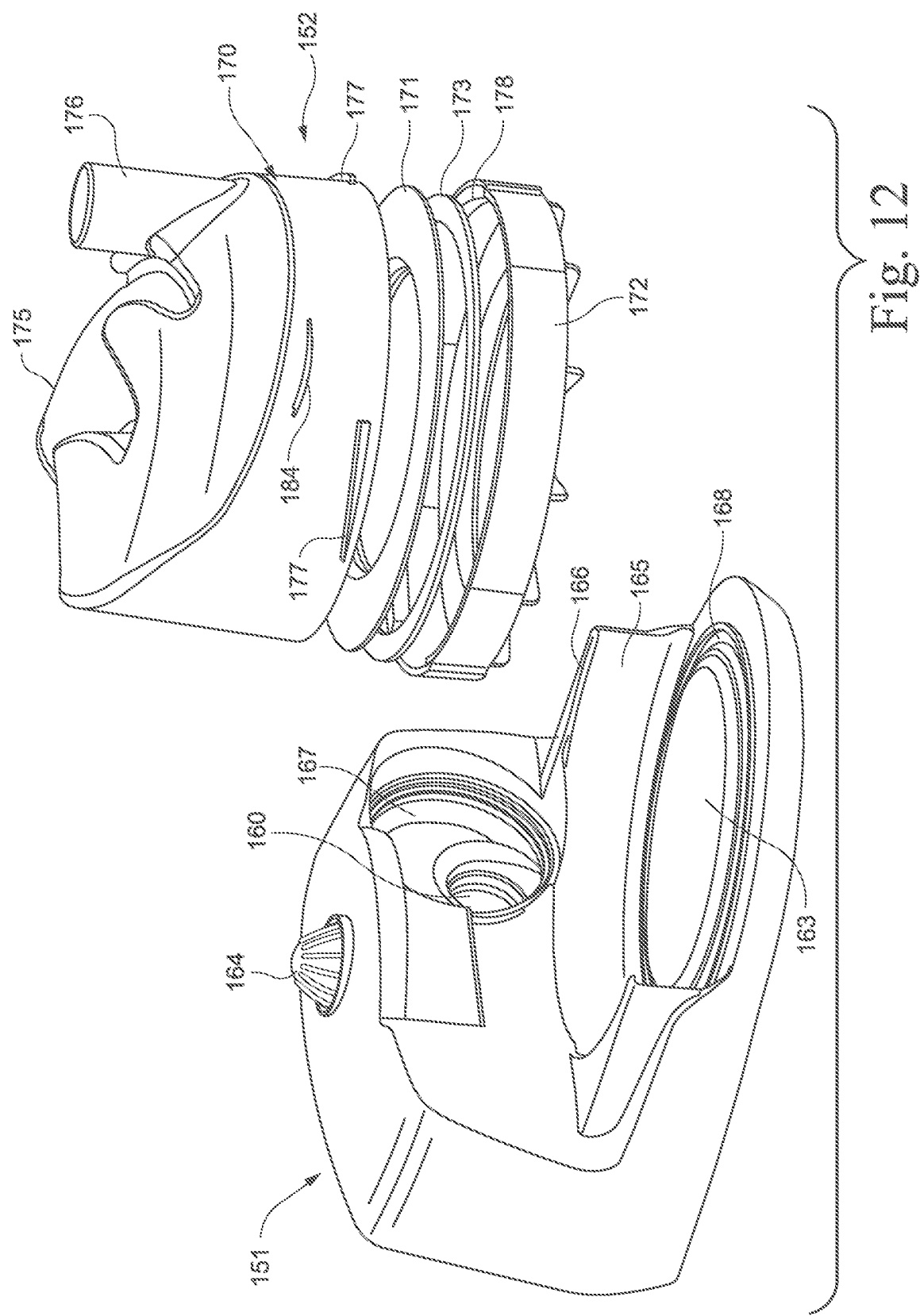
FIG. 12 shows the humidifier in partly disassembled state.
Figure 13:
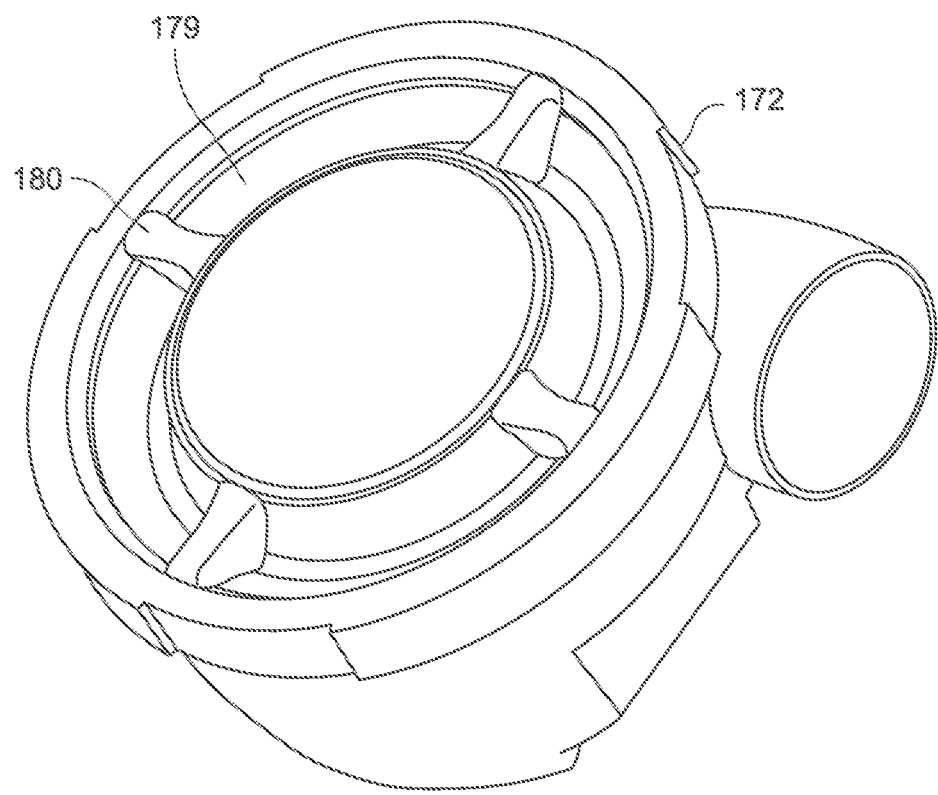
FIG. 13 is an underneath view of the tank of the humidifier.

As shown in FIG. 12, the humidifier 150 comprises a base unit 151 designed for simple attachment to and detachment from the flow generator 50, and a tank 152 which is similarly attachable to and detachable from the base unit.

The rear face of the base unit 151 has a peripheral flange 153 which seats in a corresponding peripheral recess 113 surrounding the front face of the flow generator 50 when the two units are brought together by linear movement towards each other. The tongues 156 are moveable vertically and resiliently urged downwardly, so that these tongues engage in the slots 55 and snap home to engage the two units by means of the downwardly extending fingers 158 at the ends of the tongues.

An air flow passage 160 passes through the humidifier engagement face 157 and opens to the front wall of the base unit. This passage is surrounded at the rear wall with a cylindrical connecting portion 161 which receives the nozzle 110 of the flow generator upon engagement of the two units. The inner surface of the portion 161 is provided with a sealing device such as a layer of elastomer or other soft resilient material.

The rear face of the base unit also carries a connector 162, in this embodiment a pair of flat male blade connectors, for engagement with a mating connector on the front face of the flow generator, to provide power to the humidifier heater from the power supply in the power supply cavity. Although not shown in the illustrated embodiment, the respective faces may also carry further interconnecting devices, where other electrical or data connections are required to be established between the flow generator and the humidifier or downstream devices including the air conduit or the mask. Such devices may take the form of optically coupled devices, or connectors of other suitable kinds.

The use of such an opto-coupling connector enables the implementation of a simple protocol for communications between the flow generator and the humidifier. For example, the current flow levels of the flow generator can be sent to the humidifier controller which then adjusts the operation of the humidifier according to a predetermined algorithm.

Within the humidifier base unit 151 but not shown here is provided a variable power supply for a heating element which heats a circular metal pad 163. A control knob 164 is provided on the upper surface of the unit for adjustment of the heat supplied to the pad 163. A semicircular wall 165 surrounds the rear part of the pad 163, and carries at its upper edge an inwardly directed flange 166. The pad 163 stands proud of the surrounding base surface 168.

It will be observed that the air flow passage 160 opens to the front face of the base unit at the foot of a circular recess 167 of larger diameter, corresponding to the diameter of the tank air inlet 175 described below. The effect of this is to provide a vertical offset between the air flow passage 160 and the inlet 175, with the former lower than the latter in the normal orientation of the unit. This configuration assists in the prevention of backflow as will be described below. It is to be observed that the axial offset in question could be achieved in other ways.

The recess 167 is provided with a sealing layer of elastomer or other sealing material.

The tank 152 comprises a cover 170 which is preferably of a transparent plastics material, a metal tank base 171 preferably of stainless steel, a base flange 172 which functions to couple the cover and the base, and a sealing gasket 173 which locates between the base of the cover and the metal tank base 171.

Figure 3:
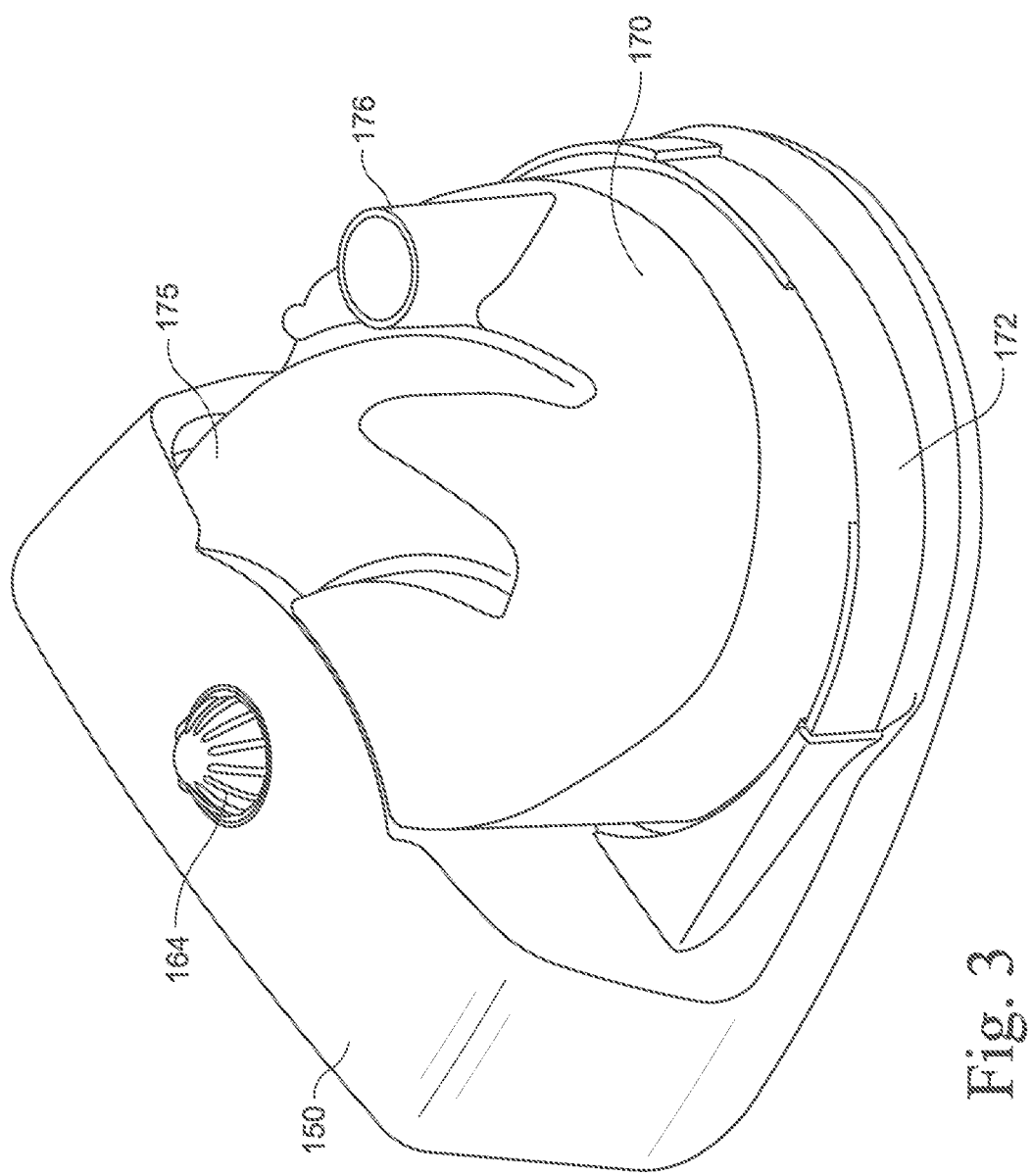
FIG. 3 shows the humidifier unit.
Figure 4:
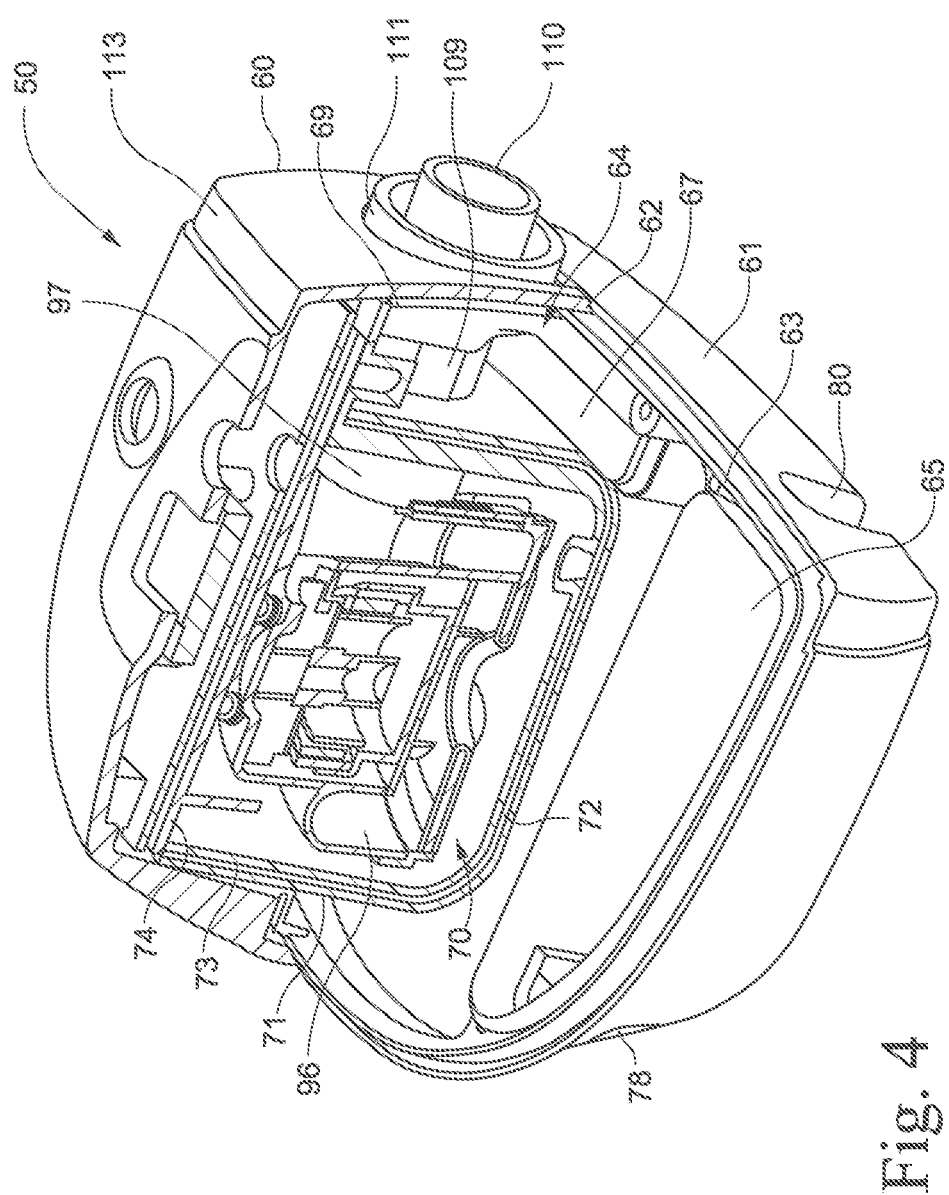
FIG. 4 is a cutaway view of the flow generator.

The periphery of the base flange 172 is dimensioned to slide into engagement with the wall 165 of the base unit and beneath the flange 166 to engage the tank with the base unit, and the tank cover 170 is provided with a cylindrical air inlet 175 extending from its side wall. The inlet 175 is dimensioned to fit sealingly within the recess 167 when the tank is engaged with the base unit as described above and as shown in FIG. 3. An air outlet 176 extends upwardly from the roof of the cover 170 for connection with an air hose for the delivery of humidified air to the patient.

The metal tank base 171 seats within the base flange 172 which is provided with a central aperture, so that the bottom of the metal tank base 171 is exposed to contact the pad 163 when the tank is engaged with the base unit. The metal tank base 171 is thus heated by the heating element of the base unit. To assist in achieving good heat transfer between the pad 163 and the metal tank base 171, the former is resiliently biased upwardly, for example by means of a spring or springs (not shown). This has the further advantage of providing for positive retention of the tank in the base unit, by providing around the central aperture in the base flange, a downwardly directed rim (not shown) which will initially depress the heating plate as the tank is moved into position on the base unit, and which forms a central space into which the heating plate moves under its spring pressure, upon full engagement of the tank with the base unit.

In alternative embodiments not illustrated here, the tank may be provided with locking detents for retention on the base unit.

The lower edge of the cover 170 and the inner edge of the base flange 172 are provided with bayonet type engagement formations 177 and 178 respectively, so the tank components can be assembled and disassembled simply by relative rotation of the cover and the base flange. To assist in this operation, a peripheral groove 179 is provided in the base of the base flange 172, and this groove is interrupted at intervals by finger-engaging bridges 180. The inner wall of the groove 179 protects the user's fingers against accidental contact with the metal tank base 171, in case removal of the cover is carried out while the base is still hot.

The tank is intended to be filled via the air outlet 176, and the apparatus may be provided with a filling bottle with a spout dimensioned for a convenient fit with that outlet. Such a bottle may be provided with a spout of the kind incorporating an air bleed passage which will allow the tank to fill to the correct predetermined height.

In alternative embodiments, other filling arrangements may be employed. The correct filling height is also indicated by filling level graduations 184 scribed or otherwise marked on the wall of the cover 170.

Figure 16:
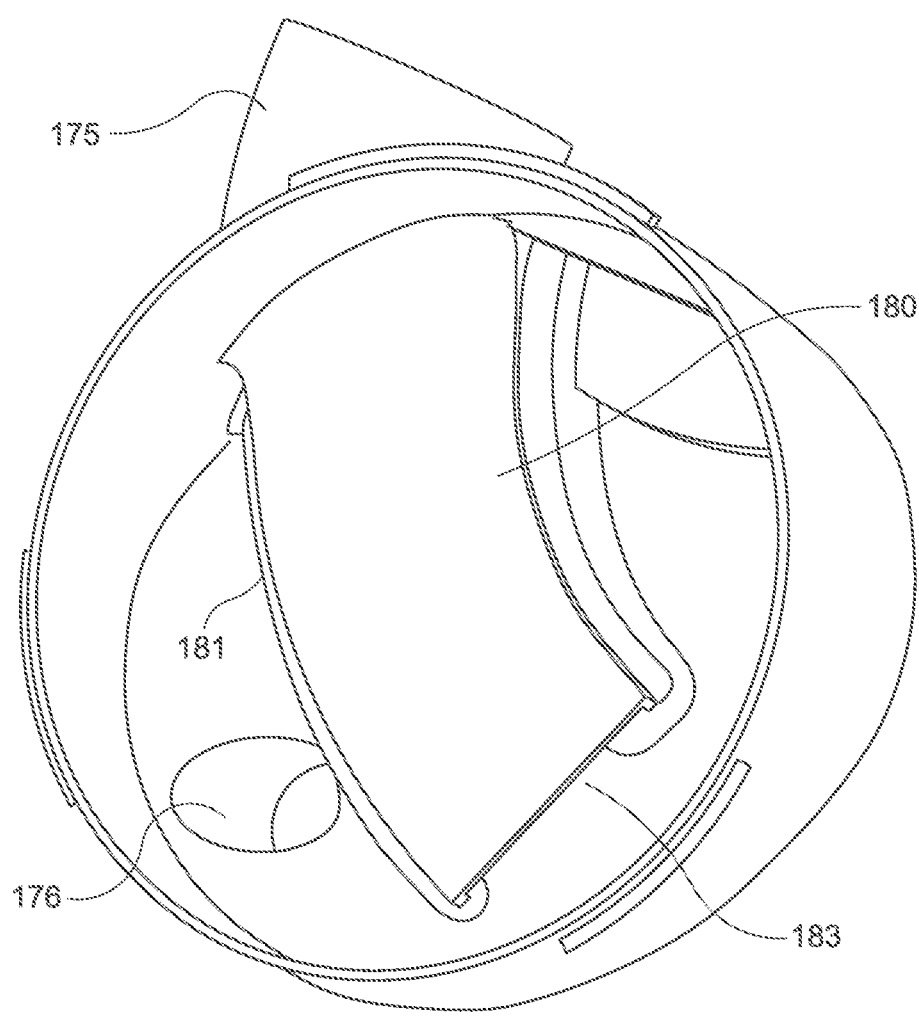
FIG. 16 is an underneath view of the tank cover.

As will be seen in FIG. 16, the air inlet 175 of the cover 170 extends within the cover in the form of an arcuate passage 181, to open to the interior of the cover at a point beyond, in the direction of air flow, the outlet 176. The outlet 183 of the passage 181 is directed obliquely towards the inner wall of the cover. The outlet 176 is, furthermore, between the convexly curved side of the passage 181. This configuration has several important consequences.

Firstly the curvature of the passage 181 and the oblique orientation of its outlet 183 will induce a swirling action on the air mass within the tank, as the air moves around the tank to escape from the outlet 176. This swirling action will enhance the uptake of water vapour from the water contained in the tank.

Secondly the configuration minimises the risk of water from the tank flowing back into the air inlet passage should the tank be tilted while containing water. Whenever the orientation of the tank is such that the air outlet 176 is below the outlet 183, water will flow into the air outlet 176 before it will flow into the inlet passage, and whenever the air outlet is above the outlet 183, then except in the case of inversion of the tank, water will not escape via the arcuate passage 181 unless the tank has been filled with a volume of water which is greater than that which is contained within the sector of the tank below a tangent to the convex surface of the passage 181. This can be avoided by appropriate setting of the heights of the filling level graduations 184.

Should water escape into the passage 181 due to inversion of the humidifier while it is engaged with the flow generator, its path to the air flow passage 160 will be blocked by the dam formed by the face of the recess 167, which will then be below the passage 160.

Figure 17:
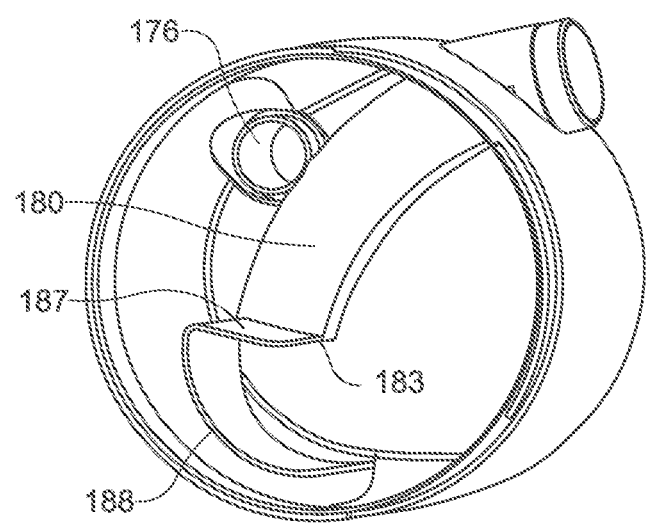
FIG. 17 is an underneath view of a modified tank cover.
Figure 18:
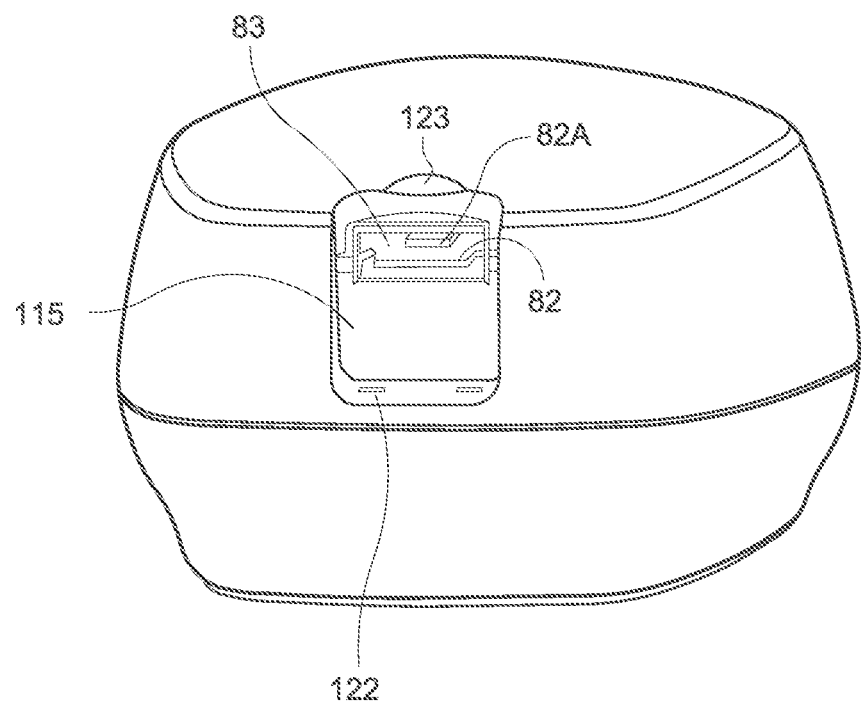
FIG. 18 shows an exemplary modular connector arrangement.
Figure 19A:
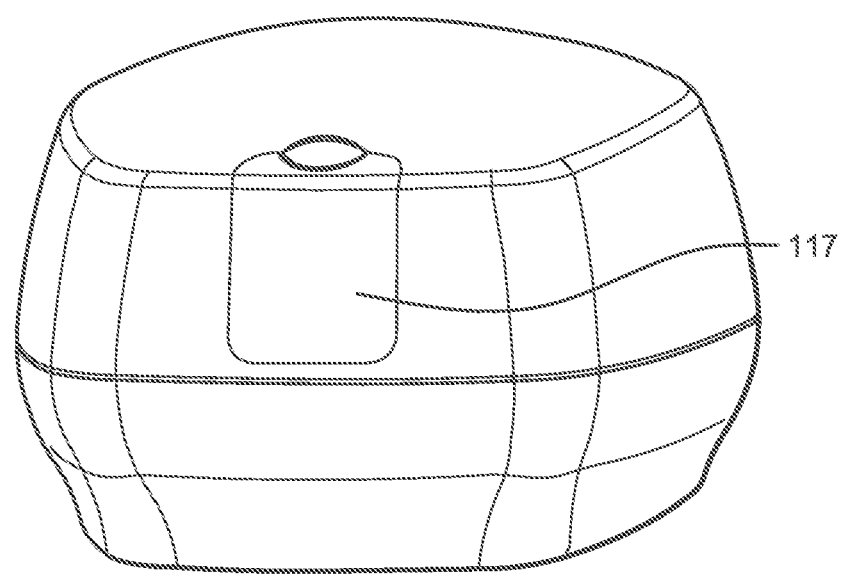
FIG. 19A shows an exemplary modular connector arrangement with the exemplary cover of FIG. 19.
Figure 19:
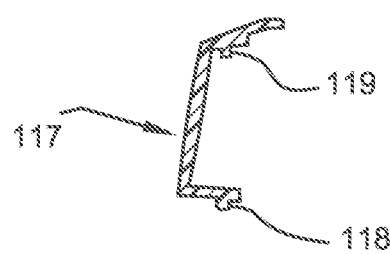
FIG. 19 shows an exemplary cover for an exemplary modular connector arrangement.

FIG. 17 shows a modified form of tank cover in which a downwardly extending wall 187 is provided across the end of the arcuate passage 181, this wall extending in a curved wall 188 beyond the outlet 183. The curved wall 188 assists in the formation of a swirling air flow within the tank, while both walls 187 and 188 tend to protect the outlet 183 against wave action within the tank during transport.

Figure 14:
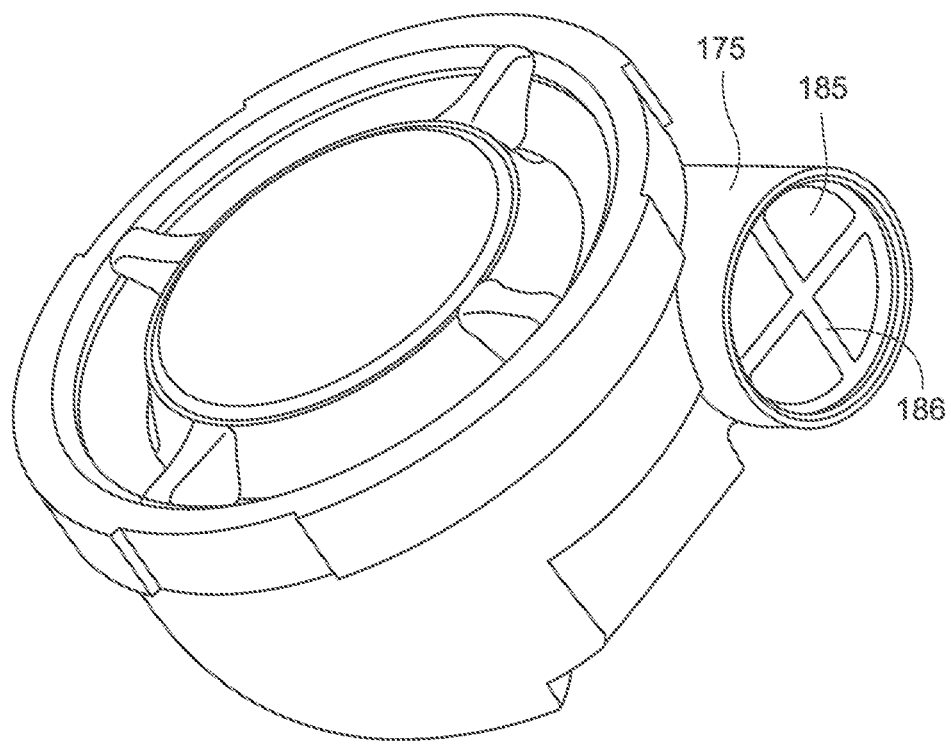
FIG. 14 is an underneath view of the tank showing an alternative valve.
Figure 15:
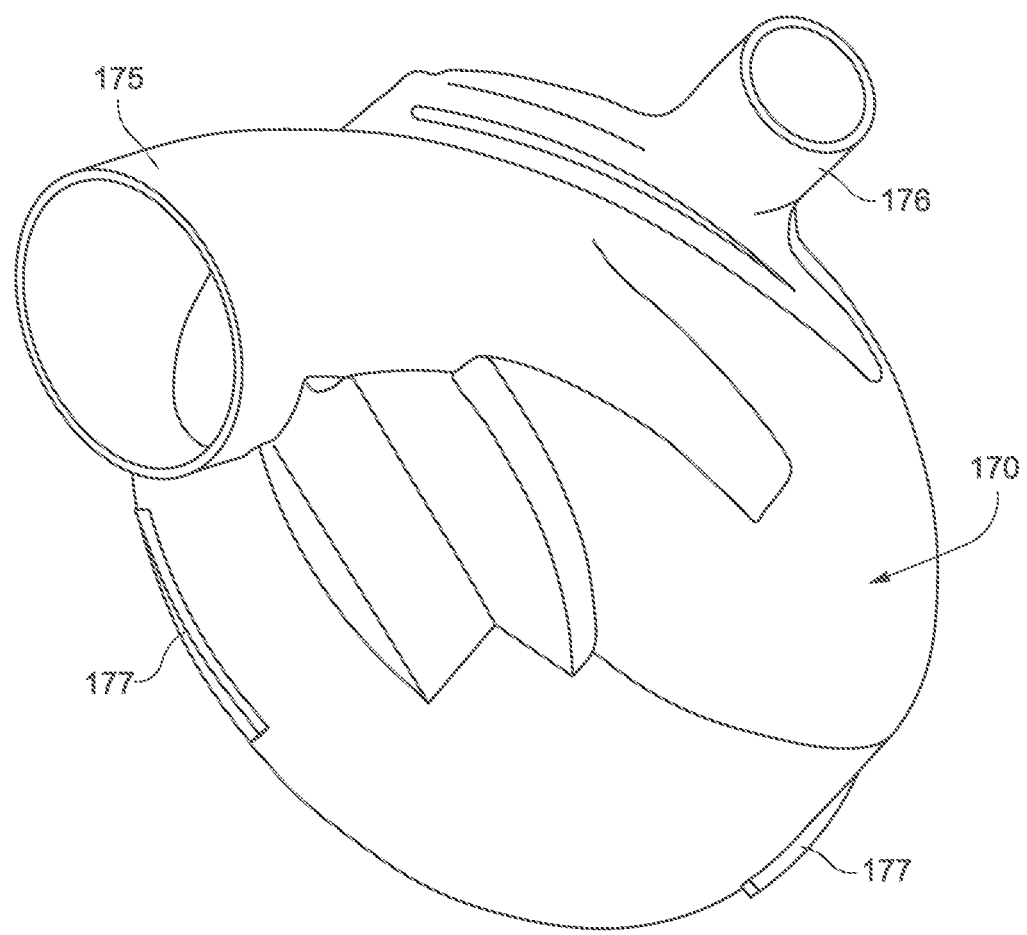
FIG. 15 is a view of the tank cover.

If desired, further security against backflow can be provided by locating a non-return valve at an appropriate point. An example of this is shown in FIG. 14, where a valve comprising a flexible membrane 185 supported on a spider 186 is placed in the mouth of the tank air inlet 175.

In the illustrated embodiment the arcuate passage 181 is shown as a low profile passage of substantially rectangular cross-section. An alternative approach is to continue this passage as a cylindrical passage having a diameter similar to that of the air passage leading from the flow generator to the humidifier. The advantage of this will be to avoid the introduction of impedance to the flow of air through the humidifier. Generally speaking it is desirable to minimise pressure drop through the humidifier, to avoid interfering with diagnostic or monitoring functions in the flow generator, for example the detection of snoring, which require the detection of sound transmitted back through the system from the patient.

The enhanced uptake of water vapour achieved by inducing the swirling of air as it passes through the tank enables, in an alternative embodiment of the invention, the elimination of the heating of the water in the tank 152. In such an embodiment the heating element and its controls, and the heat transfer components including the pad 163 and the metal tank base 171 are eliminated, and the humidifier becomes a simpler, passive, device.

FIGS. 18 to 21 show various forms of modular data connections foreshadowed earlier, utilizing the connector aperture 83 in the rear of the flow generator housing.

The connector aperture 83 is provided in the wall of a rectangular recess 115. An arcuate depression 123 is provided in the upper surface of the unit above the recess 115 to facilitate removal of closure elements from the depression, as described below.

Where the flow generator in question is not intended to be employed with any data connection, the connector aperture 83 is closed off by a blank closure element 117, shaped to fit into the recess 115. This element snaps into the recess by means of lower tabs 118 and an upper tab 119 which fit corresponding depressions such as 122 in the walls of the recess 115, to close the connector aperture 83 and conform to the contours of the surrounding surface of the unit.

Figure 20:
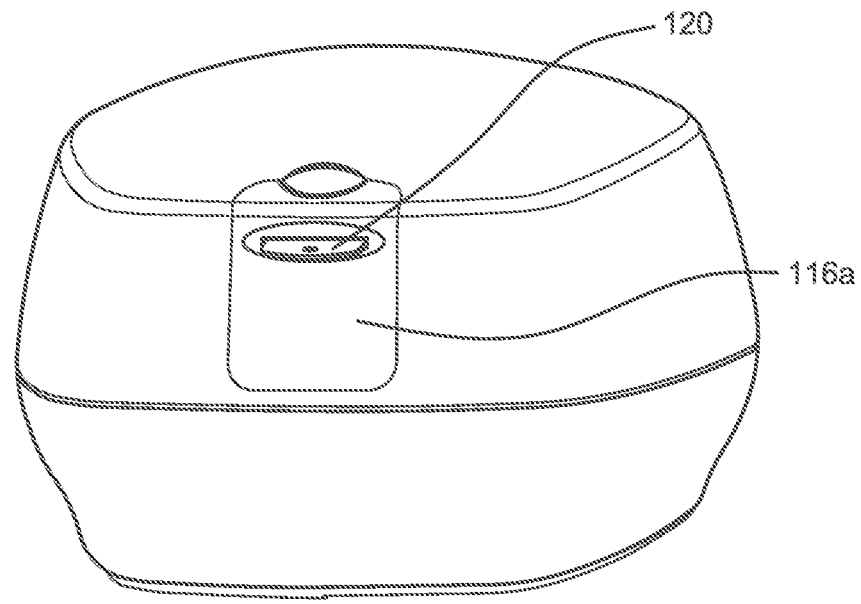
FIG. 20 shows an exemplary modular connector arrangement.
Figure 21:
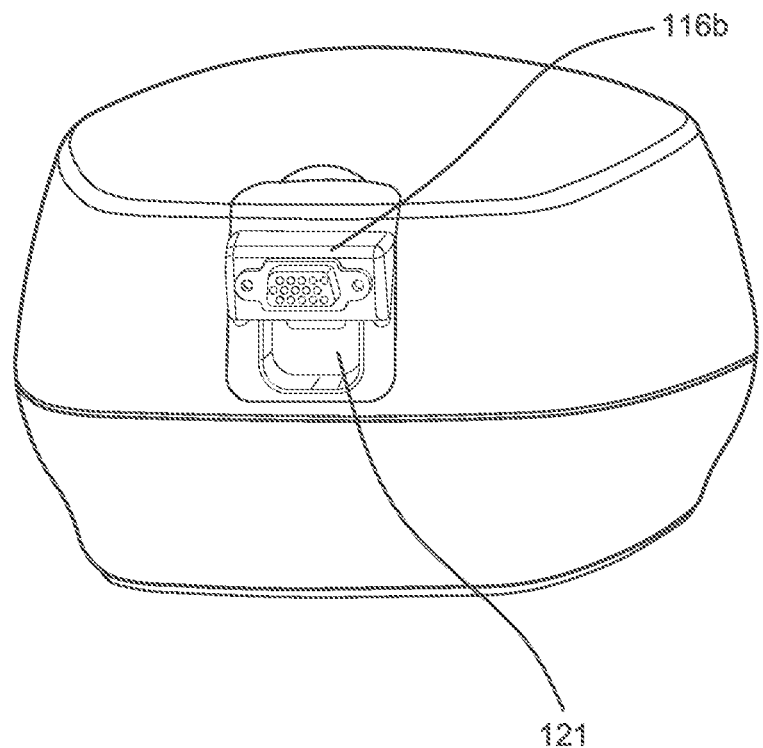
FIG. 21 shows an exemplary modular connector arrangement.

Complementarily shaped closure elements can be provided for the reception of different kinds of data devices. Shown in FIG. 20 is an element 116a provided with a slot for the reception of a smart card 120. The element 116a or the printed circuit board itself may carry the necessary smart card socket. Shown in FIG. 21 is an element 116b provided with a DB type data socket. In this case the element 116b is contoured to provide a lower front recess 121 to facilitate gripping of the associated plug.

Other forms of element 116 can be provided to enable the connection of devices such as memory cards and pre-programmed devices as required. This facility furthermore enables a wide range of devices to be integrated with the apparatus in modular fashion, for example a clock display which may utilise the system clock contained in the flow generator controller, a voice activation unit, oximetry, ECG and other diagnostic aids, a sound recorder, a light.

First Further Embodiment of the Humidifier

With references to FIGS. 22 to 38, a humidifier according to another embodiment of the invention, is described. The humidifier is adapted for attachment to the flow generator in generally similar fashion to the humidifier described above with reference to FIGS. 12 to 17.

The humidifier according to the present embodiment includes a first cradle component 202 (see FIGS. 22 and 23) and a second cradle component 204 (see FIGS. 24 and 25), each being generally L-shaped in side view.

The first cradle component 202 includes a horizontally extending portion 206 and a vertically extending portion 208. The horizontally extending portion 206 has an outer wall 210 and a floor 212, the outer wall and floor defining a recess 214. An aperture 216 is provided in the front extremity of the outer wall 210.

The outer sides 218 of the vertically extending portion 208 are slightly recessed relative to the outer surface of the outer wall 210, so as to define side recesses 220 with forward projecting walls 222.

The vertically extending portion 208 extends upwardly from the upper surface of the outer wall 210, and, about midway up, at 224, is angled rearwardly. A rectangular aperture 226 opens through the vertically extending portion 208, the front of the aperture being defined by a rim 228 which forms a continuation of the rearwardly angled portion at 224.

At the upper end of the vertically extending portion 208 there is provided a rearwardly projecting flange 230, which has a step 232 at its forward extremity.

Defined between the flange 230 and the outer sides 218, at each side of the vertically extending portion 208, is a recess 234.

Figure 22:
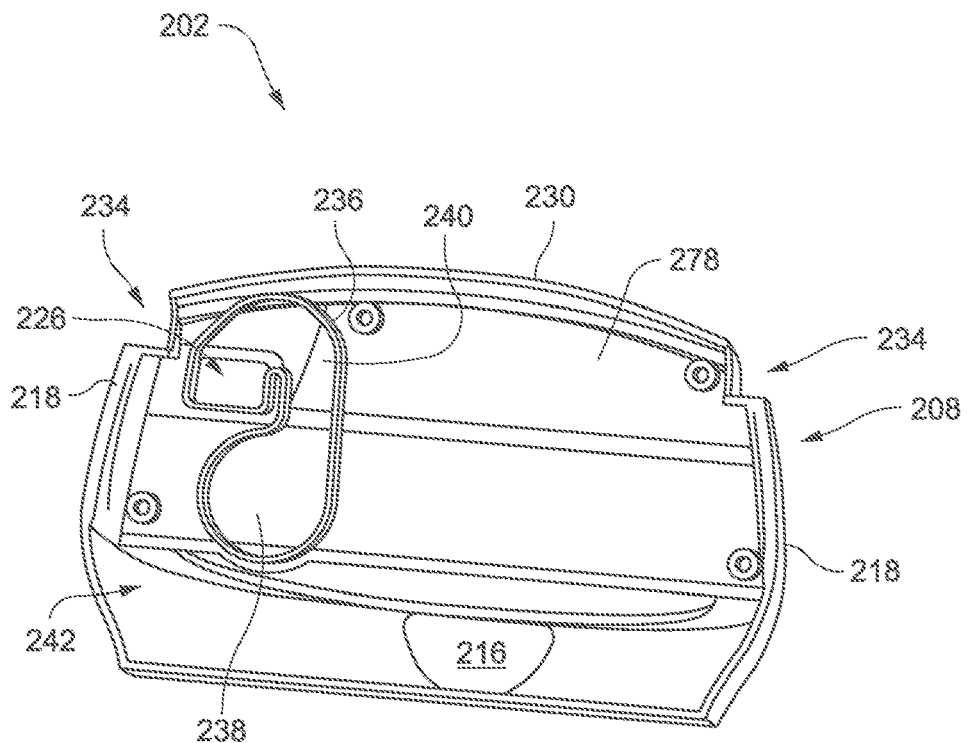
FIG. 22 is a rear view of a first cradle component of a humidifier according to another embodiment.
Figure 23:
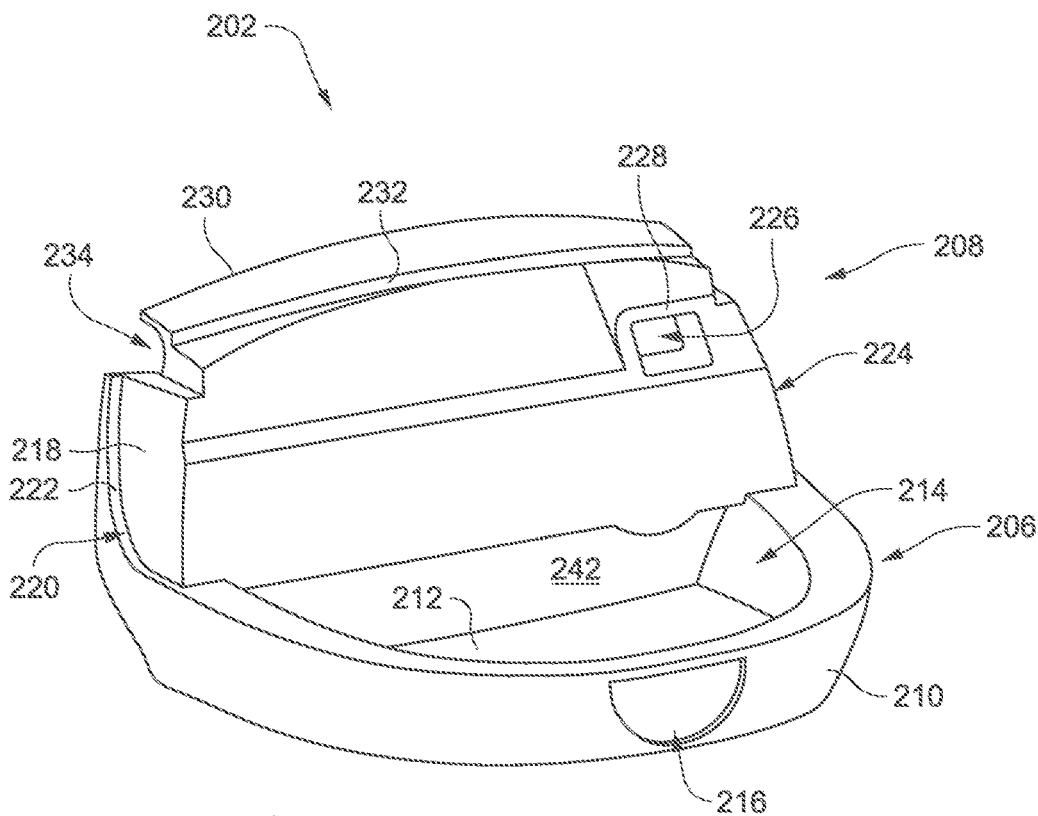
FIG. 23 is a perspective view from the front and above, of the cradle component of FIG. 22.

Referring to FIG. 22, at the rear of the first cradle component 202, there is provided a rearwardly projecting wall 236 which is curved so as to define a closed path, and which extends around the rear of the aperture 226, where the aperture opens through the rear of the vertically extending portion 208. The wall 236 is adapted for fitting of a seal 280 (see FIGS. 34 and 35), and defines a lower, substantially circular region 238 and a narrowed pathway 240 extending from the circular region to the aperture 226.

Between the lowermost edge of the vertically extending portion 208 and the floor 212, there is defined an opening 242.

Figure 24:
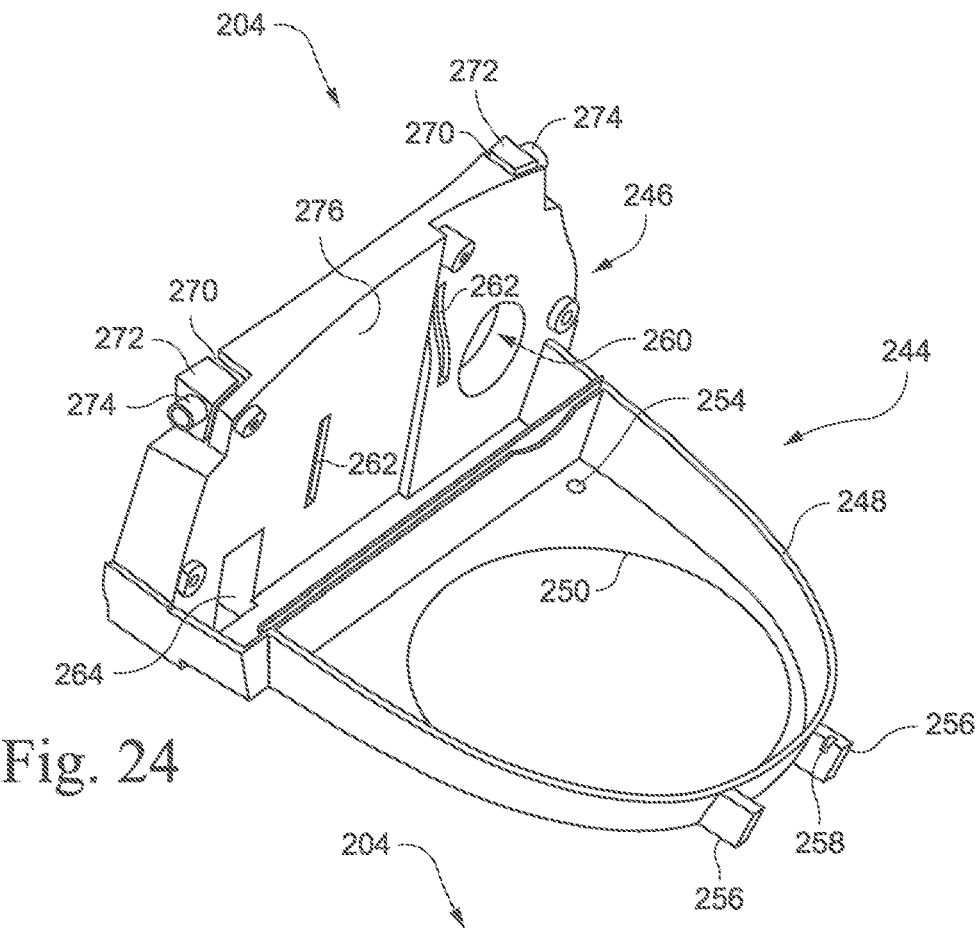
FIG. 24. is a perspective view from the front and above of a second cradle component of the humidifier of FIG. 22.
Figure 25:
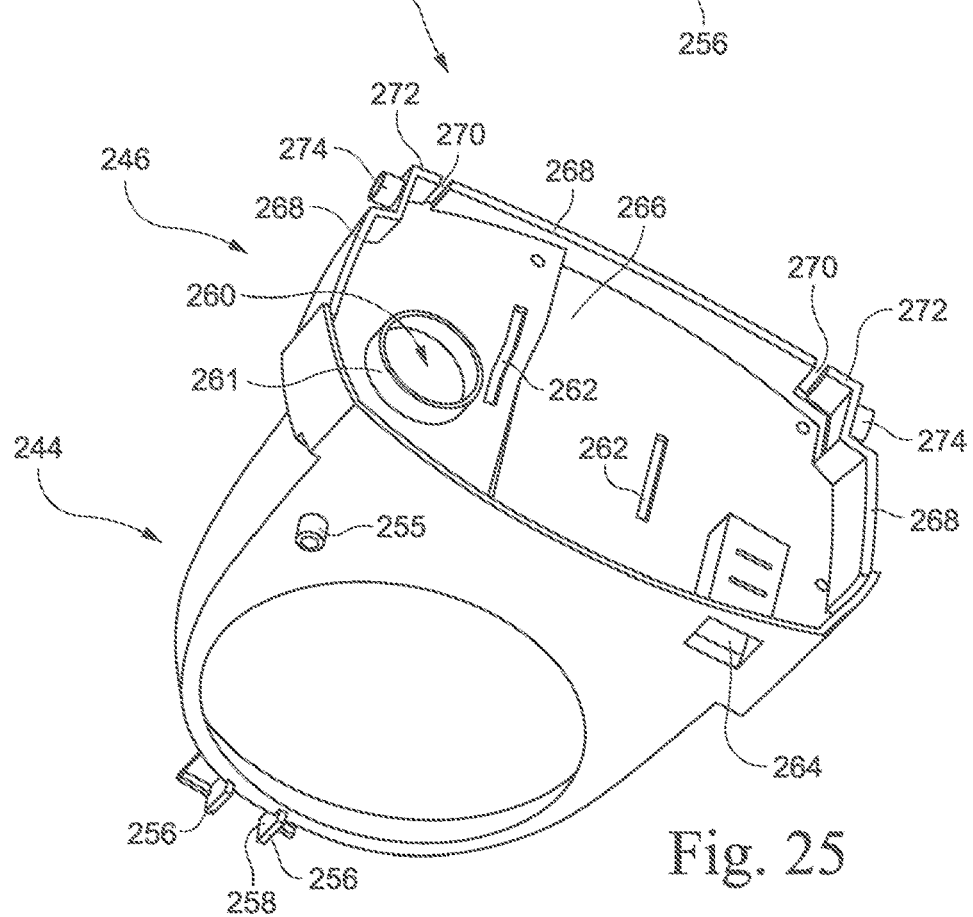
FIG. 25 is a perspective view from the rear and below of the cradle component of FIG. 24.

Reference is now made to the second cradle component 204 in FIGS. 24 and 25. The second cradle component 204 also includes a horizontally extending portion 244 and a vertically extending portion 246.

The horizontally extending portion 244 includes an outer wall 248 and a floor 250. The floor 250 defines a circular opening for retaining a circular heater pad (not shown), generally similar to the circular metal pad 163 shown in FIG. 12. At the rear of the floor 250 is a hole 254 passing through the floor. Beneath the floor 250, there is provided an extension tube 255, the passage of which forms a continuation of the hole 254.

At the front extremity of the outer wall 248 are a pair of brackets 256 which are spaced apart from each other, each bracket having an upwardly extending slot 258 which is opened at its upper end, and closed at its lower end.

The vertically extending portion 246 of the second cradle component 204 has a circular aperture 260 with a rearwardly extending spigot 261, as well as a pair of narrow vertical slots 262, opening through it.

There is also provided a rectangular shaped aperture 264, for electrical connections between the humidifier and the flow generator, or for electrical and signal connections to the humidifier.

The upper and side extremities of the vertically extending portion 246 project rearwardly, beyond a rear face 266 of the vertically extending portion, to form a flange 268. At each of the outer two upper corners of the vertically extending portion, there is provided a dog-legged gap 270, each gap separating, from a remainder of the flange 268, a support formation 272. Each support formation 272 has a cylindrically shaped hub 274 extending sideways from it. It will be appreciated that each support formation 272, as a result of the respective gap 270, is only joined to the remainder of the flange 268 at a lower end of the support formation. Accordingly, the gaps 270 allow for a degree of movement of each support formation 272, and hence its respective hub 274, relative to the remainder of the vertically extending portion 246, for a reason that will be described below.

After attachment of the seal 280 to the wall 236 at the back of the first cradle component, as described below, the first cradle component 202 and second cradle component 204 are assembled together by inserting the horizontally extending portion 244 of the second cradle component through the opening 242 in the first cradle component, so that the horizontally extending portion 244 is disposed above the floor 212 of the first cradle component, within the recess 214. In this configuration, a front face 276 of the vertically extending portion 246 of the second cradle component 204 abuts a rear face 278 of the vertically extending portion 208 of the first cradle component 202.

In this configuration, the vertically extending portion 246 of the second cradle component 204 is accommodated below the flange 230, and between the outer sides 218 of the vertically extending portion 208 of the first cradle component 202, with the hubs 274 being accommodated in the recesses 234.

Figure 33:
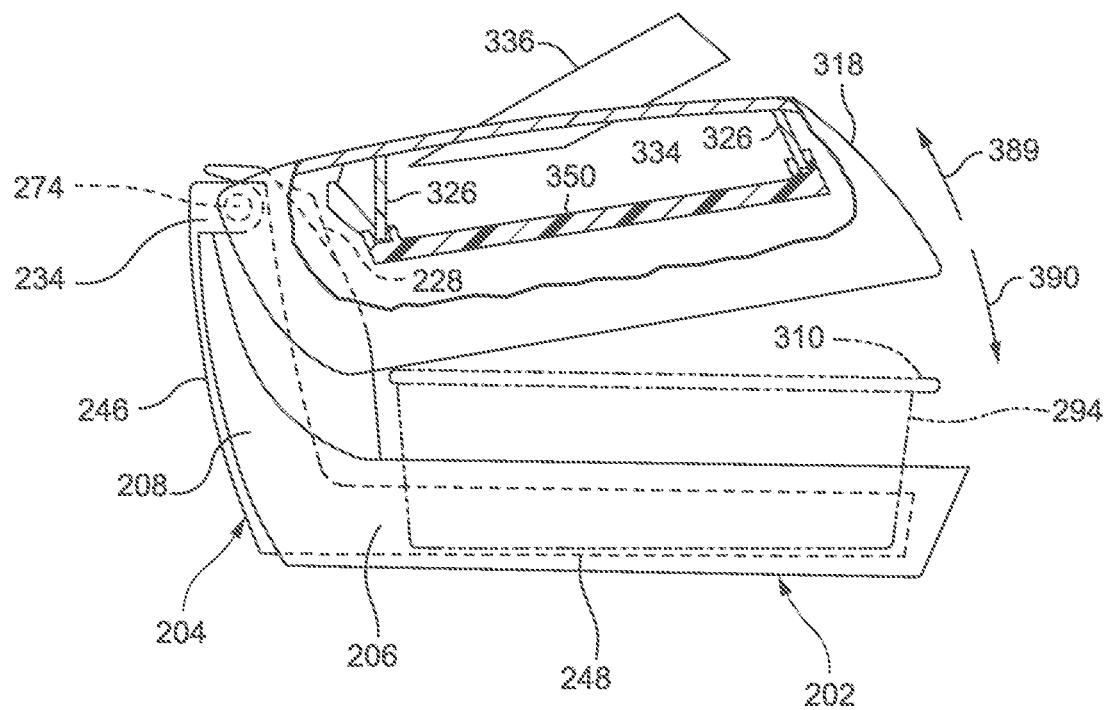
FIG. 33 is a schematic side elevation, shown partly cut away, and partly in hidden detail, of the humidifier of FIG. 22.
Figure 34:
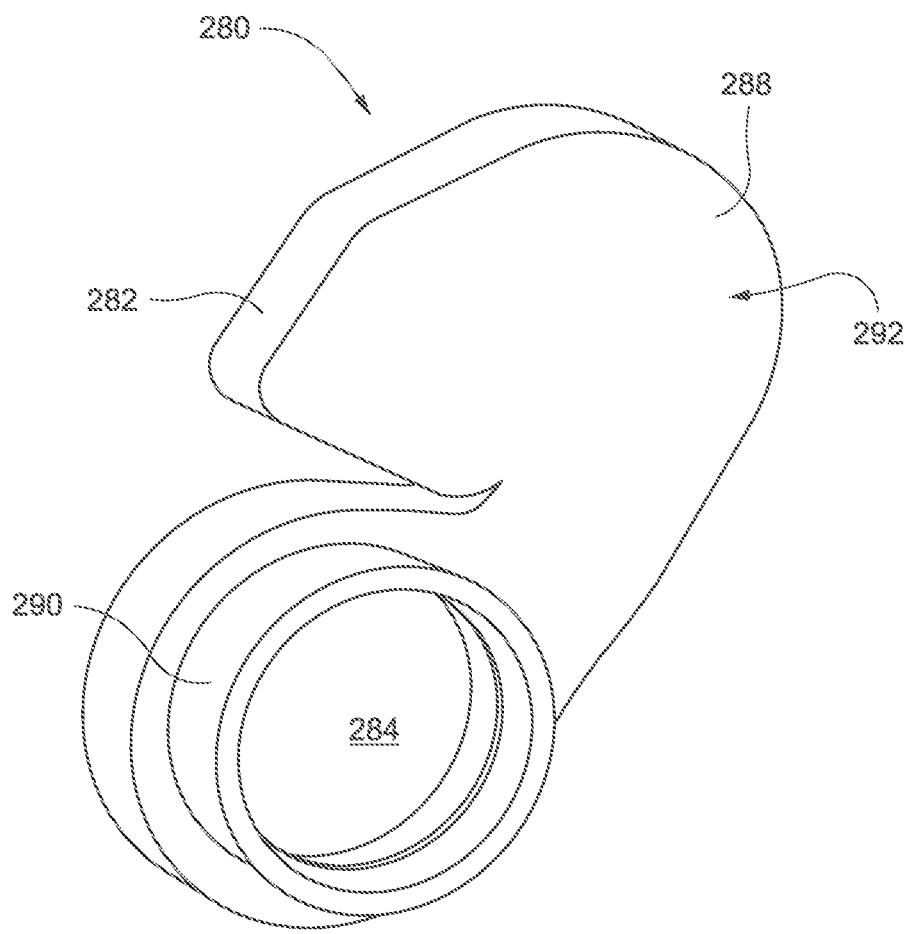
FIG. 34 is a perspective view from the rear, of an airway seal of the humidifier of FIG. 22.
Figure 35:
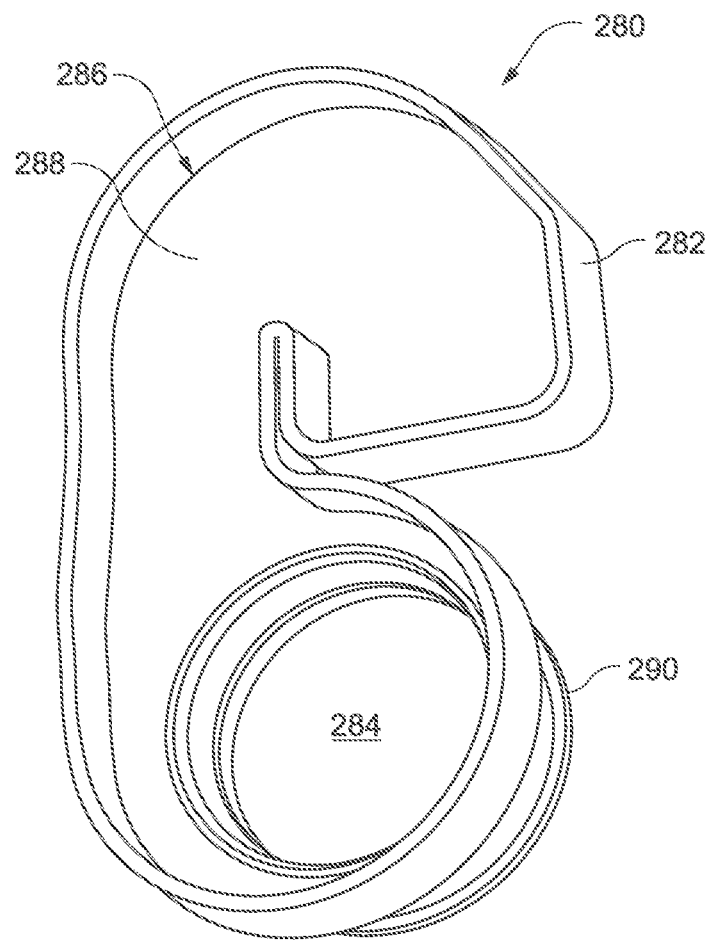
FIG. 35 is a perspective view from the front and below of the airway seal of FIG. 34.

The configuration of the assembled first and second cradle components 202 and 204, respectively, may be better understood with reference to FIG. 33.

Prior to assembly of the first and second cradle components 202 and 204, respectively, as described above, an airway seal 280 (see FIGS. 34 and 35) is engaged with the rearwardly projecting wall 236. The airway seal 280 has a side wall 282 defining a perimeter of the airway seal, the side wall having a shape which is complimentary to that of the rearwardly projecting wall 236. This permits the rearwardly projecting wall 236 to be attached to the side wall 282 as a press-fit.

The airway seal 280 defines a circular aperture 284 which opens through the front face 286 of a rear wall 288 of the airway seal 280, and through a tubular portion 290, which projects rearwardly from a rear face 292 of the rear wall 288. It will be appreciated that the circular aperture 284 is aligned with the circular region 238 defined by the rearwardly projecting wall 236. Accordingly, with the airway seal 280 engaged with the rearwardly projecting wall 236, when the second cradle component 204 is engaged with the first cradle component 202 as described above, the tubular portion 290 of the airway seal 280 is received as a close fit in the circular aperture 260 of the vertically extending portion 246 of the second cradle component. As a result, the airway seal 280 defines a closed passage from the circular aperture 260 to the rectangular aperture 226 in the vertically extending portion 208 of the first cradle component 202.

Figure 26:
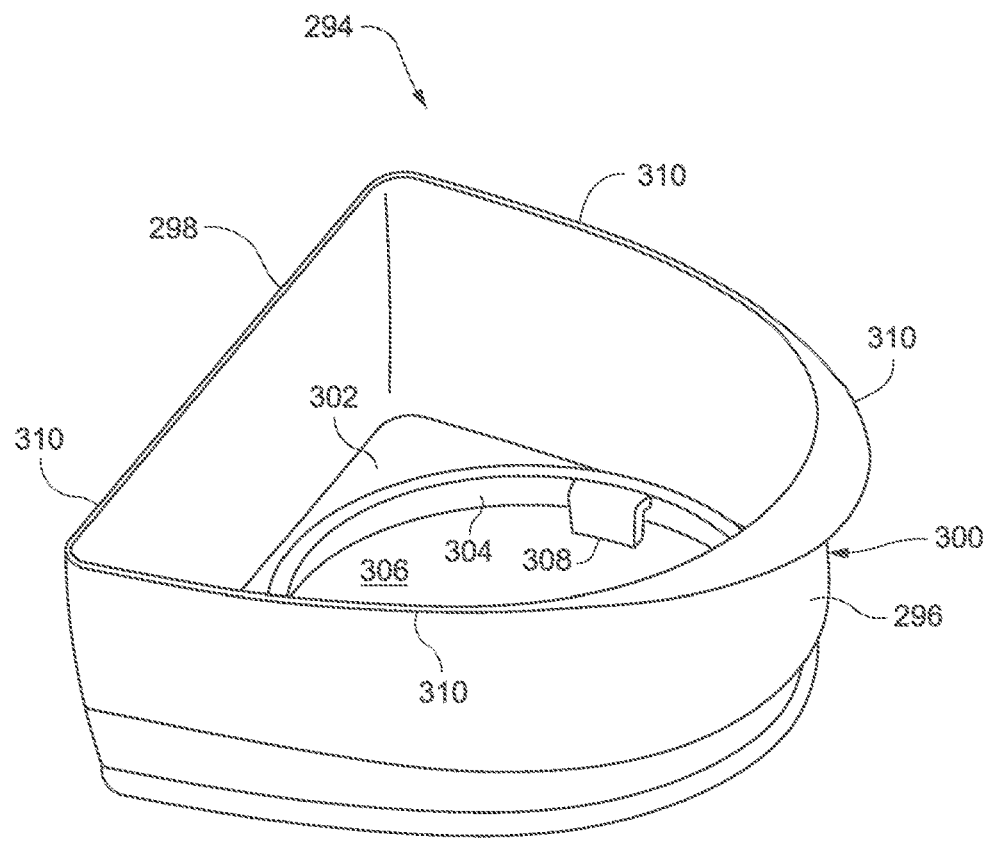
FIG. 26 is a perspective view from the front and above, of a water receptacle of the humidifier of FIG. 22.
Figure 27:
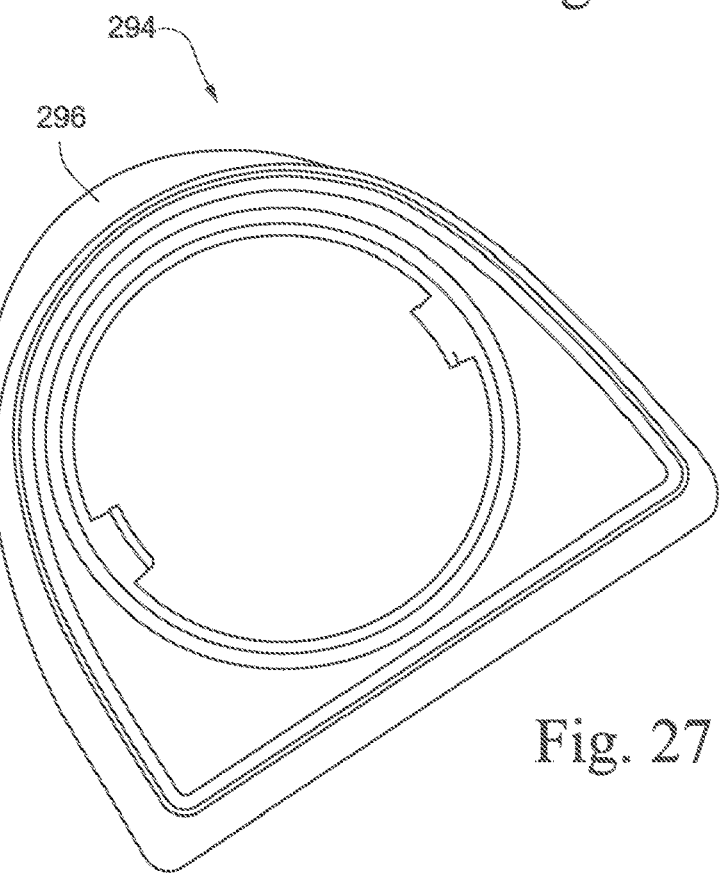
FIG. 27 is an underneath view of the receptacle of FIG. 26.

Referring to FIGS. 26 and 27, there is shown a water receptacle 294. The water receptacle 294 has a front wall 296 and a rear wall 298. The front wall 296 extends forwards from the rear wall 298 to a curved front at 300. The water receptacle 294 has a floor 302, the floor having a rim 304 defining a circular opening 306.

At the top of the front and rear walls 296 and 298, respectively, there is provided an outwardly extending flange 310. Although the flange is present along the full extent of the upper edges of the front wall 296 and rear wall 298, it is of a greater dimension at the front of the water receptacle 294 (above the position 300) as shown in FIG. 26.

At each side of the circular opening 306, there is a hook-shaped formation 308, which extends from the rim 304, inwards relative to the opening 306, and then downwards. The formation 308 is used to engage with a heat-transferable bottom (not shown) which extends over the opening 306 and which forms a seal with the rim 304 so that the water receptacle 294 is suitable for retaining a supply of water therein.

The water receptacle 294 is shaped complementarily relative to the space defined by the outer wall 248 and floor 250 of the horizontally extending portion 244 of the second cradle component 204. Thus, once the second cradle component 204 has been assembled with the first cradle component 202 as described above, the water receptacle 294 can be placed on the floor 250 of the second cradle component as illustrated in FIG. 33 (in which the water receptacle is shown in phantom lines).

Figure 28:
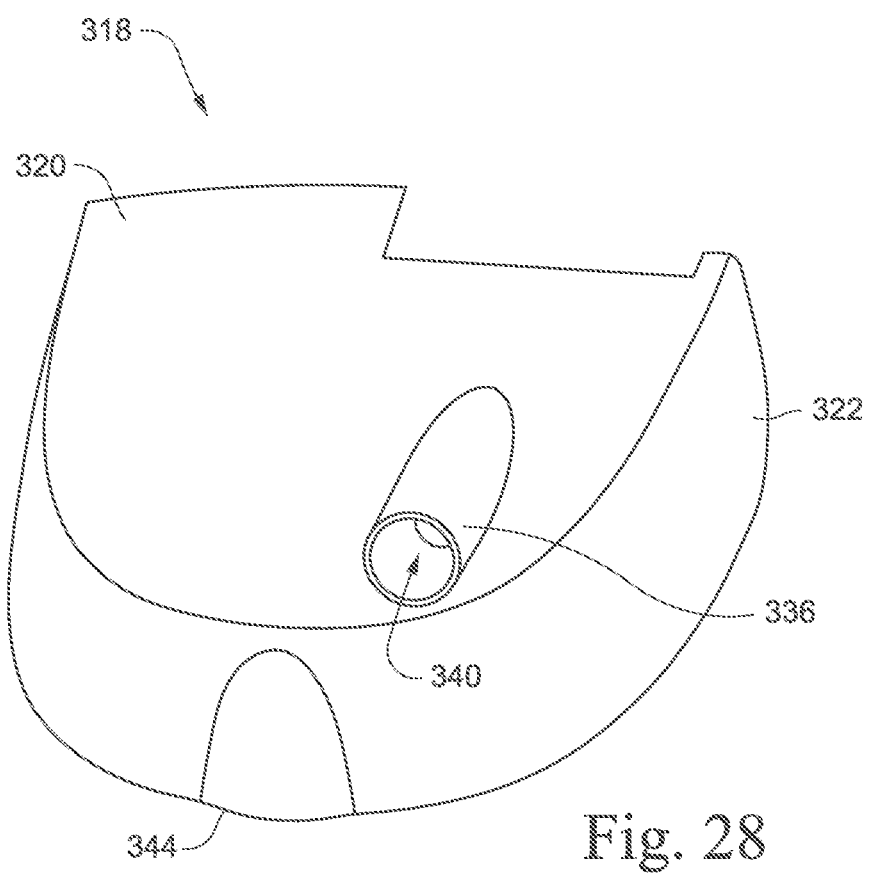
FIG. 28 is a perspective view from the front and above, of a lid of the humidifier of FIG. 22.
Figure 29:
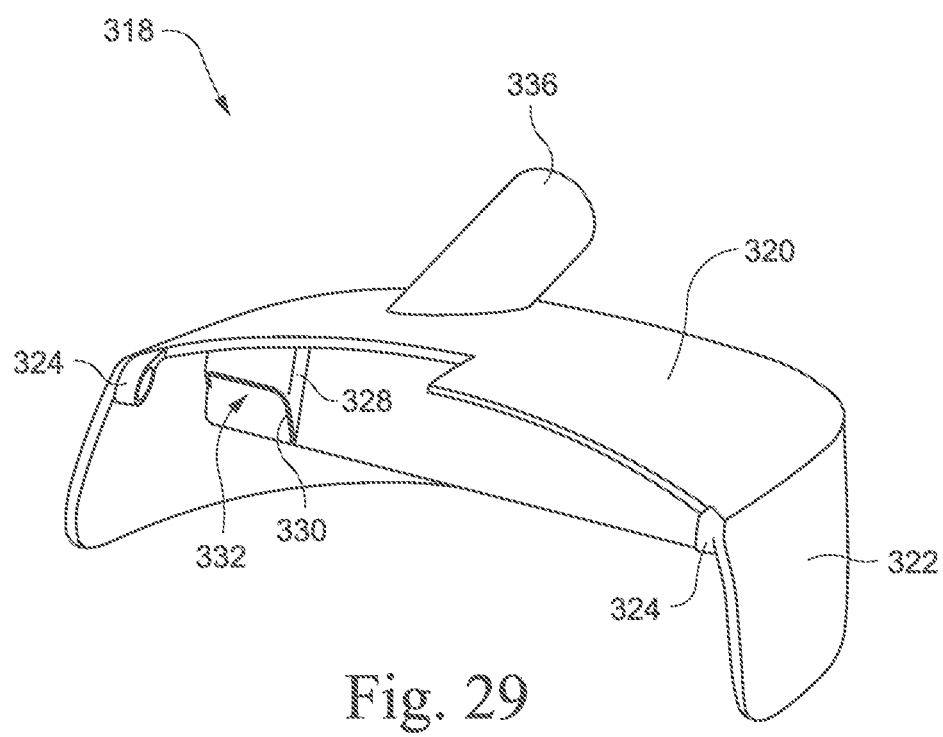
FIG. 29 is a perspective view from the rear, of the lid of FIG. 28.
Figure 30:
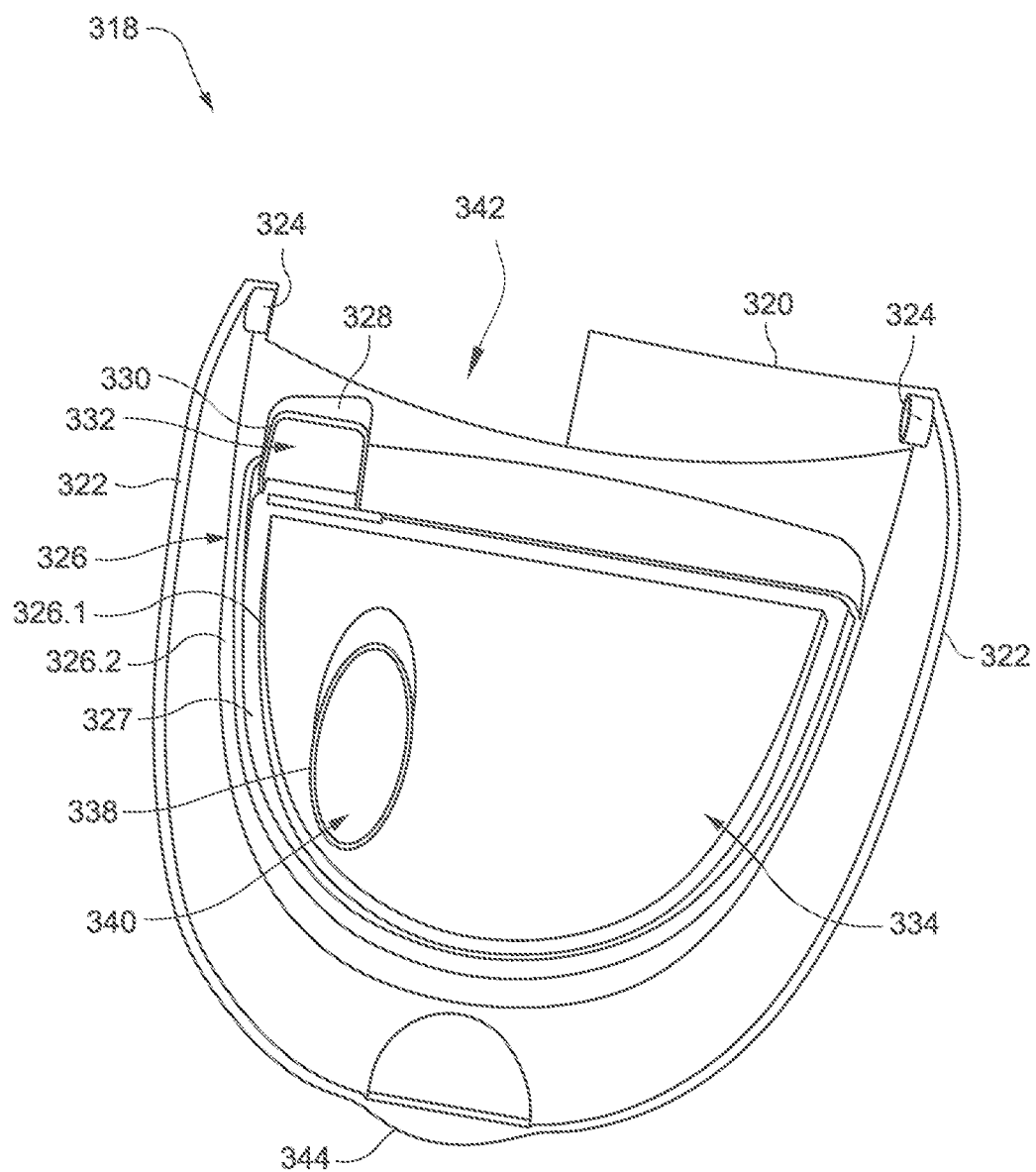
FIG. 30 is an underneath view of the lid of FIG. 28.

Referring now to FIGS. 28 to 30, there is shown a lid 318 of the humidifier according to the present embodiment. The lid 318 has an upper wall 320 and a downwardly extending wall 322, extending from the upper wall.

The lid 318 includes a pair of sockets 324 positioned at the rear extremities of the downwardly extending wall 322, immediately below the upper wall 320, for hinged connection to the hubs 274 of the second cradle.

A double wall 326 depends from the upper wall 320 and includes an inner wall portion 326.1 and an outer wall portion 326.2. The wall portions 326.1 and 326.2 define, between them, a channel 327. At the rear of the double wall 326 is a tubular structure 328 of substantially rectangular cross-section. The lower end of the tubular structure is constituted by a rim 330 which is angled upwardly in a rearward direction. The tubular structure 328 defines an internal passage 332 which passes through the double wall 326, to create an air passage from the aperture 226 in the first cradle to an internal region 334 of the lid defined by the inner portion 326.1 of the double wall.

Extending at an acute angle to the horizontal, from the upper surface of the upper wall 320, is a pipe 336. This is for attachment of a hose to supply humidified air to a patient. The pipe 336 passes through the upper wall 320, with the lower end of the pipe projecting beyond the lower surface of the upper wall, to terminate at a rim 338. The passage 340 of the pipe 336 opens into the internal region 334.

The upper wall 320 defines, at its rear edge, a recess 342. At the front of the downwardly extending wall 322, there is an outwardly-curved finger-grip formation 344.

Figure 31:
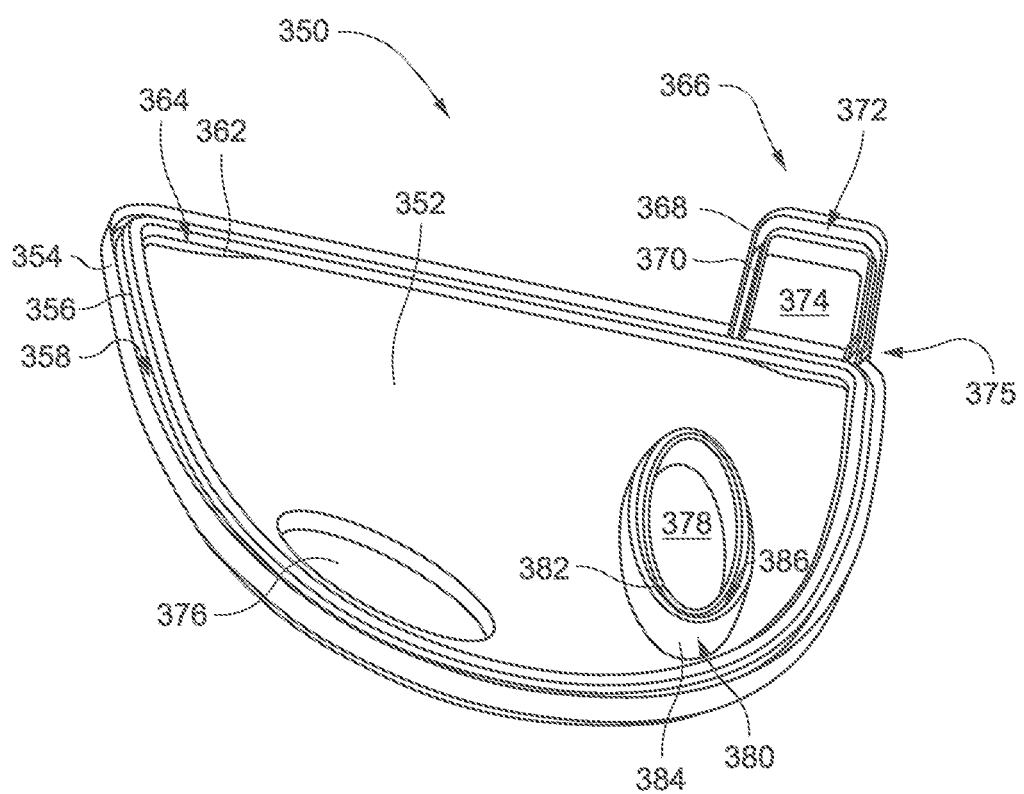
FIG. 31 is a perspective view from the front and above, of a lid seal of the humidifier of FIG. 22.
Figure 32:
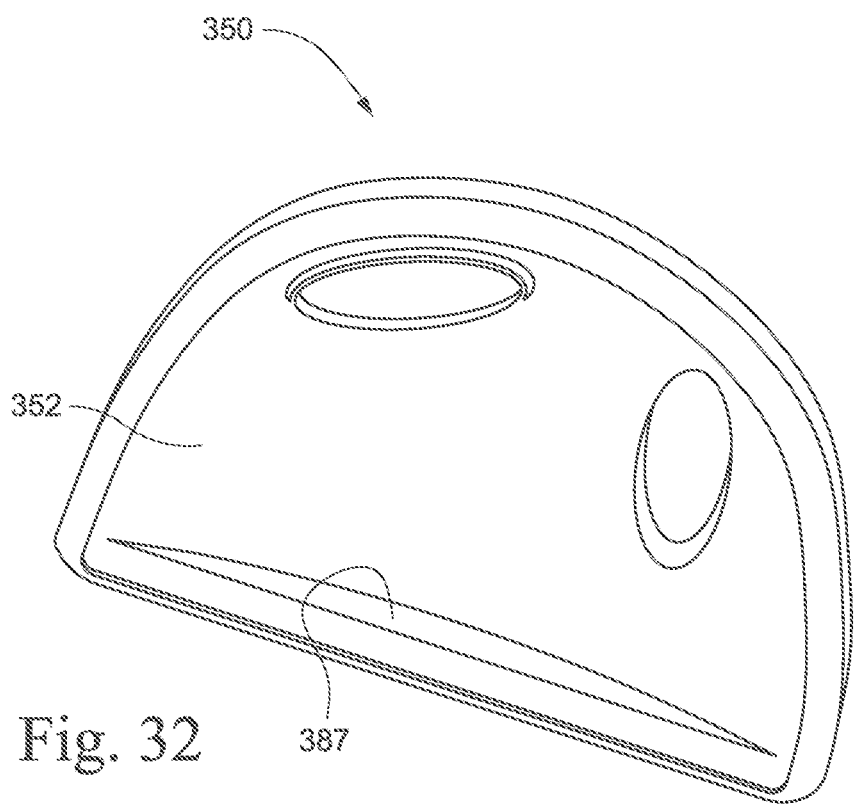
FIG. 32 is an underneath view of the lid seal of FIG. 31.

Attached to the lid 318, as shown in FIG. 33, is a lid seal 350, which is illustrated in FIGS. 31 and 32. The position of the lid seal 350 relative to the lid 318 is illustrated in FIG. 33. The lid seal 350 has a centre wall 352, and, projecting upwards from the centre wall, an outer wall 354 and an inner wall 356. The outer wall 354 and inner wall 356 define, between them, a channel 358. In addition, the upper surface of the centre wall 352 has an upwardly projecting curvature 362 which terminates, at its rear edge, at a position spaced from the inner wall 356, such that a recess 364 is defined immediately adjacent the inner wall, positioned inwards relative to the lid seal 350.

At the rear of the lid seal 350 is a frame formation 366 having an outer wall 368 and an inner wall 370, the outer and inner wall defining, between them, a channel 372. The inner wall 370 defines a substantially rectangular centre aperture 374. The outer and inner walls, 368 and 370, respectively, each terminate, at their forwardmost edges at 375, in line with the inner surface of the outer wall 354, so as not to interrupt the channel 358 defined between the outer wall 354 and inner wall 356.

The lid seal 350 has a roughly elliptical inlet opening 376, and an elliptical outlet opening 378. Extending upwardly from the upper surface of the centre wall 352 is an outlet formation 380 which consists of an inner wall 382 and an outer wall 384, the inner and outer walls defining, between them, a channel 386.

The lower surface of the centre wall 352 of the lid seal 350 is concave as shown in FIG. 32, to define a rear, forwardly projecting face 387.

The lid seal 350 is attached to the lid 318. This is achieved by way of the inner wall 356 of the lid seal being received as a press-fit in the channel 327 defined by the double wall 326 of the lid. The outer portion 326.2 is accommodated in the recess 364 of the lid seal 350. In addition, the rim 338 of the humidified air outlet pipe 336 passing through the lid 318 is received as a press-fit in the channel 386 of the outlet formation 380 of the lid seal 350. Furthermore, the rim 330 of the rectangular tubular structure 328 of the lid 318 is received as a press-fit in the channel 372 of the frame formation 366. Accordingly, the manner of attachment of the lid seal 350 effects proper sealing with the lid 318 to define an internal region 334 of the lid.

The rectangular centre aperture 374 defined by the frame formation 366 of the lid seal 350 is aligned with the passage 332 in the tubular structure 328 of the lid 318, so as to open into the internal region 334. However, as a result of the press-fit between the rim 338 of the pipe 336 and the outlet formation 380 of the lid seal 350, the passage 340 of the pipe does not open into the internal region 334, but effectively extends, from the upper edge of the pipe as shown in FIG. 29, through the lid to a position below the lid seal.

Figure 38:
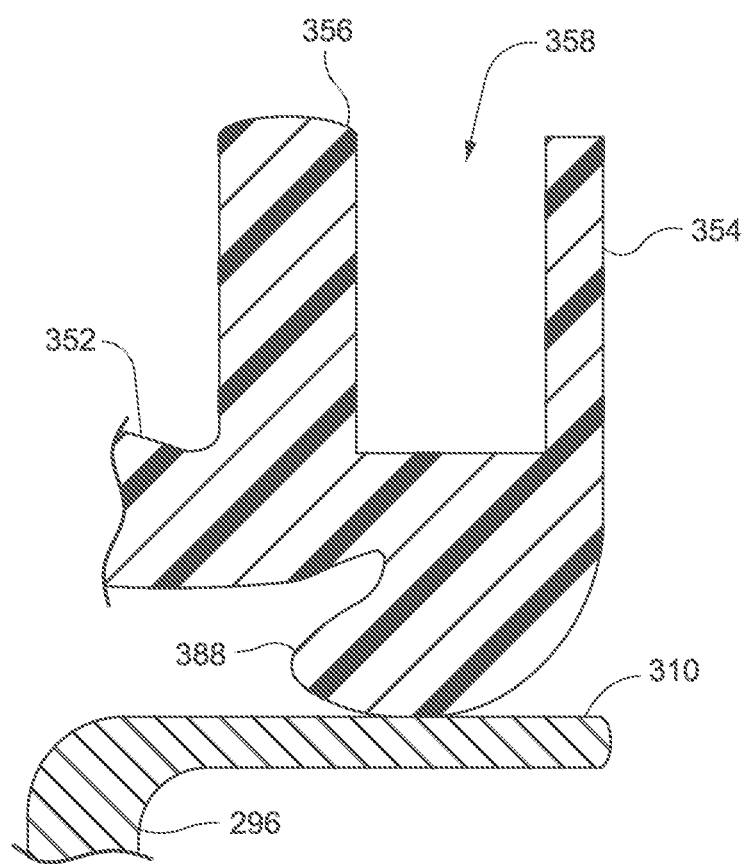
FIG. 38 is a schematic section view through parts of the humidifier of FIG. 22.

The lid seal 350 may be provided with a downwardly extending, and inwardly curved, sealing flange 388 as shown in FIG. 38.

When the lid 318 is in its closed position, the lid seal 350 seals against the flange 310 of the water receptacle 294. FIG. 38 shows the embodiment of the lid seal 350 which includes a sealing flange 388, this sealing flange being the part of the lid seal which engages the flange 310.

The lid 318 is engaged with the second cradle component 204 by way of the hubs 274 of the second cradle component being received in the sockets 324 of the lid, so that the hubs and sockets together constitute hinges. This allows the lid 318 to be opened and closed relative to the first and second cradle components 202 and 204, respectively, as indicated by the arrows 389 and 390 in FIG. 33.

During opening of the lid 318, it may be freely rotated about the hubs 274 through greater than 90° until it reaches a maximum extent of normal travel. The lid 318 and second cradle component 204 are configured such that, if the lid 318 is then rotated further, the hubs 274 pop out of the sockets 324. This may be achieved, as would be understood by a person skilled in the art, by providing suitable chamfers on the hubs 274 and/or sockets 324, or other suitable formations on the lid 318 or second cradle component 204, so that the support formations 272 flex relative to the remainder of the vertically extending portion 246 of the second cradle component, to allow the hubs to be displaced from the sockets.

Figure 36:
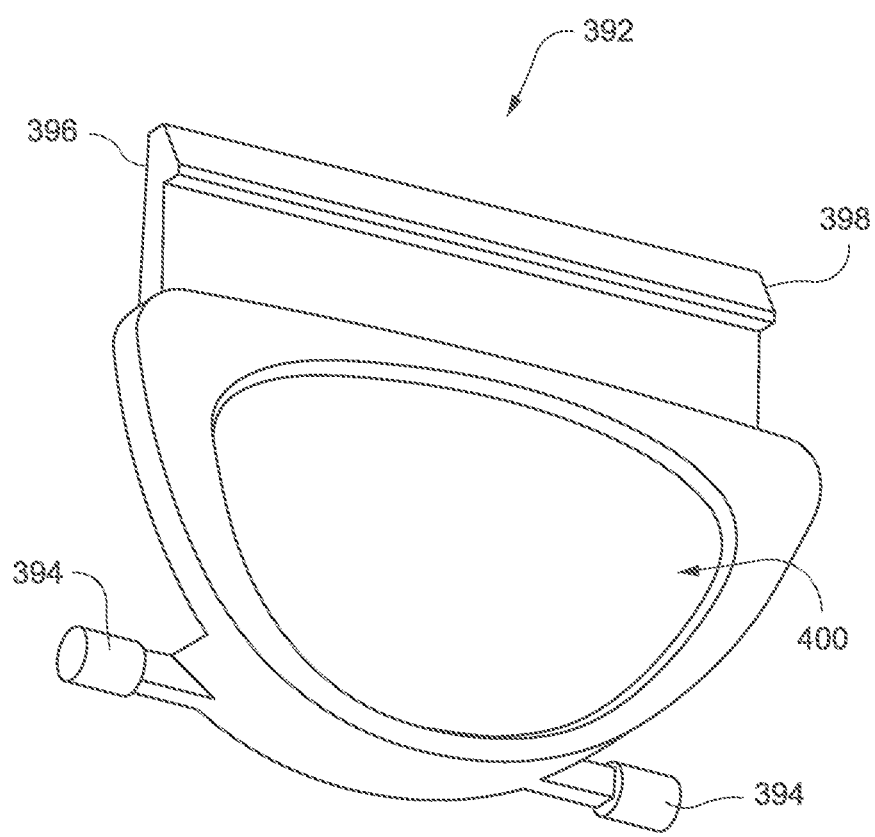
FIG. 36 is a perspective view from the front and below, of a lid catch of the humidifier of FIG. 22.
Figure 37:
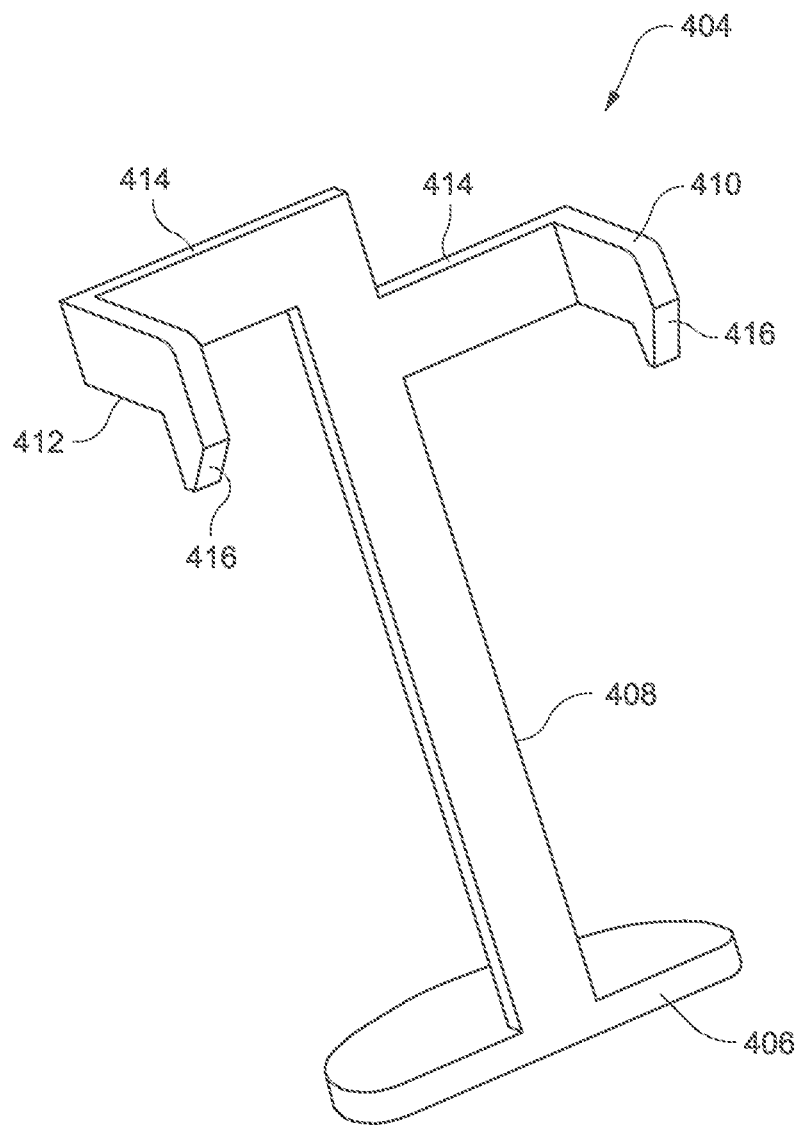
FIG. 37 is a perspective view of an interengagement catch of the humidifier of FIG. 22.

Referring to FIG. 36, there is shown a lid catch 392. The catch 392 has a pair of laterally projecting axles 394 and a catch formation 396. An upper front part 398 of the catch formation 396 is chamfered. A centre portion 400 of the lid catch 392 is recessed and constitutes a thumb actuation pad.

The lid catch 392 is mounted on the brackets 256 at the front of the horizontally extending portion 244 of the second cradle component 204. This is achieved by the axles 394 being accommodated in the slots 258. When the second cradle component 204 is assembled to the first cradle component 202 as described above, the centre portion 400 of the lid catch 392 is slid into place in the aperture 216 at the front of the horizontally extending portion 206 of the first cradle component 202. It will be appreciated that the aperture 216 is shaped complementarily to the centre portion 400, so that the centre portion is surrounded by that part of the horizontally extending portion 206 which defines the aperture 216. The catch formation 396 then projects above the upper edge of the outer wall 210 of the horizontally extending portion 206.

A suitable biasing means, which may be in the form of a coil spring or other type of spring (not shown), may be provided to urge the catch formation 396 in a forward direction. The lid 318 is provided, at its front extremity, with a suitable recess, indentation, ledge or the like (not shown) which is configured to snap-engage with the catch formation 396 when the lid is closed in the direction of the arrow 390 in FIG. 33, to secure the lid in a closed position. The chamfer 398 causes the catch formation 396 to move backwards against the force of the biasing means, to allow the lid 318 to close before the catch formation snaps back to its locking position. To open the lid 318, the centre portion 400 must be depressed to release the catch formation 396 from the lid 318. The finger-grip formation 344 facilitates opening of the lid.

The humidifier according to the present embodiment may be used in conjunction with a flow generator similar to the flow generator 50 described above. The humidifier is releasably fixed to the flow generator by means of a catch 404 (see FIG. 37). The catch 404 includes an actuation portion 406, a central bar 408 extending from the actuation portion, and a pair of catch formations 410 and 412 which are supported on support bars 414 which extend laterally from the central bar. It will be noted that each of the catch formations 410 and 412 is provided with a chamfer 416.

The way that the catch 404 is configured to be mounted will depend on the particular embodiment. For example, the catch 404 may be mounted on either the first cradle component 202 or the second cradle component 204, with the catch formations 410 and 412 extending through the slots 262 in the vertically extending portion 246 of the second cradle component. Suitable biasing means such as a spring (not shown) may be provided to urge the catch 404 in a downward direction. As the humidifier is engaged with the flow generator, suitable slots or other formations on the flow generator engage with the catch formations 410 and 412. The chamfers 416 allow the catch formations 410 and 412, and hence the catch 404 as a whole, to ride over the relevant formation on the flow generator so as to move upwards against the urging of the biasing means, so that the catch formations can snap-engage with the flow generator. To release the humidifier from the flow generator, the actuation portion 406 can be depressed from a position below the humidifier, in an upward direction, to release the catch formations 410 and 412.

When the humidifier according to the present embodiment is to be used, the lid 318 can be opened as described above, and the water receptacle 294 removed to allow filling thereof with water. Suitable markings (not shown) can be provided on the water receptacle 294 to indicate a maximum level to which the it is to be filled with water.

A microswitch (not shown) or other sensing means may be provided to turn off power to the heater pad when the lid is opened, and/or when the water receptacle is removed.

The water receptacle 294 can then be replaced, so that it rests upon the heater pad (not shown) of the horizontally extending portion 244 of the second cradle component 204. The lid 318 is then closed and the humidifier can be allowed to operate in conjunction with the flow generator.

A suitable flow generator is one having an air outlet pipe which is aligned for engagement with the circular aperture 260 in the vertically extending portion 246 of the second cradle component 204. Thus, air from the flow generator is forced through the circular aperture 260, via the circular aperture 284 of the airway seal 280 and along the passage defined by the airway seal and the rearwardly projecting wall 236 of the first cradle component 202, through the rectangular aperture 226.

The lid 318 and frame formation 366 of the lid seal 350 are configured such that when the lid 318 is in its closed position as described above, the frame formation presses and seals against the rim 228 defining the aperture. It will be appreciated that the angle at which the rim 228 slopes corresponds to the angle of the rim 330 of the rectangular tubular structure 328 of the lid 318, and also the angle at which the frame formation 366 extends, to facilitate this sealing engagement. Thus, air passing from the flow generator via the rectangular aperture 226 passes through the aperture 374 of the seal frame formation 366, and though the passage 332 in the tubular structure 328 of the lid 318, into the space defined by the internal region 334 of the lid and the lid seal 350. This air then travels over the upper surface of the centre wall 352 of the lid seal 350 and then passes downwardly, through the inlet opening 376 and into the headspace of the water receptacle 294.

Where the lid seal 350 includes an inwardly curved sealing flange 388 as described above, the pressure of the air within the headspace of water receptacle from the flow generator serves to force the extension portion outwards, and hence downwards, so as to increase the sealing effect against the flange 310 of the water receptacle 294. The flexibility of the lid seal 350, especially where it includes the sealing flange 388, provides for a certain amount of play of the lid 318 while maintaining the sealing effect.

Once the air from the flow generator passes via the inlet opening 376 of the lid seal 350 into the water receptacle, the air then travels across the surface of the water in the water receptacle so that the air becomes humidified. The heating of the water by the heating element enhances this humidification. The air then exits the water receptacle 294 by passing through the outlet opening 378 in the lid seal 350, and then through the passage 340 of the pipe 336 in the lid 318. As indicated, the pipe 336 is attached to a suitable hose (not shown) for supplying the humidified air to a patient.

In addition to those features and advantages already described, the components and features of the humidifier according to the present embodiment have various advantages.

By providing the top seal to the water receptacle as part of the humidifier lid, improved simplicity of use is achieved while minimising the risk of spillage of water. Furthermore, like the first-described embodiment of the humidifier, the humidifier of FIGS. 22-38 is configured to reduce the risk of water backflow into the flow generator, for example by the relative positioning of the opening 376 and the aperture 226 and the height differential between the aperture 226 and the air outlet of the flow generator. Also, the shape of the air path defined by the seal 280—including an upper portion which is above the aperture 226 in the first cradle component— reduces the possibility of backflow from splashing of water if the user uses a jug or similar to fill the water receptacle in situ, as the water will flow back out of the aperture 226 rather than back through to the circular aperture 260 in the second cradle component.

In addition, the recess 364 and the forwardly projecting face 387 in the lid seal 350 are adapted to collect condensation which may form in the lid cavity and the headspace of the water receptacle, preventing backflow of this condensation to the flow generator when the lid is opened.

Furthermore, the configuration of the first and second cradle components 202 and 204 and is adapted to allow fitting together in a vertical orientation, to minimise the need for reorientation during assembly of the humidifier unit on the production line.

In addition, the resilience of the connection between the lid and the water receptacle, provided by the lid seal, is adapted to maintain downwards pressure on the water receptacle when the lid is closed, to maintain good heat-transfer contact between the base of the water receptacle and the heater pad without the added complexity and expense of spring-loaded mounting of the heater pad.

Second Further Embodiment of the Humidifier

FIGS. 39 to 49B relate to a humidifier according to yet a further embodiment of the invention. The humidifier according to this embodiment has components generally corresponding to those of the previous embodiment, although the specifics of the components differ, as will be apparent from the description below.

The humidifier according to the present embodiment includes a first cradle component 602 which has a horizontally extending portion 604 and a vertically extending portion 606. The horizontally extending portion 604 has an outer wall 608, and the vertically extending portion 606 has a front wall 610.

The front wall 610 and outer wall 608 together define an opening 612 at the bottom of the first cradle component 602, and the front wall has a recess 614 at its lower edge.

At each side of the first cradle component 602, the upper edge of the outer wall 608 continues rearwardly of the front wall 610 and curves upwards to define a forward projecting, face 616. The outer wall 608 continues rearwardly of each face 616 to form rear side-walls 608.1. The first cradle component 602 also has an upper wall 618 which extends from the front wall 610 and side-walls 608.1. The upper wall 618 has a rear recess 620.

Figure 39:
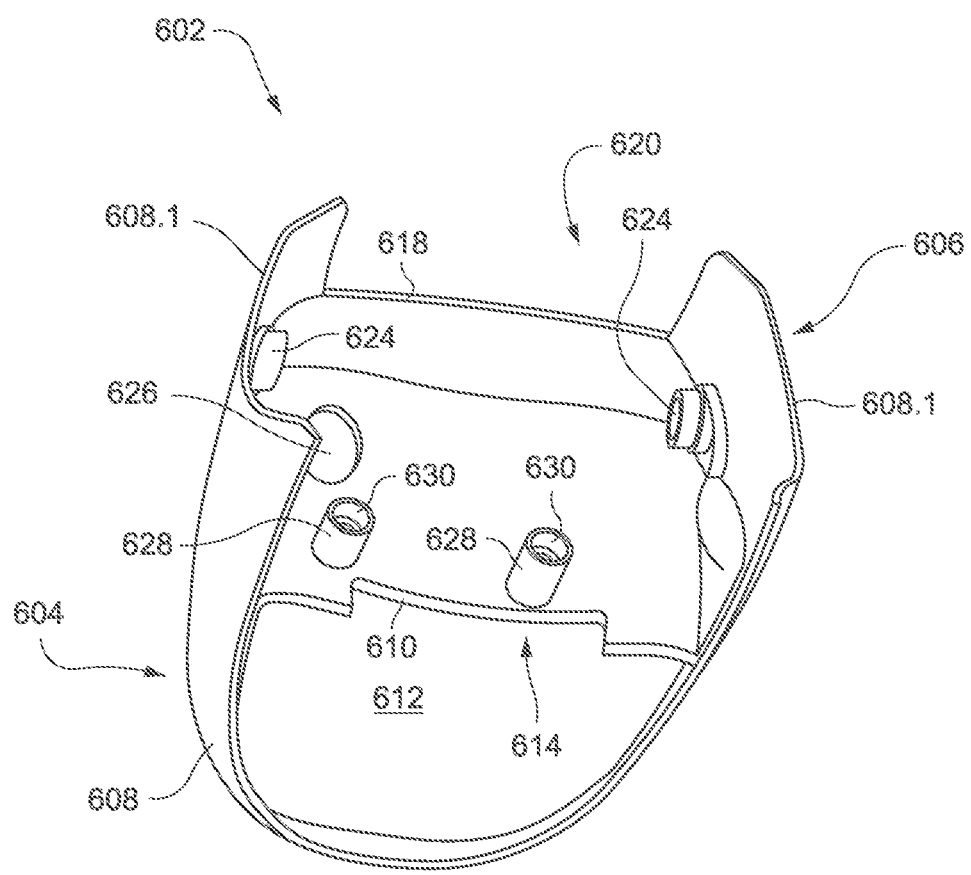
FIG. 39 is a perspective view from behind and below of a first cradle component of a humidifier according to yet a further embodiment.

Immediately in front of the face 616 at each side of the first cradle component 602, adjacent the upper wall 618, there is a socket 622. Adjacent each socket 622 there is a further, smaller socket, referred to below as a stud socket 623. The inside of each socket 622 and stud socket 623 is closed by a formation 624 as seen in FIG. 39.

The front wall 610 defines a circular aperture 626 and has a pair of tubular protrusions 628 extending rearwardly from the rear surface of the front wall. Each protrusion 628 has a central passage 630.

Figure 41:
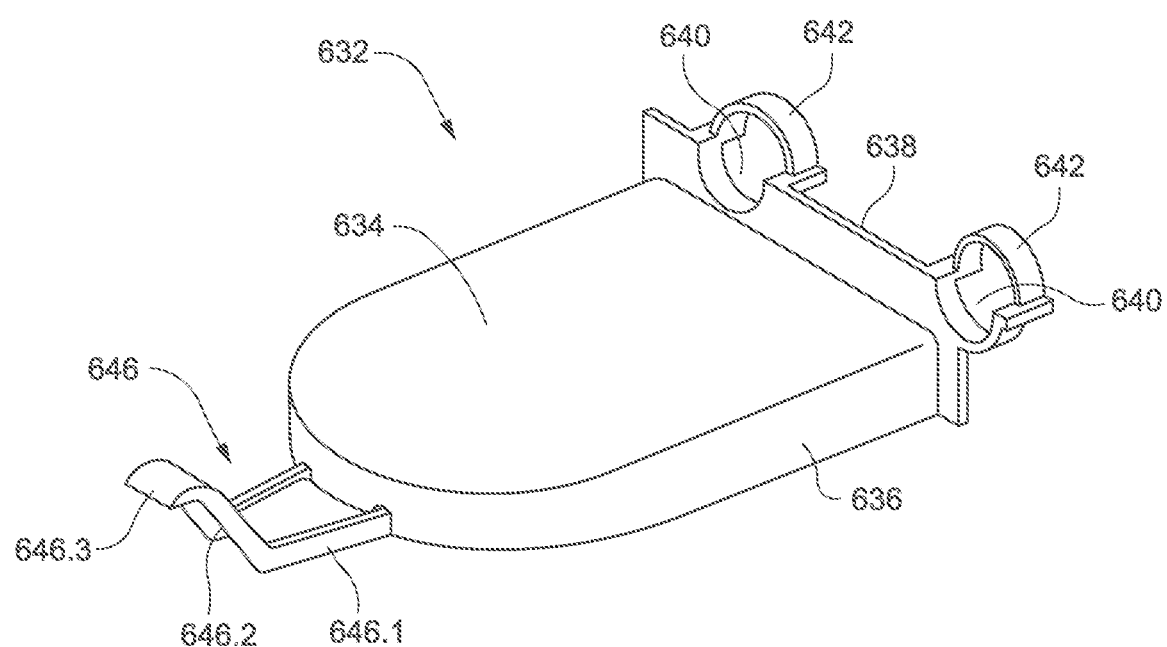
FIG. 41 is a perspective view from the front and above of a second cradle component of the humidifier of FIG. 39.
Figure 42:
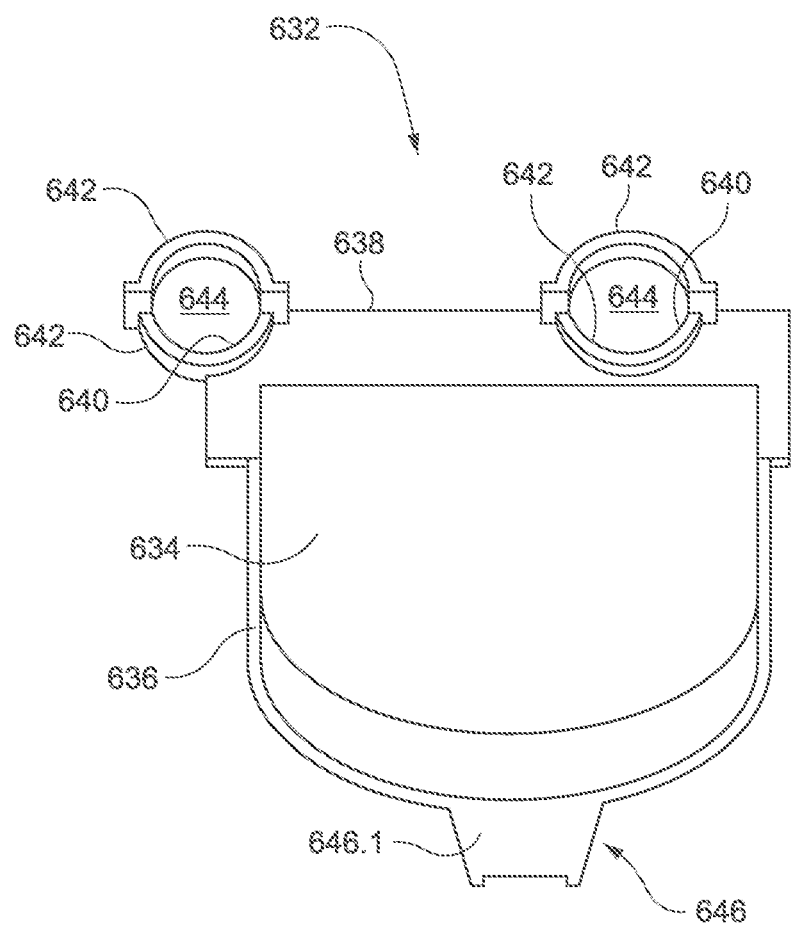
FIG. 42 is a perspective view from the rear and below of the component of FIG. 41.

Referring to FIGS. 41 and 42, there is shown a second cradle component 632. The second cradle component 632 has an upper wall 634 and a downwardly extending wall 636 extending from the upper wall. At the rear of the upper wall 634 is a flange 638. The flange 638 defines two semi-circular notches 640 with two pairs of semi-circular arches 642 being attached, at each side of the second cradle component 632, to the flange 638. Thus, each pair of arches 642 and their corresponding notches 640 define a circular passage 644.

At the front extremity of the wall 636 there is provided a forward extending tab 646. The tab 646 is of dog-legged shaped, having a first tab portion 646.1 extending from the wall 636, a second tab portion 646.2 sloping upwards from the first portion, and a third tab portion 646.3 extending forwards from the second tab portion.

The second cradle component 632 is configured to accommodate, below the upper wall 634 and within bounds of the wall 636, a heater pad or other heating means such as an induction heater, for causing heating of the water in the humidifier water container.

Figure 43:
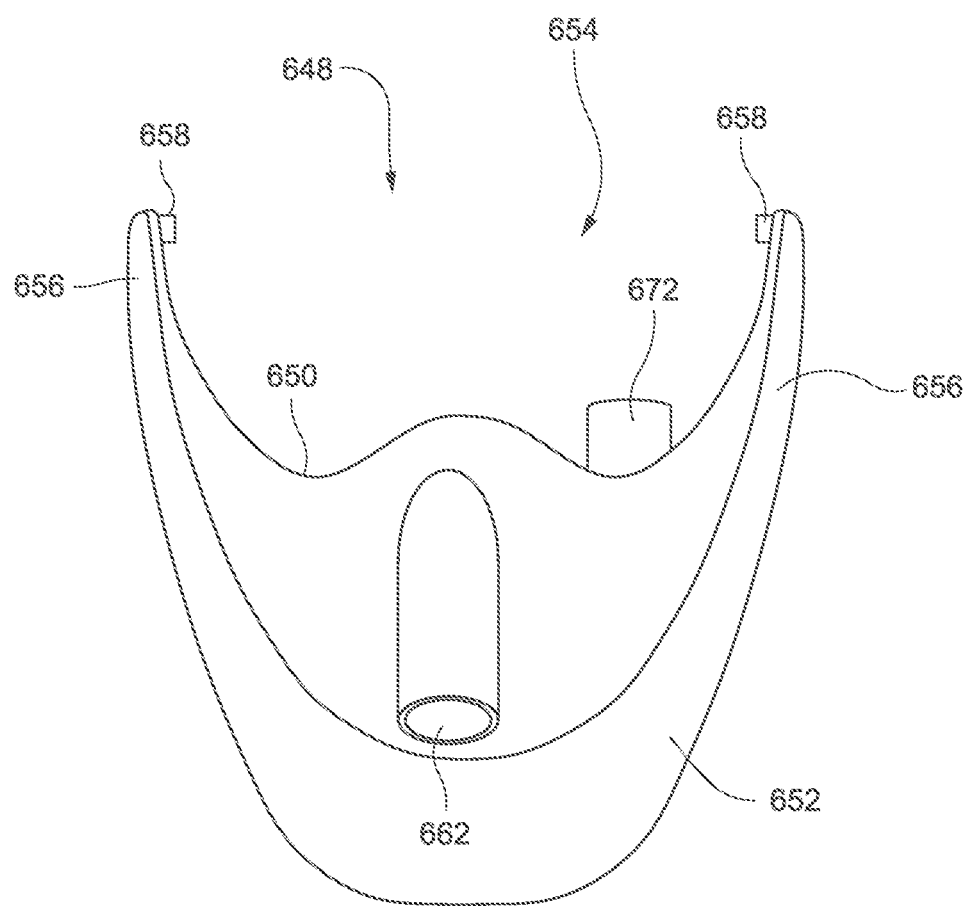
FIG. 43 is a plan view of a lid of the humidifier of FIG. 39.
Figure 44:
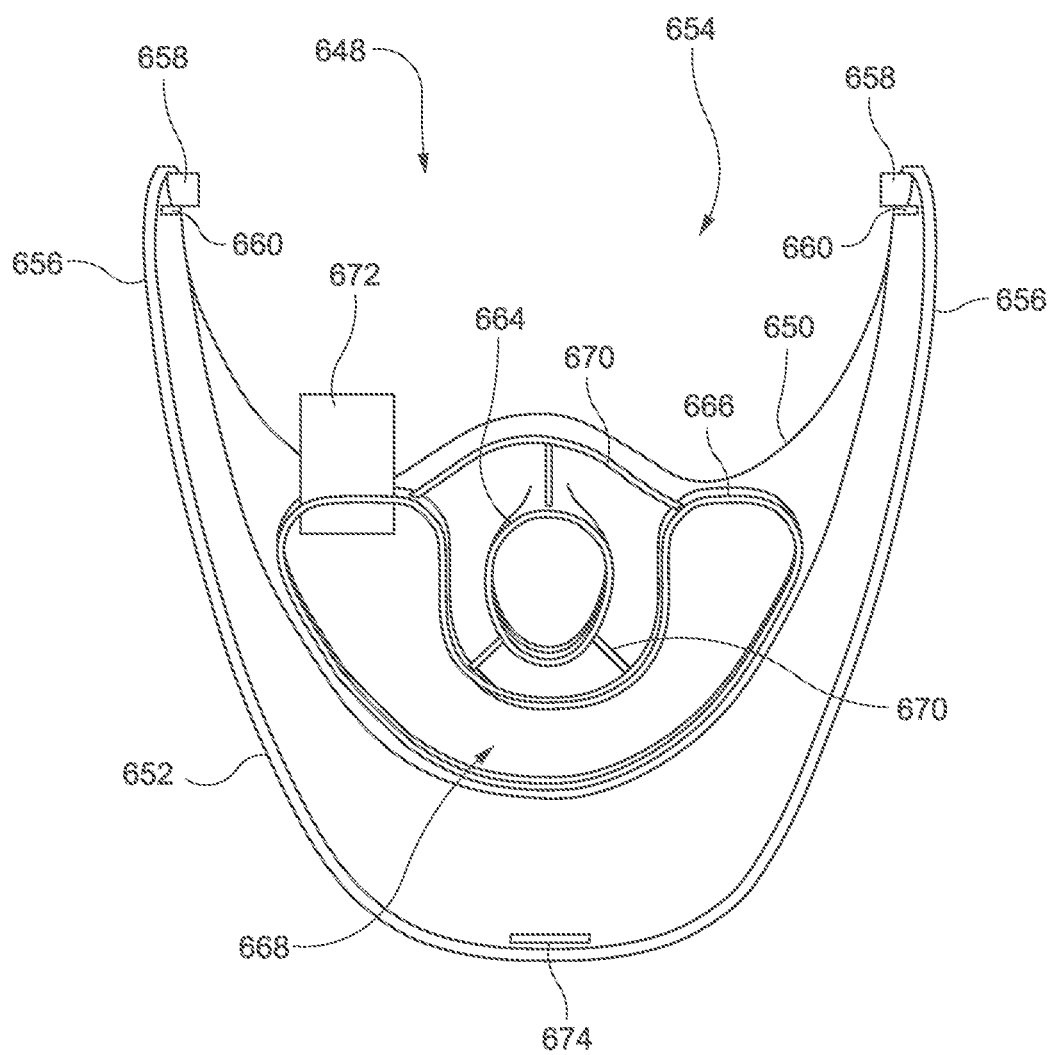
FIG. 44 is an underneath view of the lid of FIG. 43.
Figure 45:
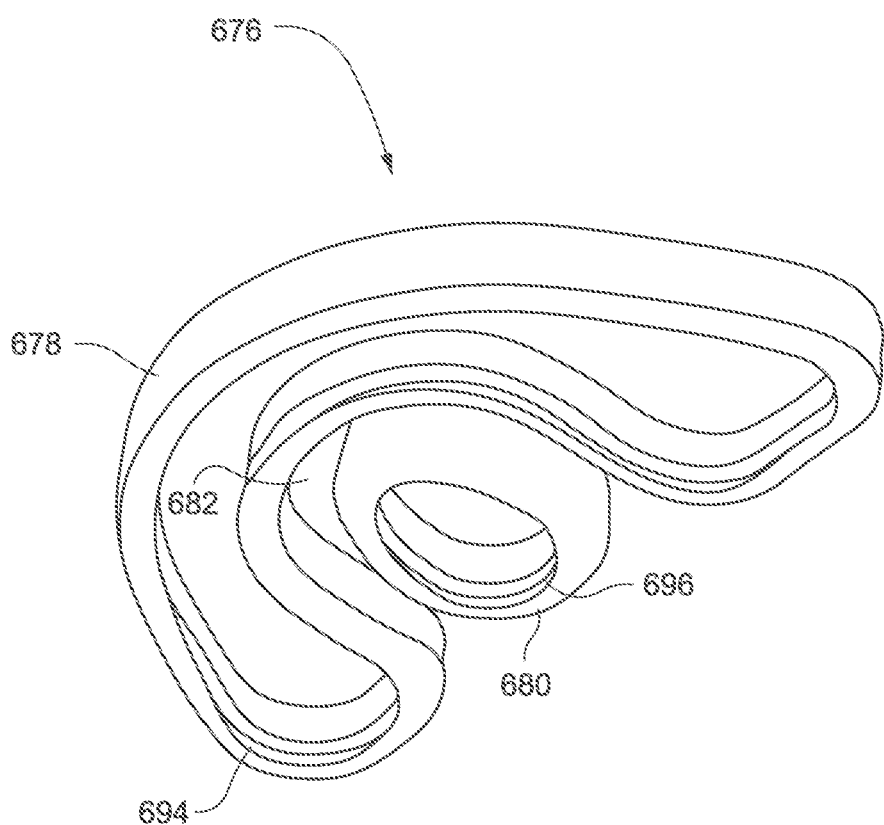
FIG. 45 is a perspective view from the front and below of a seal forming part of the humidifier of FIG. 39.

Referring to FIGS. 43 and 44, there is shown a lid 648 of the humidifier according to the present embodiment. The lid 648 has an upper wall 650 and a front wall 652 which extends downwards, and outwardly, from the upper wall. The upper wall 650 has a recess 654 at its rear side, such that the part of the upper wall and front wall 652 on each side of the recess constitutes a rearwardly projecting arm 656. At the rearmost extremity of each arm 656 there is an inwardly projecting hub 658. The hubs 658 are configured to be received in the sockets 622 of the first cradle component 602 such that each hub and its corresponding socket constitute a hinge connection, for attaching the lid 648 to the first cradle component.

The lower edge of each arm 656 is shaped complementarily to the shape of the upper portion of the face 616 to accommodate that part of the arm when the lid 648 is in a closed position, as will be described further below.

Immediately adjacent each hub 658 there is provided an inwardly projecting stud 660, each stud being configured to snap-engage into a respective stud socket 623. This is to restrain the lid 648 against opening too easily.

The lid 648 includes a humidified air outlet pipe 662 which passes through the upper wall 650 and extends upwards and forwards from the top of the upper wall. The pipe 662 continues below the lower surface of the upper wall 650 to define a spigot 664.

Extending downwards from the lower surface of the upper wall 650 is a wall 666 which is configured to define a closed path and hence a U-shaped enclosed region 668 within the confines of the wall. Strengthening webs 670 are provided to brace the wall 666 and spigot 664 relative to the upper wall 650, to provide added strength.

There is provided a pipe 672 which passes through a rear part of the wall 666 at one end of the U-shaped enclosed region 668.

At the front extremity of the front wall 652, that is, adjacent the lower edge of that wall, there is provided a recessed notch 674 on the rear (inner) surface of that wall.

A resilient sealing member 676 of elastomeric or other suitable resilient material (see FIGS. 45 and 46) is mounted on the lower extremities of the wall 666 and spigot 664. The sealing member 676 has a first U-shaped portion 678 of a shape corresponding to that of the wall 666, and a second portion 680 of elliptical shape, corresponding to the downwardly projecting shape of the lower extremity of the spigot 664. The first and second portions 678 and 680, respectively, are joined to each other by a web 682.

Figure 46:
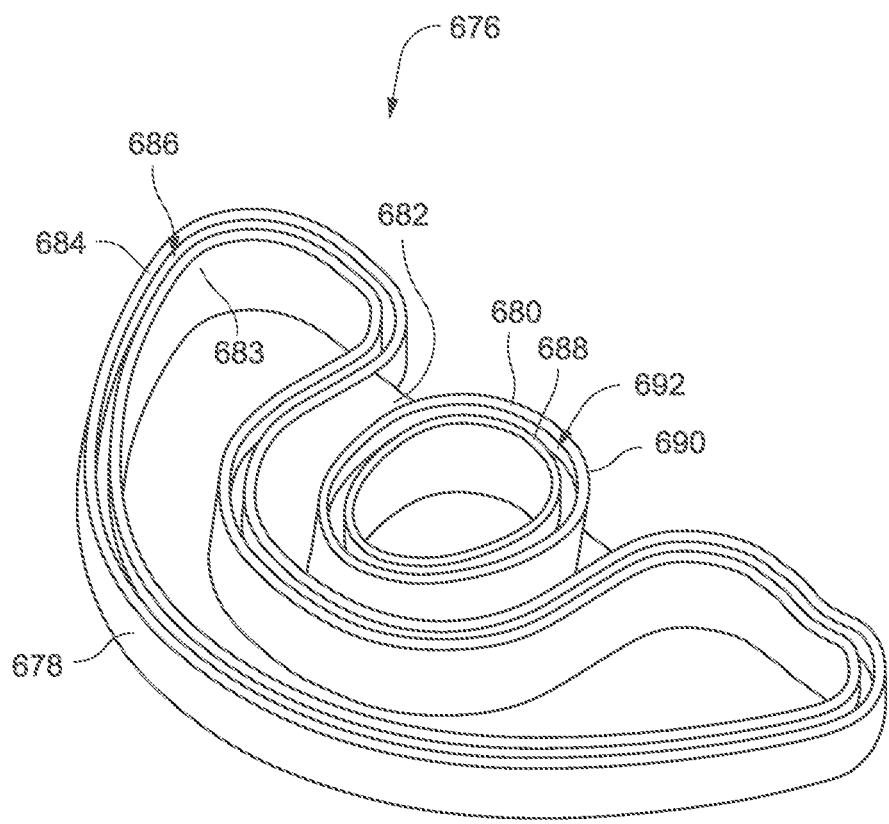
FIG. 46 is a perspective view from the front and above of the seal of FIG. 45.

As can be seen in FIG. 46, the first portion 678 has an inner wall 683 and an outer wall 684, the inner and outer walls defining a channel 686 between them. Similarly, the second portion 680 has an inner wall 688 and an outer wall 690, these inner and outer wall defining a channel 692 between them. The sealing member 676 is engaged with the lid 648 by way of the wall 666 being received as a press-fit in the channel 686, and the spigot 664 being received as a press-fit in the channel 692.

Figure 46A:
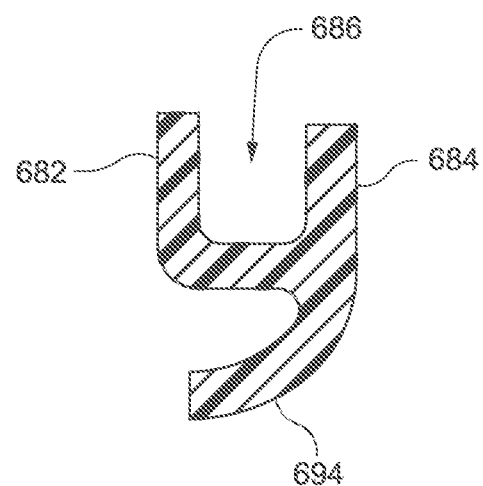
FIG. 46A is a schematic section view through the seal of FIG. 46.

The sealing member 676, at the bottom of each of the first and second portions 678 and 680, has a sealing flange 694 and 696, respectively. The sealing flange 694 (which is similar to the sealing flange 696) is shown schematically in cross-section in FIG. 46A.

Figure 47:
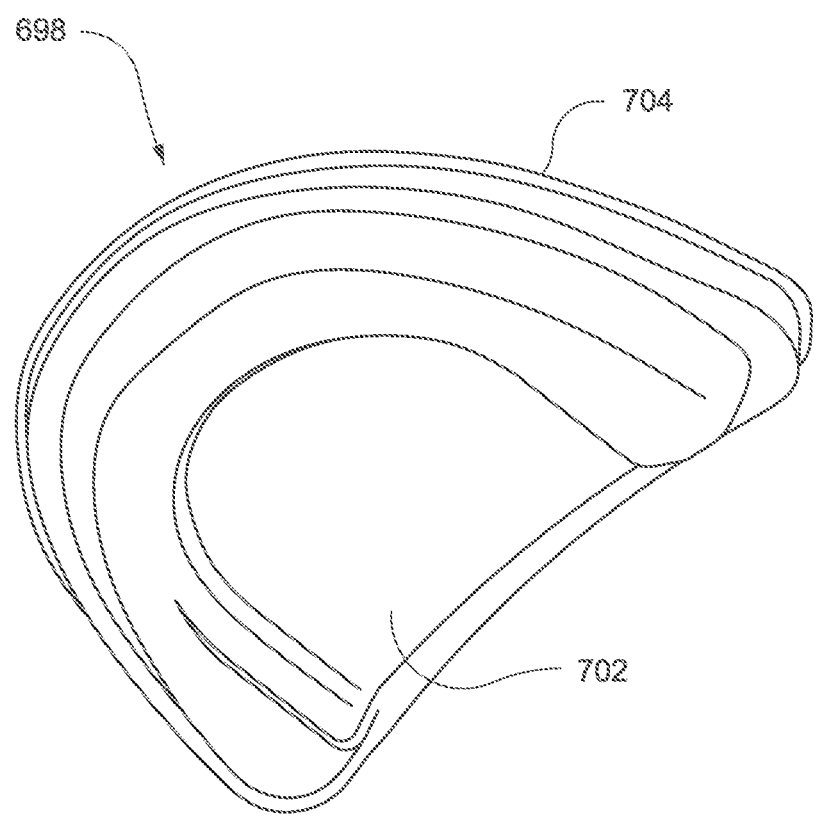
FIG. 47 is a perspective view from the front and below of a lower component of a water receptacle of the humidifier of FIG. 39.
Figure 48:
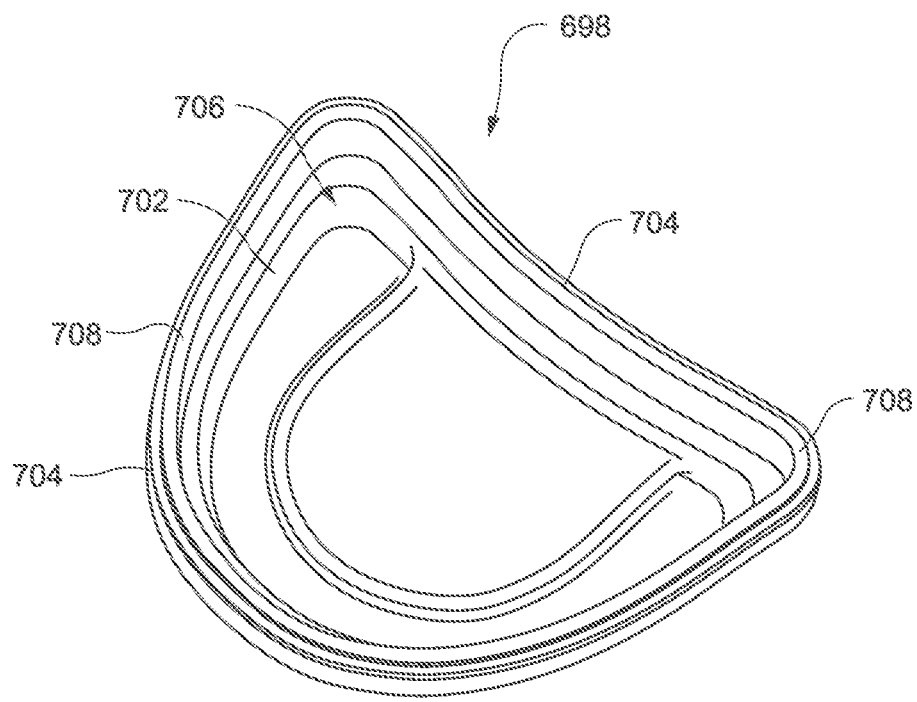
FIG. 48 is a perspective view from the front and above of the component of FIG. 47.
Figure 49:
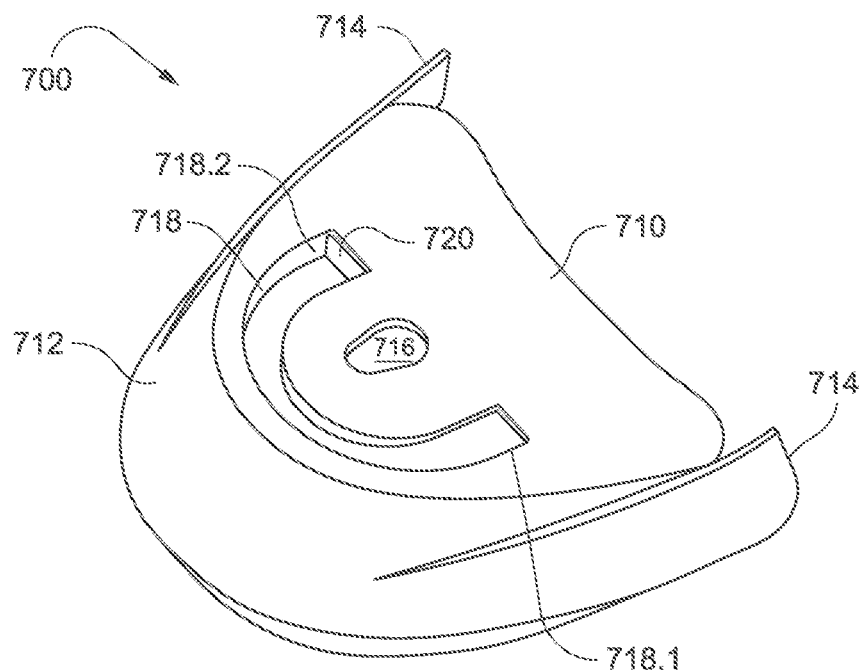
FIG. 49 is a perspective view from the front and above of an upper component of the water receptacle of FIG. 47.

Referring to FIGS. 47 to 49, there are shown a lower component 698 and an upper component 700 of a water receptacle forming part of the humidifier according to the present embodiment. The lower component 698 has a lower wall 702 and side walls 704 extending upwardly from the lower wall. A U-shaped recess 706 is provided in the lower wall 702, to assist positioning of the receptacle on the heater pad upper wall 634. At the upper edge of the side walls 704 there are provided rebates 708 on the outer edges of the walls. It will be appreciated that the side walls 704 together form a continuous wall.

The upper component 700 has an upper wall 710 and front wall 712 extending downwardly from the edges at the sides and front of the upper wall, and a rear wall (not shown). The front wall 712 extends beyond the rearmost extremity of the upper wall 710 to form a pair of side wings 714.

A roughly elliptical aperture 716 opens through the upper wall 710. In addition, there is provided an arc-shaped recess 718 which extends around the aperture 716, and which increases in depth from one end 718.1 to an opposite end 718.2. At the end 718.2 there is provided a further aperture 720 which opens out below the upper wall 710 to the headspace of the water receptacle.

The humidifier according to the present embodiment is assembled by sliding the second cradle component 632 through the recess 614 in the front wall 610 of the first cradle component 602 until the tab 646 engages with the forwardmost part of the outer wall 608. In this position, the third tab portion 646.3 extends over the upper edge of the outer wall 608. As the second cradle component 632 is slid into place as described, the protrusions 628 projecting from the rear of the front wall 610 protrude through the passages 644 defined by the flange 638 and arches 642 of the second cradle component 632. Fasteners (not shown) such as screws or bolts can be used to secure the second cradle component 632 to the first cradle component 602. This is achieved by screwing the fasteners into the passages 630 of the protrusions 628 so that the heads of the fasteners hold the second cradle component 632 captive.

The lid 648 is engaged with the first cradle component 602 by manipulating the arms 656 so that the hubs 658 snap-engage into the sockets 622, so that each hub and the corresponding socket constitute a hinge. The lid 648 is thus capable of rotating relative to the first cradle component 602.

Figure 49A:
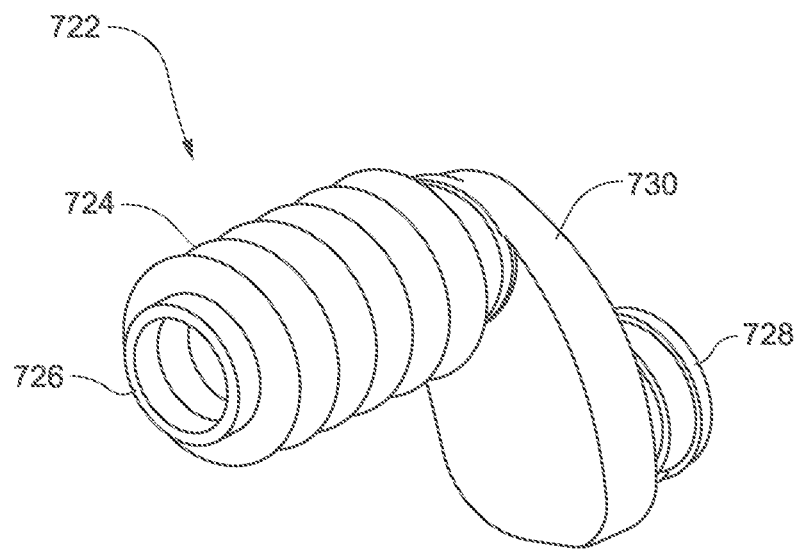
FIG. 49A is a perspective view from the front, of an air connector component of the humidifier of FIG. 39.
Figure 49B:
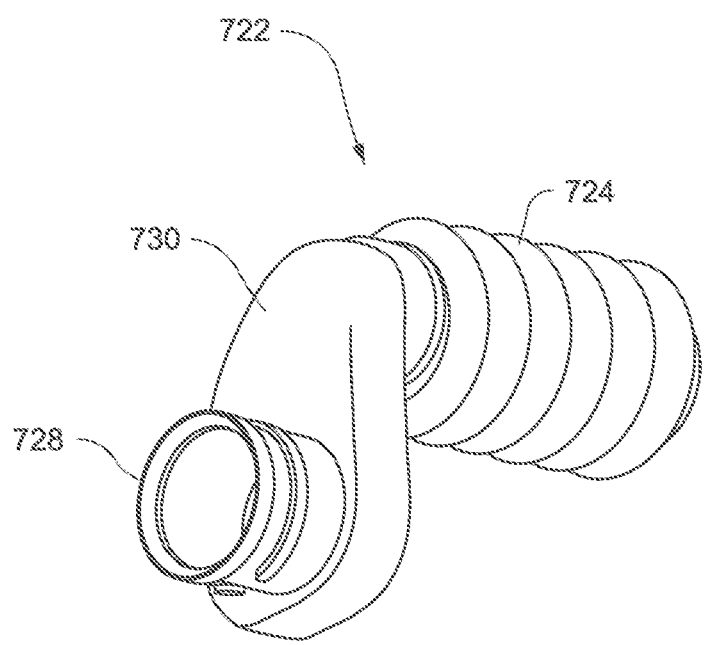
FIG. 49B is a perspective view from the rear, of the air connector component of FIG. 49A.

Also forming part of the humidifier according to the present embodiment is a flexible air connector component 722 as shown in FIGS. 49A and 49B. The air connector component 722 includes a first bellows-like flexible hose 724 having an end rim 726, and a second tube 728 extending in an opposite direction to the flexible pipe, the flexible pipe and second tube being interconnected by a connection chamber 730 which serves a generally similar function to seal 280 of FIGS. 34 and 35.

It will be noted that the configuration of the air connector component 722 is such that the flexible hose 724 and second tube 728 are arranged in a dog-leg configuration so as not to be in alignment with each other.

During assembly of the humidifier according to the present embodiment as was partly described above, the flexible hose 724 is passed through the circular aperture 626 in the front wall 610 until the front face of the connection chamber 730 abuts the rear face of the front wall. The air connector component 722 may then be fixed in place relative to the front wall 610 by suitable means (not shown). The end rim 726 is then engaged with the pipe 672 of the lid, by receiving this pipe as a press-fit, to create a flexible connection which can withstand opening and closing of the lid. The second tube 728 connects to the air outlet of the flow generator.

To form the water receptacle, the lower component 698 and upper component 700 thereof are fitted together, so that a lower edge of the front wall 712 of the upper component is accommodated in the rebate 708 of the lower component, which ensures that these components are sealed in a substantially watertight manner to each other. The assembled water receptacle can then be lowered onto the upper wall 634 of the second cradle component 632, this upper wall being disposed within the bounds of the outer wall 608 of the first cradle component 602. The shape of the front wall 712 of the upper component 700 of the water receptacle, and in particular the wings 714, is such that the water receptacle is accurately located in position by the outer wall 608 and front wall 610 of the first cradle component 602.

When the lid 648 (which was attached to the first cradle component 602 as described above) is rotated downwards about the hinges formed by the hubs 658 and sockets 622, the front tip of the third portion 646.3 of the tab 646 of the second cradle component 632 is received as a snap-fit in the notch 674 at the front of the lid to hold the lid closed.

Furthermore, the first portion 678 of the sealing member 676 forms a substantially watertight seal around the recess 718 in the top of the upper component 700 of the water receptacle. Similarly, the second portion 680 of the sealing member 676 forms a substantially water tight seal around the aperture 716 in the upper component 700 of the water receptacle. The watertightness of the seals is enhanced by the sealing flanges 694 and 696 of the first and second portions 678 and 680, respectively, of the sealing member 676.

In use, the water receptacle may be filled by first opening the lid 648 by disengaging the notch 674 from the third tab portion 646.3 and rotating the lid upwards relative to the first cradle component 602. Water can then be poured into the water receptacle via the aperture 716 in the upper component 700, whereafter the lid 648 can be closed again.

The humidifier according to the present embodiment can be used in conjunction with a flow generator similar to the flow generator 50 described above, and may be attached to the flow generator using a catch, and catch arrangement, similar to that described in relation to the catch 404 of the previous embodiment.

The humidifier according to the present embodiment is configured such that, when it is mounted on the flow generator, the second tube 728 of the air connector component 722 is engaged with an air outlet pipe of the flow generator. In use, air travels from the flow generator through the second tube 728, via the connection chamber 730 and then through the flexible hose 724 which, as described above, extends through the circular aperture 626 in the front wall 610 of the first cradle component 602. The air then travels through the pipe 672 of the lid 648 and into one end of the U-shaped enclosed region 668 defined by the wall 666 which depends from the lid. The flexibility of the flexible hose 724 allows the rim 726 to remain engaged with the pipe 672 while the lid 648 is opened or closed.

It will be appreciated that when the lid 648 is in its closed position, the sealing member 676, which is attached to the wall 666 and spigot 664, presses down on top of the upper component 700 of the water receptacle, as described above, so that the enclosed region 668 is not only enclosed by the wall 666 and the lower surface of the upper wall 650 of the lid, but also by the floor of the arc-shaped recess 718 defined in the upper component 700 of the water receptacle. Accordingly, the air from the flow generator which passes through the pipe 672 flows through the U-shaped path defined in the enclosed region 668 before passing through the further aperture 720 at the other end 718.2 of the recess 718, into the headspace of the water receptacle. The U-shape of the enclosed region 668 and recess 718 results in the air entering the water receptacle with a swirling motion which facilitates the humidifying of the air as it passes over the water in the receptacle.

The air then exits the water receptacle via the elliptical aperture 716. As described above, the second portion 680 of the sealing member 676 is sealed around the aperture 716 so that the humidified air exiting the water receptacle via the aperture 716 passes through the second portion of the sealing member, via the spigot 664 and out through the humidified air outlet pipe 662 at the top of the lid 648. A suitable hose (not shown) delivers the humidified air as required to a patient.

As the air supplied from the flow generator is under pressure, this pressure assists the sealing flange 694 of the sealing member 676 to create a firm seal around the recess 718 by forcing the extension portion outwards and downwards. A similar effect is created on the sealing flange 696 of the second portion 680 surrounding the elliptical aperture 716 due to the pressure of the air exiting the water receptacle.

(New Flow Generator Embodiment)

Figure 50:
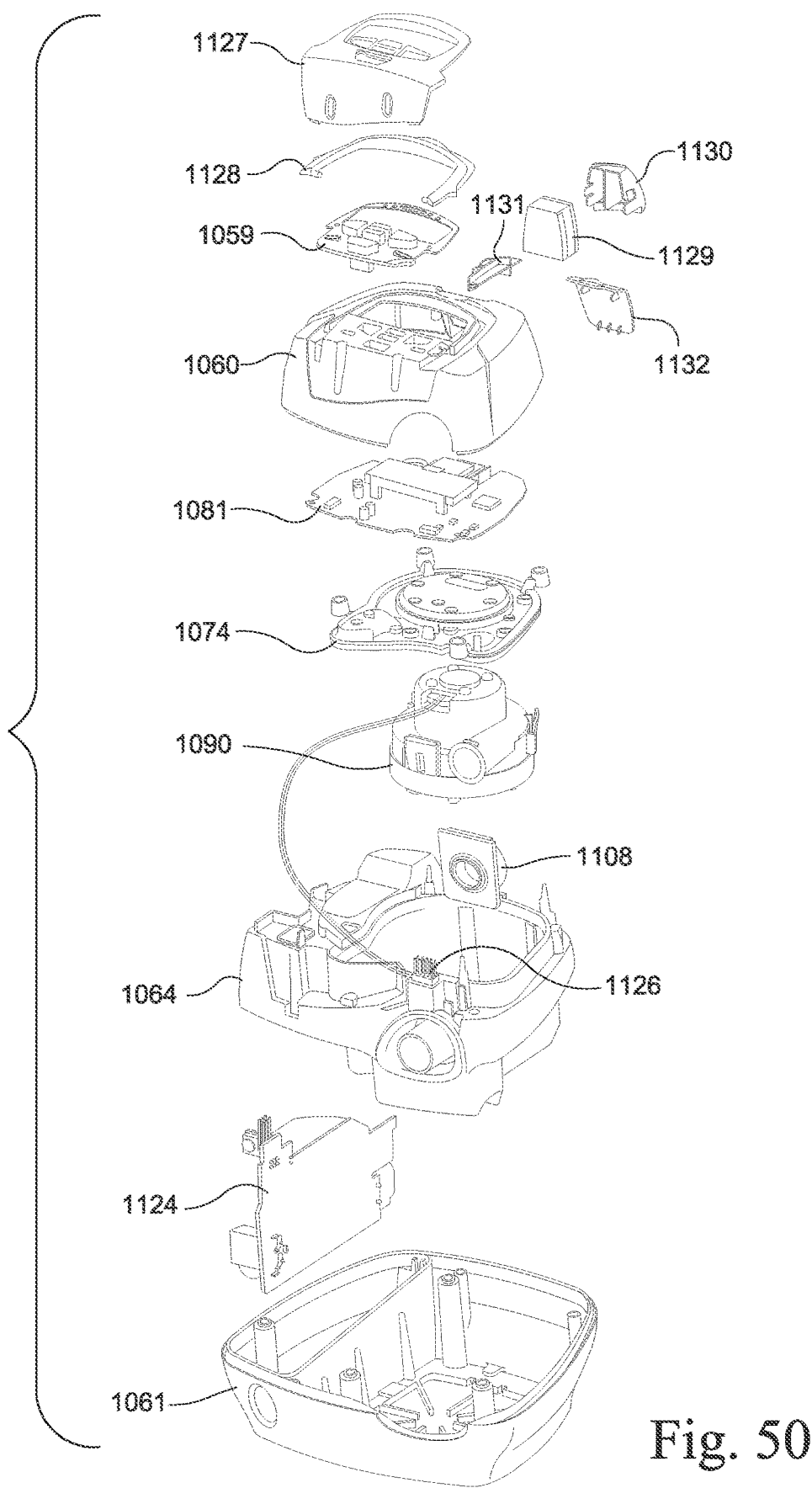
FIG. 50 is an exploded view of a further embodiment of the flow generator.
Figure 51:
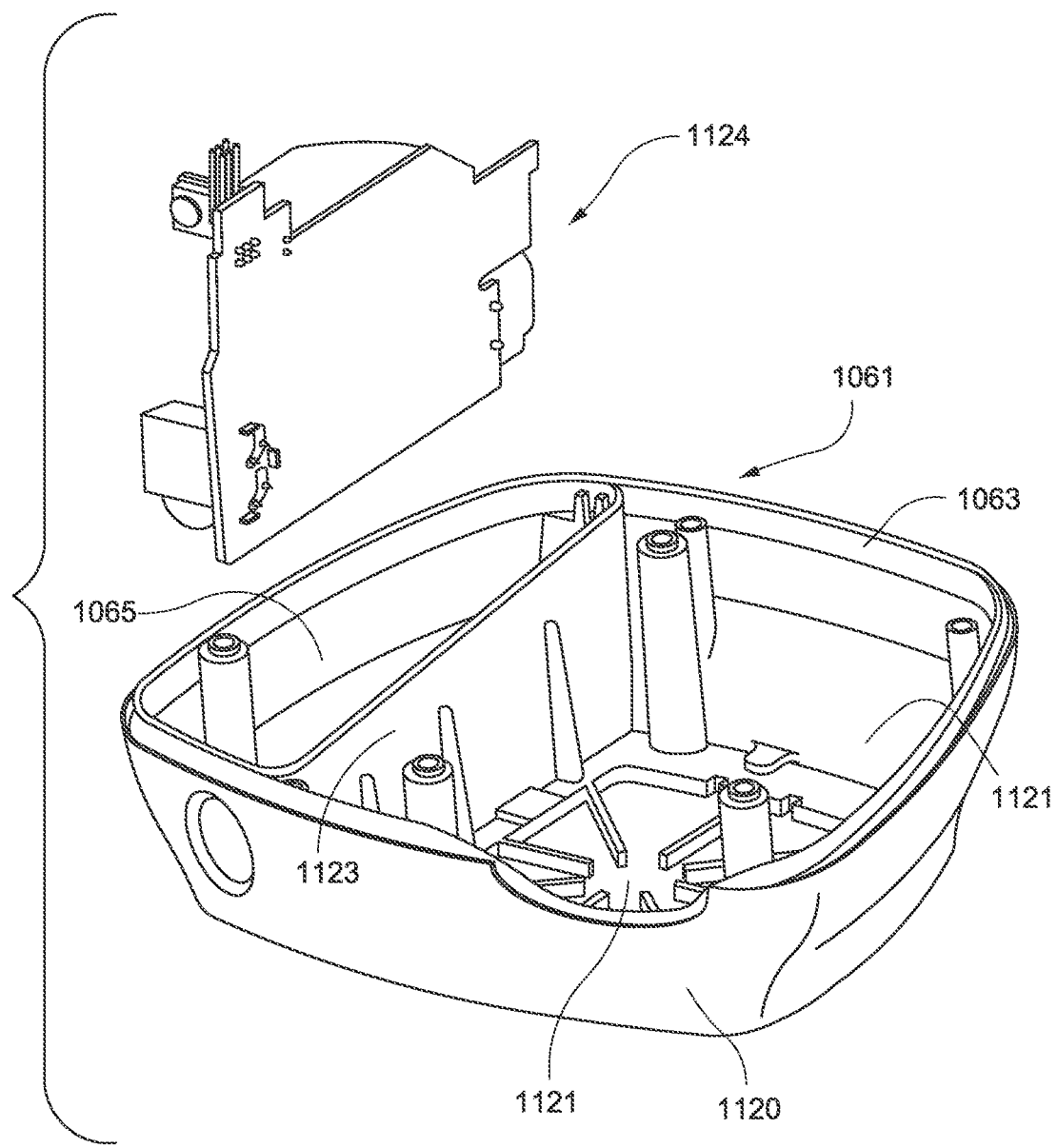
FIG. 51 is a more detailed illustration of the bottom case and power supply of FIG. 50.
Figure 52:
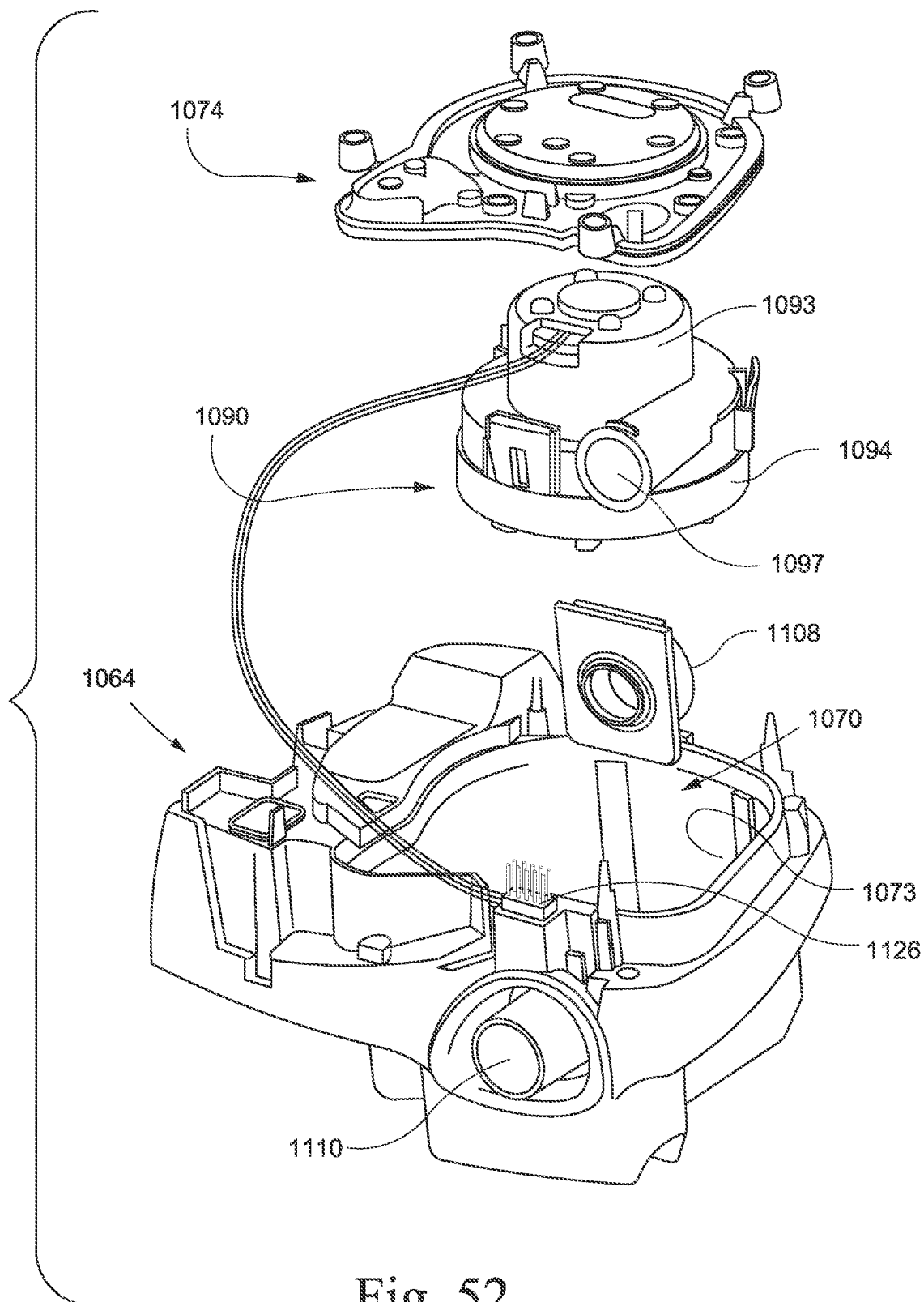
FIG. 52 is a more detailed illustration of the chassis, chassis lid and fan housing of FIG. 50.
Figure 53:
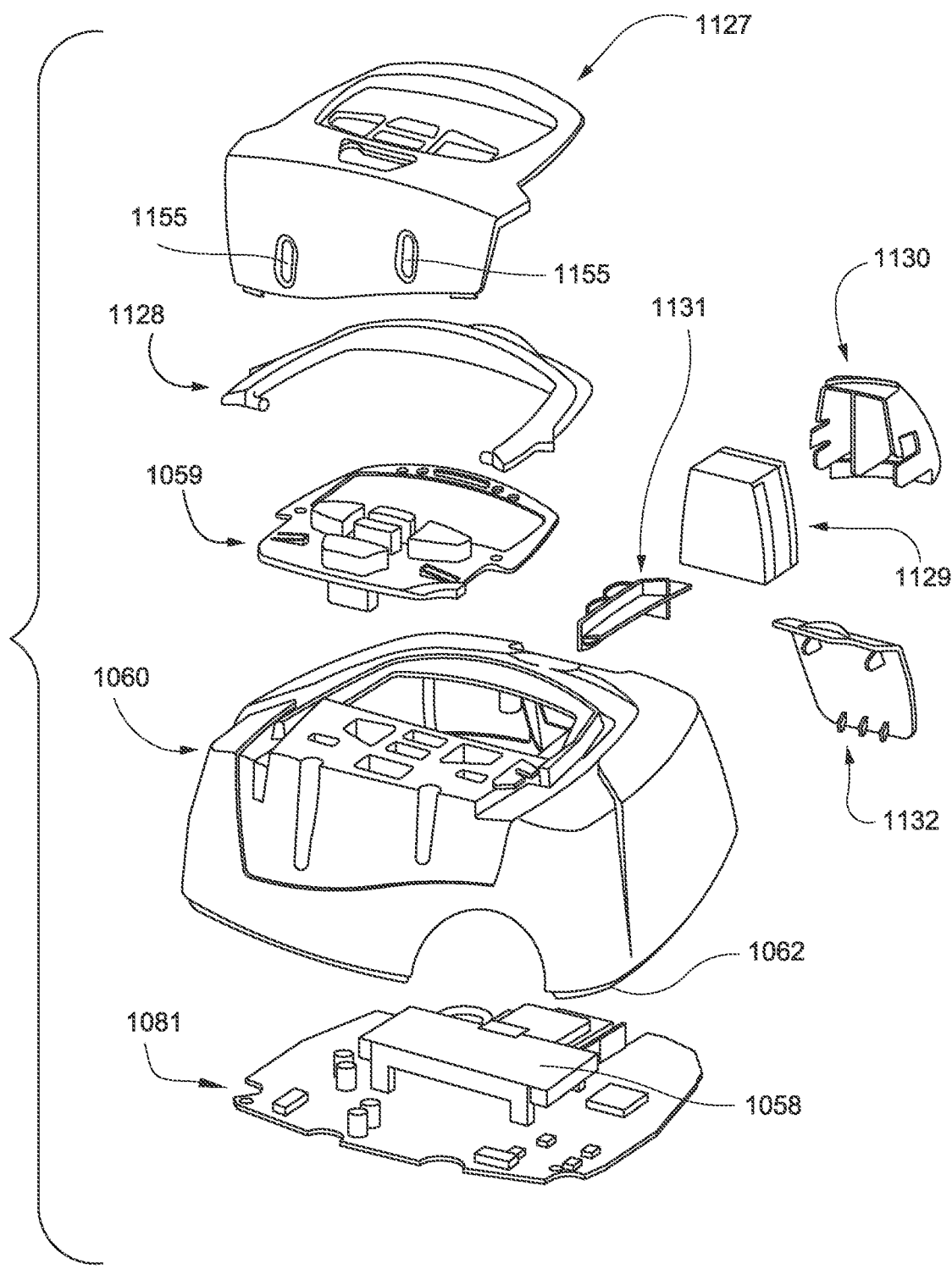
FIG. 53 is a more detailed illustration of the PCB, top case and exterior fittings of FIG. 50.

FIG. 50 is an exploded view of a flow generator 1050 according to a further embodiment, which is an alternative version of the flow generator 50 of the first embodiment. FIGS. 51-53 are more detailed views of components of the flow generator of FIG. 50.

The components and functioning of the flow generator 1050 are similar in many respects to that of FIGS. 1 to 21, and reference may be made to those figures and their description for more detailed description of the flow generator and its components.

The bottom case 1061 of flow generator 1050 has a shell 1120 of rigid plastics material, such polycarbonate/ABS blend, forming the structure of the case, integrally overmoulded with a lining 1121 of an elastomer such as a synthetic rubber which forms the seal 1063 between the top and bottom cases and the chassis 1064 and forms the external feet of the case (not shown). The lining 1121 also covers the internal surface of the chassis-receiving cavity 1122 of the bottom case and the dividing wall 1123 between the power supply cavity 1065 and chassis-receiving cavity, to reduce radiated noise levels from the flow generator by damping acoustic resonance of the walls.

A power supply unit 1124 is received in the power supply cavity 1065, for providing electrical power for operation of the fan, control functions and the humidifier heater pad.

The chassis 1064 forms the fan cavity 1070, inlet and outlet air flow paths and the top of the power supply cavity 1065. The fan cavity 1070 includes a metal liner tub 1073 insert moulded into the chassis as described above in relation to FIGS. 1 to 21. Preferred materials for the chassis and liner tub are polypropylene thermoplastic for the chassis and metal, preferably steel, for the liner tub. The applicant has found that by forming the fan cavity as a composite of metal and polymer—having a differential in density of greater than 5 times, preferably about 7-8 times, and also significantly different stiffness and damping properties—the resonance peaks of the composite structure are well damped so that noise generated by the fan is well-suppressed by the fan cavity construction.

The top of the fan cavity is formed by the chassis lid 1074, which is formed of a steel insert overmoulded with elastomer to provide acoustic damping.

The fan 1090 and fan housing 1093, 1094, substantially similar to the fan 90 shown in FIGS. 9 and 10, fit into the fan cavity 1070 of the chassis and connect to electrical connector 1126 on the chassis at the top of the fan cavity. Elastomer overmoulding of the base 1094 of the fan housing seals the housing, provides acoustic damping of the fan housing base and forms feet on the bottom of base to act as bump stops protecting the fan in case the unit is bumped or dropped.

An elastomeric outlet seal 1108 connects the volute outlet 1097 to the connecting nozzle 1110 of the flow generator chassis 1064. A Helmholtz resonator, as previously described, or a volume muffler cavity (not shown), may be incorporated in the chassis moulding to communicate with the air between the fan volute outlet 1097 and the nozzle 1110.

The printed circuit board 1081, which controls operation of the machine, sits on top of the chassis lid 1074 under the top case 1060 of the flow generator, and includes an LCD display 1058.

A keypad 1059, facia 1127, transport handle 1128 and slots 1155 attach to the top case 1060.

The top case further defines an air inlet to the flow generator, and a replaceable foam filter 1129 and filter cover 1130 fit to the top case 1060, held in place by an inlet wedge 1131. A blank cover 1132 clips in place over apertures in the case which align with ports on the PCB for communications, etc.

The illustrated flow generator construction and materials combinations are adapted to result in a compact CPAP flow generator unit of similar performance and noise characteristics to larger units—eg. capable of generating from 4-20 cmH2O pressure and a flow rate of 120 L/min and a total noise volume (radiated plus conducted) of less than 33 dbA, more preferably less than about 30 dbA, when operating at 10 cmH2O—in a flow generator unit having a total volume of about 2 litres or less.

(New Humidifier)

FIGS. 54 to 58B illustrate a modified version of the humidifier arrangement of FIGS. 39 to 49B, adapted to mate with the flow generator unit of FIGS. 50-53. The general arrangement of the humidifier components is similar to that of FIGS. 39 to 49B, including a front cover 1602 onto which is fitted a heater pad 1799 comprising and an upper part 1806 and a heater pad cover 1632 which supports a water tub (tub base 1698, seal 1699 and tub lid 1700) and a hinged humidifier lid 1648 which seals against the tub lid 1700 to form an air path into the tub through the tub lid. The heater pad cover 1632 has a upper surface 1634, a downwardly extending peripheral wall 1636 and a rear flange with a pair of attachment portions 1640 for attachment of the heater pad 1799 to tubular protrusions 1628 on the rear of the front cover 1602. The front of the heater pad cover 1632 has a forwardly extending tab 1646 of doglegged shape, which extends to the front of the humidifier cradle front cover 1602 to support the heater pad 1799 and also provide a catch for the humidifier lid 1648.

The floor of the tub base 1698 is of complementary shape to the heater pad 1799. The floor has a generally horizontal portion 1900 corresponding to the upper surface 1634 of the heater pad cover 1632 and a U-shaped portion below the level of the upper surface 1634, including a generally vertical heat transfer portion 1902 below the horizontal portion 1900 corresponding to the downwardly extending peripheral wall 1636 of the heater pad cover 1632. When the water tub is placed in the humidifier cradle and the hinged lid 1648 is closed, the water tub base 1698 is held in close contact with the heater pad 1799.

The lid 1648 has an upper wall 1650 and a front wall 1652 which extends downwards, and outwardly, from the upper wall 1650. The upper wall 1650 has a recess at its rear side, such that the part of the upper wall 1650 and front wall 1652 on each side of the recess constitutes a rearwardly projecting arm 1656. At the rearmost extremity of each arm 1656 there is an inwardly projecting hub 1658. The hubs 1658 are configured to be received in the sockets 1622 of the humidifier front cover 1602 such that each hub 1658 and its corresponding socket 1622 constitute a hinge connection, for attaching the lid 1648 to the front cover 1602.

The lid 1648 includes a humidified air outlet pipe 1662 which passes through the upper wall 1650 and extends upwards and forwards at an acute angle from the top of the upper wall 1650. The pipe 1662 continues below the lower surface of the upper wall 1650 to define an elliptical rim 1664.

Extending downwards from the lower surface of the upper wall 1650 is a wall 1666 which is configured to define a closed path and hence a U-shaped enclosed region 1668 within the confines of the wall 1666.

At the front extremity of the front wall 1652, that is, adjacent the lower edge of that wall, there is provided a recessed notch 1674 on the rear (inner) surface of that wall, for snap-fit engagement with the tab 1646 of the heater pad cover 1632 to act as the catch for the lid 1648. The lid 1648 may be opened by flexing the assembly to release the tab 1646 from the notch 1674.

Figure 54:
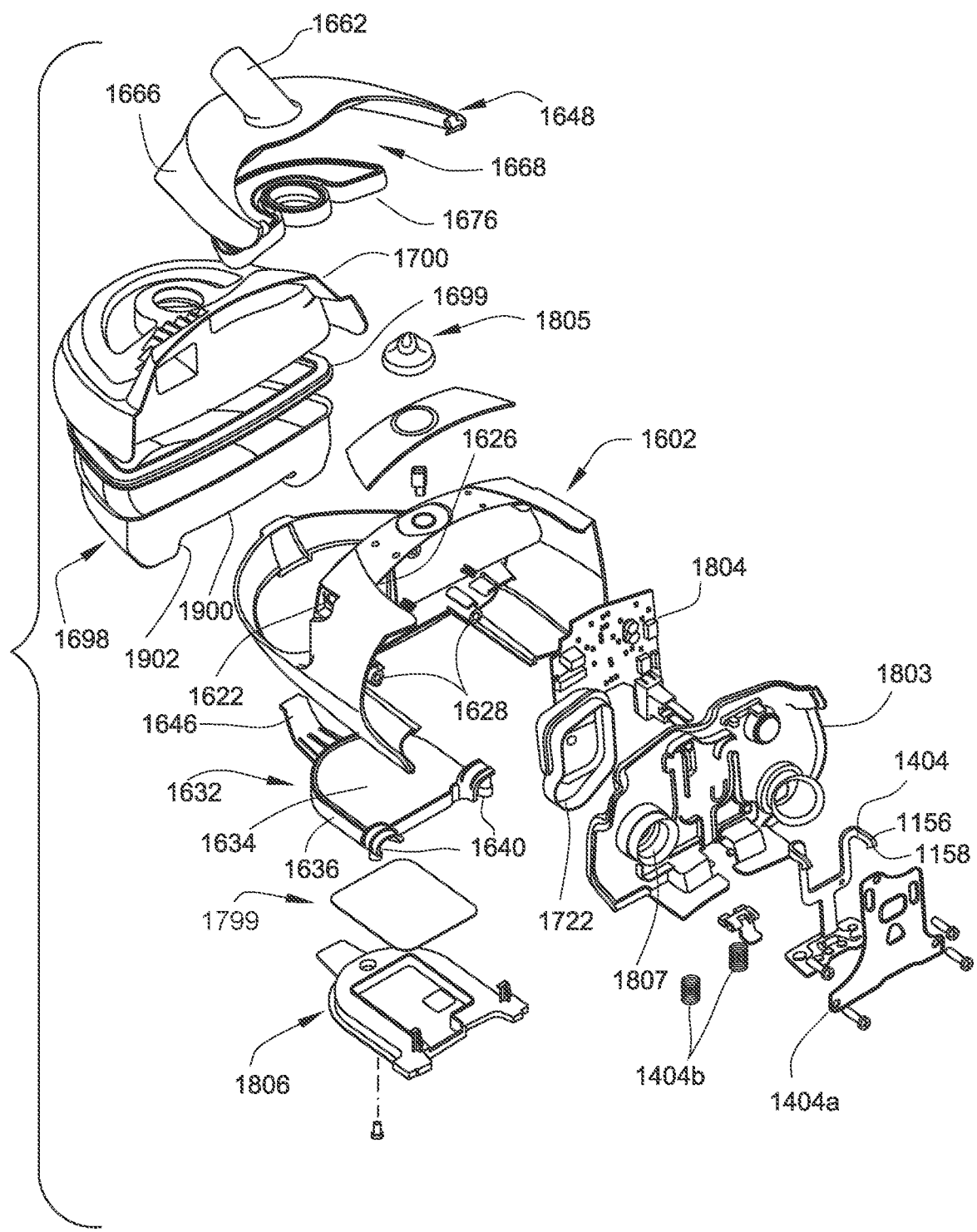
FIG. 54 is an exploded view of a humidifier adapted for use with the flow generator of FIG. 50.
Figure 55:
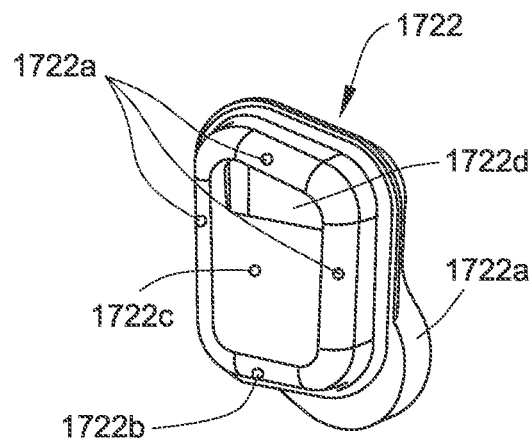
FIG. 55 is a perspective of a seal for the air flow path.

The humidifier of FIG. 54 differs substantially from that of FIGS. 39-49B by a modified sealing arrangement for the air path from the flow generator outlet into the humidifier tub, without the flexible connector component 722 of FIGS. 49A and 49B.

Figure 40:
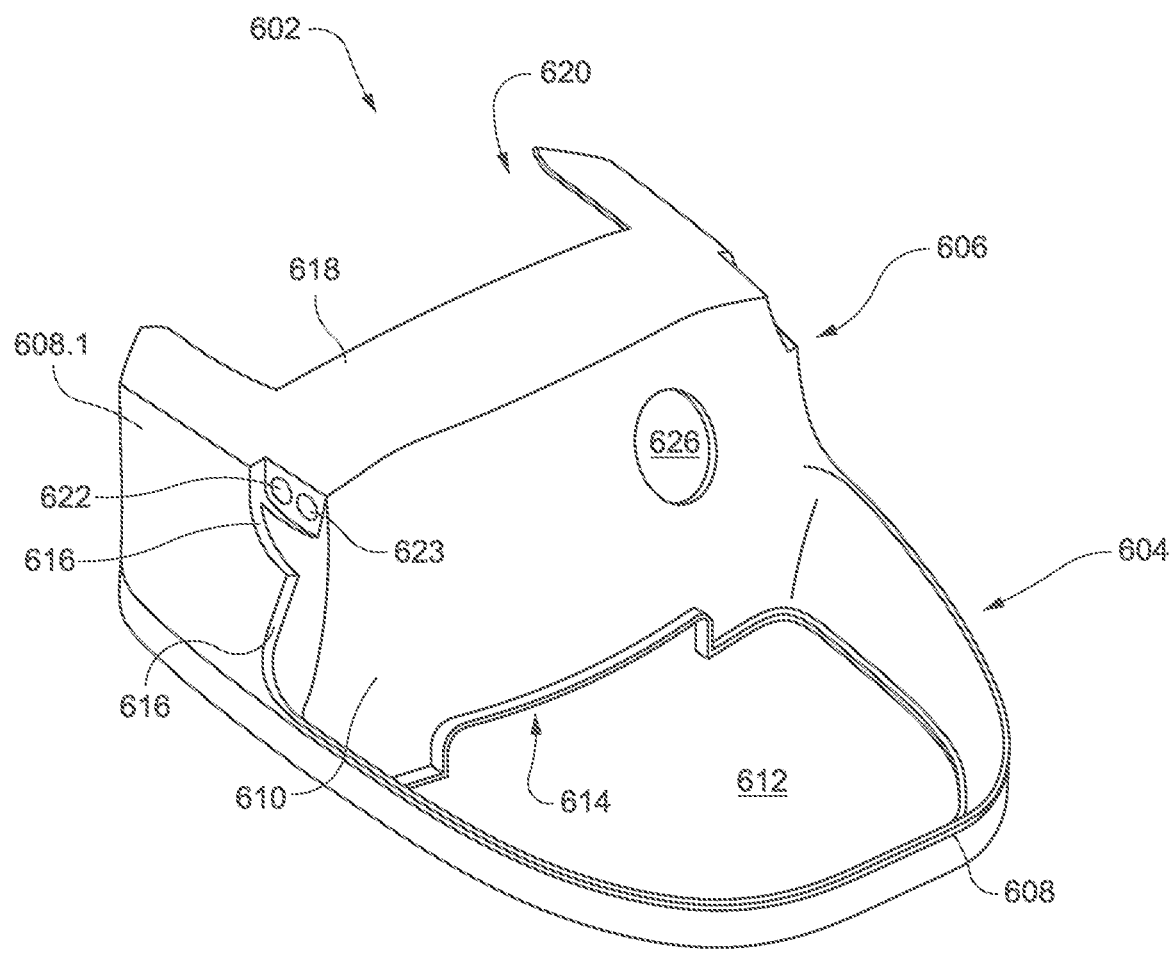
FIG. 40 is a perspective view from the front and above of the component of FIG. 39.

The humidifier front cover 1602 and tub lid 1700 of FIG. 54 are similar in many respects, including their attachment, to their correspondingly numbered components 602, 700 described and shown with reference to FIGS. 39, 40 and 49. The aperture 1626 of the modified front cover is enlarged, and receives an elastomer seal 1722 (FIG. 55) having an inlet connector portion 1722*a* (which connects to the flow generator outlet by way of the air port 1807 formed in the back cover 1803) and a peripheral seal portion 1722*b* which extends about the aperture 1626 periphery at the front face of the cover 1602. A wall portion 1722*c* of the seal closes off a lower part of the aperture 1626, leaving a smaller aperture 1722*d* defined by the seal.

Figure 58A:
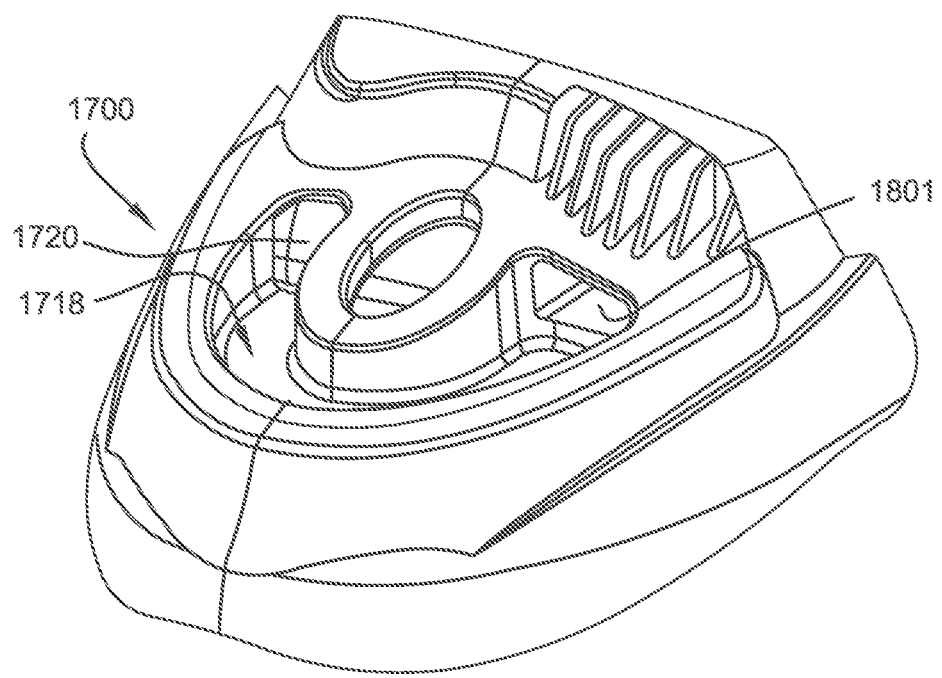
FIG. 58A is a perspective view of the humidifier tub lid of FIG. 54.

As shown in FIG. 58A, the rear surface of the tub lid has an inlet aperture 1801 leading to an inlet end of the U-shaped air passage 1718. When the humidifier lid 1648 is closed, the tub 1698 and tub lid 1700 are pressed rearwards so that the peripheral seal 1722*b* abuts the rear surface of the tub lid in a locus surrounding the rear opening of the inlet aperture 1801, creating a sealed air path from the flow generator to air passage 1718 and into the headspace of the humidifier tub. This allows the humidifier tub to be removed for refilling and replaced without the need for a separate operation to connect the air flow.

Figure 58B:
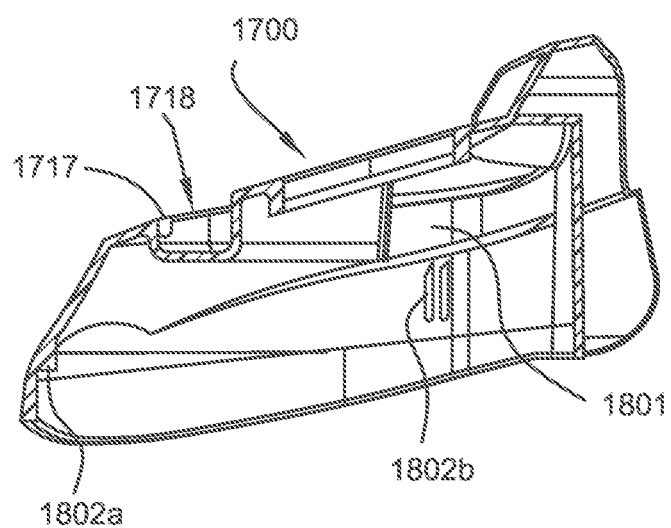
FIG. 58B is a longitudinal cross section of the humidifier tub lid of FIG. 54.

With reference to FIG. 58B, the inside wall of the tub lid 1700 has projections 1802 which serve to limit the press fitting of the tub lid onto the tub base 1698. One projection 1802*a* is provided at the front of the tub, and further projections 1802*b*, or sets of projections, are provided on opposed side walls of the tub lid, forward of the rear of the tub. This positioning of the projections 1802*b* allows one-handed disengagement of the tub base and tub lid by squeezing together of the base and lid at their rear end, causing the connection to pivot about the side projections 1802*b* and the tub and lid to separate at the front. The ability to separate these components one-handed is a feature of considerable utility, especially for stroke patients or other users with limited dexterity.

Figure 56:
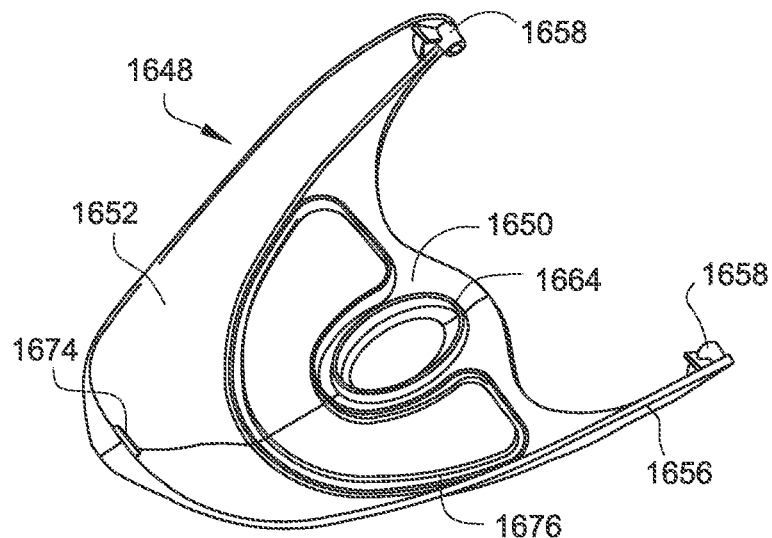
FIG. 56 is an underside perspective of the humidifier lid of FIG. 54.
Figure 57A:
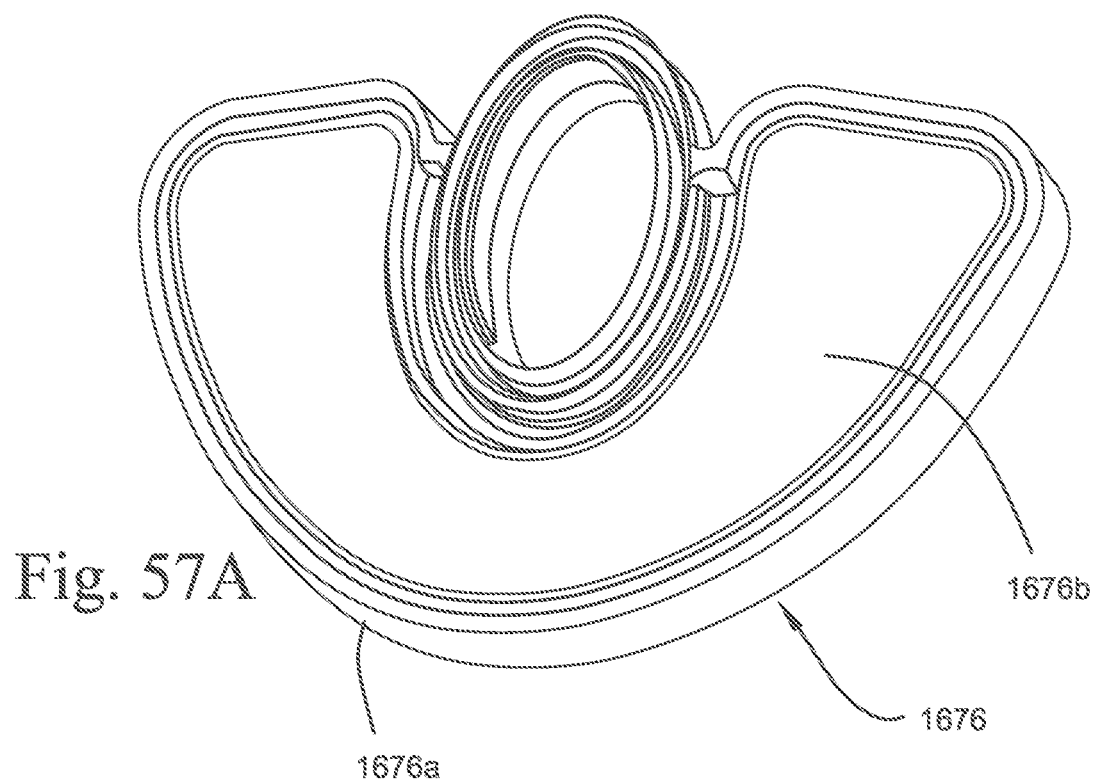
FIG. 57A is a perspective view of the humidifier lid seal of FIG. 54.
Figure 57B:
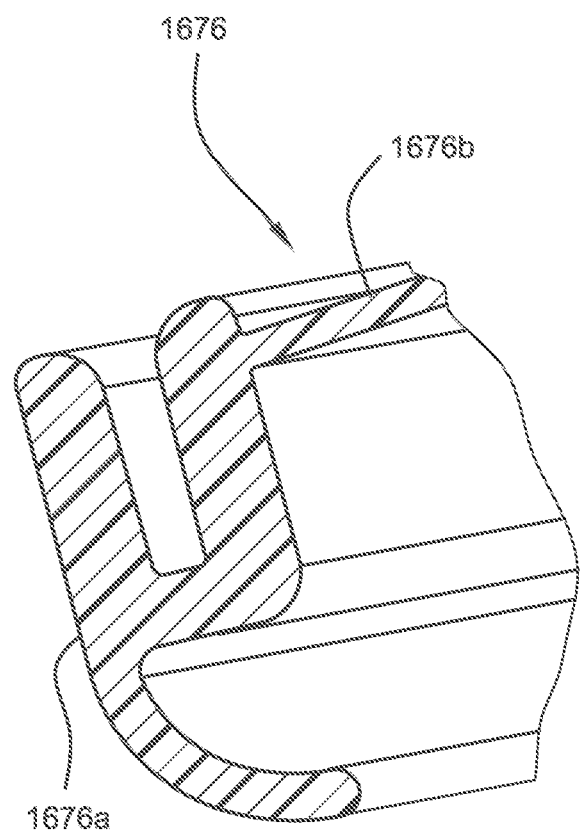
FIG. 57B is a detail cross section of the humidifier lid seal of FIG. 54

FIGS. 56 to 57B show the underside of the humidifier lid 1648 and the seal 1676 which provides a seal to the tub lid 1700 about the U-shaped passage 1718 and the humidified air exit aperture 1716. The seal 1676 comprises an edge seal portion 1676a and membrane portion 1676b.

The humidifier construction of FIG. 54 further includes back cover 1803 which fits to the rear of the front cover 1602 to cover the underside of the heater plate and provide support for a control PCB 1804 and a catch assembly. The catch assembly includes a latch 1404 held in place by latch retainer 1404a to be moveable vertically and resiliently urged downwardly by spring 1404b, so that the tongues 1156 engage in the slots 1155 and snap home to engage the two units by means of the downwardly extending fingers 1158 at the ends of the tongues. In other words, the catch assembly operates to attach the humidifier to the flow generator generally as described for the earlier embodiments. A control knob 1805 on the top of the front cover 1602 is connected to the PCB 1804 to allow patient control over the degree of humidification.

The illustrated humidifier construction provides a compact humidifier adapted for ease of manufacture and use, and further provides protection against backflow of water into the flow generator when the humidifier and flow generator units are assembled together. Backflow protection is provided by the sloping floor of the air passage and the location of the air inlet aperture 1801 and the aperture 1722d in the seal 1722 relative to the air inlet 1720 from the air passage 1718 into the headspace of the humidifier tub 1698. In particular, if the tub is overfilled while in its horizontal position, the water will flow back along the U-shaped air passage 1718 only as far as its forwardmost portion, which has a front wall 1717 lower than the air inlet aperture 1801, and will drain towards the front of the machine. If the machine is tipped up onto its rear, the water will be prevented from flowing back along the air passage from the tub to the air inlet 1801 as the intermediate portion of the air passage 1718 will be above the level of the air inlet 1720. The water will then flow back into the tub once the machine is righted.

It is emphasised that the forgoing disclosure has sought to describe many innovations in flow generator and humidifier design, and it is foreshadowed that these will be the subject of separate claims to protection in applications claiming the priority of this document.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A humidifier assembly configured to humidify a pressurized flow of breathable gas from a flow generator of a continuous positive airway pressure (CPAP) unit, the humidifier assembly comprising:
   a base configured to be attached to the flow generator, the base comprising:
      a floor with a heater pad, an upwardly extending wall, an air inlet extending through the upwardly extending wall and configured to receive the pressurized flow of breathable gas from the flow generator,
      a side wall extending from the upwardly extending wall, and
      a recess portion formed above the heater pad at least in part by the upwardly extending wall and the side wall;
   a water receptacle configured to hold water and be at least partially received within the recess portion of the base, the water receptacle comprising:
      a floor comprising a heat transfer portion configured to transfer heat from the heater pad to water within the water receptacle when the water receptacle is received within the recess portion of the base;
      a side wall about the floor of the water receptacle; and
      a flange at a top of the side wall of the water receptacle;
   a lid hingedly attached to the base, the lid being configured to pivot between an open position and a closed position, the lid comprising:
      a top wall having an interior surface and an exterior surface;
      an outer depending wall that extends from the top wall along at least a portion of a perimeter of the top wall;
      a depending double wall that extends from the interior surface of the top wall at a location between the outer depending wall and a center of the top wall, the depending double wall comprising an outer sub-wall and an inner sub-wall separated from the outer sub-wall by a channel; and
      an outlet pipe configured to be connected to an air delivery tube, the outlet pipe extending upwardly from the exterior surface of the top wall at a location that is within a space bound by the depending double wall;
   a lid seal attached to the interior surface of the top wall of the lid, the lid seal comprising:
      a central portion that is positioned within the space bound by the depending double wall, the central portion comprising a groove configured to receive one of the sub-walls of the depending double wall as a tongue-and-groove arrangement to secure the lid seal to the lid;
      a sealing flange that extends downwardly from a perimeter of the central portion and is configured to be pressed against the flange of the water receptacle around an opening at the top of the water receptacle to form a seal when the lid is in the closed position; and
      an outlet opening in the central portion that is aligned with the outlet pipe to form an air path from an interior of the water receptacle to the outlet pipe through the lid seal; and
   a catch located on the base and configured to lock the lid in the closed position,
   wherein, when the lid is in the closed position, the lid, the lid seal, the water receptacle, and the base together form at least part of a sealed air path from the air inlet in the base to the outlet pipe.

2. The humidifier assembly of claim 1, wherein the central portion of the lid seal is substantially planar between the sealing flange and the outlet opening.

3. The humidifier assembly of claim 1, wherein when the lid is in the closed position, the outer depending wall of the lid engages the side wall of the base.

4. The humidifier assembly of claim 1, wherein the flange of the water receptacle fully surrounds the opening at the top of the water receptacle.

5. The humidifier assembly of claim 1, wherein the perimeter of the central portion of the lid seal has the same shape and size as the space bound by the depending double wall of the lid.

6. The humidifier assembly of claim 1, wherein the floor of the base has an opening, and the heater pad is positioned within the opening in the floor of the base.

7. The humidifier assembly of claim 6, wherein the floor of the water receptacle has an opening in which a heat transfer plate is positioned.

8. The humidifier assembly of claim 7, wherein the heat transfer plate and the heater pad are circular, and wherein the opening in the floor of the base and the opening in the floor of the water receptacle are circular.

9. The humidifier assembly of claim 1, wherein the outlet pipe extends through the top wall of the lid so that portions of the outlet pipe are above and below the top wall of the lid.

10. The humidifier assembly of claim 1, wherein the water receptacle is fully enclosed by the base and the lid when the water receptacle is positioned within the recess portion of the base and the lid is in the closed position.

11. The humidifier assembly of claim 1, wherein the water receptacle is removable from the base when the lid is in the open position.

12. The humidifier assembly of claim 1, wherein the width of the flange of the water receptacle is varied around the opening at the top of the water receptacle.

13. The humidifier assembly of claim 12, wherein when the water receptacle is received within the recess portion of the base, the water receptacle is oriented so that the width of the flange of the water receptacle is greatest at a side of the water receptacle that is opposite to the upwardly extending wall of the base.

14. The humidifier assembly of claim 1, wherein the sealing flange is inwardly curved.

15. The humidifier assembly of claim 1, wherein the upwardly extending wall comprises a humidifier engagement face configured to secure the humidifier assembly to the flow generator, the humidifier engagement face comprising:
an opening that is aligned with the air inlet of the base;
an electrical connector; and
a plurality of latches that are vertically movable and are downwardly biased.

16. The humidifier assembly of claim 1, wherein the central portion of the lid seal is substantially planar between the sealing flange and the outlet opening,
wherein when the lid is in the closed position, the outer depending wall of the lid engages the side wall of the base,
wherein the flange of the water receptacle fully surrounds the opening at the top of the water receptacle,
wherein the perimeter of the central portion of the lid seal has same shape and size as the space bound by the depending double wall of the lid,
wherein the floor of the base has an opening, and the heater pad is positioned within the opening in the floor of the base,
wherein the floor of the water receptacle has an opening in which a heat transfer plate is positioned,
wherein the heat transfer plate and the heater pad are circular, and wherein the opening in the floor of the base and the opening in the floor of the water receptacle are circular,
wherein the outlet pipe extends through the top wall of the lid so that portions of the outlet pipe are above and below the top wall of the lid,
wherein the water receptacle is fully enclosed by the base and the lid when the water receptacle is positioned within the recess portion of the base and the lid is in the closed position,
wherein the water receptacle is removable from the base when the lid is in the open position,
wherein the width of the flange of the water receptacle is varied around the opening at the top of the water receptacle,
wherein when the water receptacle is received within the recess portion of the base, the water receptacle is oriented so that the width of the flange of the water receptacle is greatest at a side of the water receptacle that is opposite to the upwardly extending wall of the base,
wherein the sealing flange is inwardly curved,
wherein the upwardly extending wall comprises a humidifier engagement face configured to secure the humidifier assembly to the flow generator, and
wherein the humidifier engagement face comprise an opening that is aligned with the air inlet of the base, an electrical connector, and a plurality of latches that are vertically movable and are downwardly biased.

17. A continuous positive airway pressure (CPAP) unit configured to deliver a pressurized flow of breathable gas to a patient's airways, the CPAP unit comprising:
a flow generator configured to pressurize the flow of breathable gas; and
the humidifier assembly of claim 1.

18. The CPAP unit of claim 17, wherein the flow generator and the humidifier assembly are configured to be coupled together by way of a lateral movement toward each other.

19. The CPAP unit of claim 17, wherein the upwardly extending wall of the humidifier assembly comprises a humidifier engagement face configured to secure the humidifier assembly to the flow generator, the humidifier engagement face comprising:
an opening that is aligned with the air inlet of the base;
an electrical connector; and
a plurality of latches that are vertically movable and are downwardly biased.

20. The CPAP unit of claim 19, wherein the flow generator comprises an upwardly extending wall with a flow generator engagement face configured to engage the humidifier engagement face and secure the flow generator to the humidifier assembly, the flow generator engagement face comprising:
an opening through which an air outlet of the flow generator extends, the air outlet of the flow generator being configured to be received within the opening in the humidifier engagement face;
an electrical connector configured to receive the electrical connector of the humidifier assembly; and
a plurality of openings configured to receive the latches of the humidifier engagement face.

21. The CPAP unit of claim 20, wherein the latches of the humidifier engagement face are configured to interlock with the openings in the flow generator engagement face upon the latches being received within the openings in the flow generator engagement face.

22. The CPAP unit of claim 17, wherein the humidifier assembly is separable from the flow generator.

23. The CPAP unit of claim 17, further comprising an air delivery tube connected to the outlet pipe of the humidifier assembly.

* * * * *

UNITED STATES PATENT AND TRADEMARK OFFICE
CERTIFICATE OF CORRECTION

PATENT NO. : 11,235,115 B2  
APPLICATION NO. : 17/318393  
DATED : February 1, 2022  
INVENTOR(S) : Geoffrey Crumblin Page 1 of 1

It is certified that error appears in the above-identified patent and that said Letters Patent is hereby corrected as shown below:

In the Claims

Claim 1, at Column 24, Line 11, "a side wall about the floor of the water receptacle; and" should read -- a side wall above the floor of the water receptacle; and --.

Signed and Sealed this  
Twelfth Day of April, 2022

Drew Hirshfeld  
*Performing the Functions and Duties of the*  
*Under Secretary of Commerce for Intellectual Property and*  
*Director of the United States Patent and Trademark Office*